US009598684B2

(12) United States Patent
Helmerhorst et al.

(10) Patent No.: US 9,598,684 B2
(45) Date of Patent: *Mar. 21, 2017

(54) *ROTHIA* SPECIES GLUTEN-DEGRADING ENZYMES AND USES THEREOF

(75) Inventors: Eva J. Helmerhorst, Chestnut Hill, MA (US); Frank G. Oppenheim, Chestnut Hill, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 457 days.

This patent is subject to a terminal disclaimer.

(21) Appl. No.: 13/808,685

(22) PCT Filed: Jul. 7, 2011

(86) PCT No.: PCT/US2011/043118
§ 371 (c)(1),
(2), (4) Date: Mar. 20, 2013

(87) PCT Pub. No.: WO2012/006384
PCT Pub. Date: Jan. 12, 2012

(65) Prior Publication Data
US 2013/0171109 A1 Jul. 4, 2013

Related U.S. Application Data

(60) Provisional application No. 61/362,000, filed on Jul. 7, 2010.

(51) Int. Cl.
*A01N 63/00* (2006.01)
*C12N 9/52* (2006.01)
*A61K 38/48* (2006.01)
*C12R 1/01* (2006.01)

(52) U.S. Cl.
CPC .............. *C12N 9/52* (2013.01); *A23L 33/135* (2016.08); *A23L 33/195* (2016.08); *A61K 38/482* (2013.01); *C12R 1/01* (2013.01)

(58) Field of Classification Search
CPC ....... A61K 38/482; C12N 9/52; A23L 33/195; A23L 33/135; C12R 1/01
See application file for complete search history.

(56) References Cited

U.S. PATENT DOCUMENTS

| | | |
|---|---|---|
| 7,303,871 B2 | 12/2007 | Hausch et al. |
| 7,320,788 B2 | 1/2008 | Shan et al. |
| 2005/0249719 A1 | 11/2005 | Shan et al. |
| 2005/0281914 A1 | 12/2005 | Steele et al. |
| 2006/0240475 A1 | 10/2006 | Khosla et al. |
| 2008/0193436 A1 | 8/2008 | Shan et al. |
| 2010/0092451 A1 | 4/2010 | Gass et al. |

FOREIGN PATENT DOCUMENTS

WO 2007/019411 2/2007

OTHER PUBLICATIONS

Steffensen B., New bacterial genomes in the human oral microbiome database (homd), letter sent to oral research investigators on Jun. 7, 2010, pp. 1-5; obtained from web at—http://dental.uthscsa.edu/research/announcements/2010-06-07_NewBacterial.pdf.*
Beyer P., Medical Nutrition Therapy for Lower Gastrointestinal Tract Disorders, from Krause's Food, Nutrition, & Diet Therapy—Edited by L. Kathleen Mahan, Sylvia Escott-Stump, 11th edition, Chapter 30, published online—Nov. 18, 2006, pp. 705-737 (total 35 pages attached).*
Alvine Pharmaceuticals, Inc. website, "About Alvine" page. Accessed online on Jul. 7, 2010.
Alvine media release of Oct. 29, 2008, San Carlos, California. Available online at http://www.alvinepharma.com/press-october292008/.
Brown et al., The Australian Coeliac media release, (2008). "Clinical trials of ALV003—what it means for Australian coeliacs?".
De Palma et al., J. Leukoc. Biol., 87:765-778 (2010). "Pivotal Advance: Bifidobacteria and Gram-negative bacteria differentially influence immune responses in the proinflammatory milieu of celiac disease."
Dodson et al., Nucleotide and Predicted Amino Acid Sequence of Rothia ATCC 25296 Neprilysin Peptidase; integrated into UniprotKB/TrEMBL on Sep. 22, 2009. downloaded from http://www.uniprot.org/uniprot/C6R2W3.text.
Helmerhorst, et al., AADR Annual Meeting, Mar. 3-6, 2010, Washington D.C. "988. The Oral Microflora Contains Gluten-Degrading Microorganisms," presented Mar. 5, 2010.
Lindfors et al., Clinical and Experimental Immunology, 152:552-558 (2008). "Live probiotic Bifidobacterium lactis bacteria inhibit the toxic effects induced by wheat gliadin in epithelial cell culture."
Mitea et al., Gut, 57:25-32 (2008). "Efficient degradation of gluten by a prolyl endoprotease in a gastrointestinal model: implications for coeliac disease."
Ou et al., Am J Gastroenterol, 104:3058-3067 (2009). "Proximal Small Intestinal Microbiota and Identification of Rod-Shaped Bacteria Associated With Childhood Celiac Disease."
Bethune et al., J Pharmacol Exp Ther, 329(2):657-668 (2009). "Interferon-gamma released by gluten-stimulated celiac disease-specific intestinal T cells enhances the transepithelial flux of gluten peptides."
Cerf-Bensussan et al., Gut, 56(2):157-60 (2007). "A new approach to managing coeliac disease."

(Continued)

*Primary Examiner* — Satyendra K Singh
(74) *Attorney, Agent, or Firm* — Nixon Peabody LLP; Ronald I. Eisenstein; Tari W. Mills

(57) ABSTRACT

There are gluten-degrading enzymes found in *Rothia* species bacteria that are capable of breaking peptide bonds in -XPQ-, -QQP-, -PPF-, -LYP- and/or -PFP-containing peptides. These enzymes are acidic enzymes; they retain protease activity at acidic pH, eg., at 3.0, and have isoelectric points in a pH range of 2.0-7.0. Embodiments herein provide isolated enzyme compositions and probiotic compositions comprising at least one acidic gluten-degrading enzyme or a *Rothia* species bacteria. Also provided herein are methods of treatment of celiac disease or a related disorder, treatment of gluten-containing foodstuff, degrading and/or detoxifying gluten comprising the acidic gluten-degrading enzyme and/or compositions.

14 Claims, 25 Drawing Sheets

(56) References Cited

OTHER PUBLICATIONS

Davy et al., Plant Physiol, 117:255-261 (1998). "Substrate specificity of barley cysteine endoproteases EP-A and EP-B."

Gass et al., Cell Mol Life Sci, 64(3):345-55 (2007). "Prolyl endopeptidases."

Gass et al., Gastroenterology, 133(2):472-80 (2007). "Combination enzyme therapy for gastric digestion of dietary gluten in patients with celiac sprue."

Helmerhorst et al., PLoS ONE, 5(10):e13264 (2010). "Discovery of a novel and rich source of gluten-degrading microbial enzymes in the oral cavity."

Helmerhorst et al., The Journal of Biological Chemistry, 283(29):19957-19966 (2008). "Identification of Lys-Pro-Gln as a novel cleavage site specificity of saliva-associated proteases."

Loponen et al., Academic Dissertation, University of Helsinki, Department of Food and Technology, 2006. "Prolamine degradation in sourdoughs."

Shan et al., Biochem J, 383(Pt 2):311-8 (2004). "Comparative biochemical analysis of three bacterial prolyl endopeptidases: implications for coeliac sprue."

Stepniak et al., Am J Physiol Gastrointest Liver Physiol, 291:G621-629 (2006). "Highly efficient gluten degradation with a newly identified prolyl endoprotease: implications for celiac disease."

Tian et al., The Journal of Biological Chemistry, 281(10):6559-6572 (2006). "Determination of the substrate specificity of tripeptidyl-peptidase I using combinatorial peptide libraries and development of improved fluorogenic substrates."

Zamakhchari et al., PLoS ONE, 6(9):e24455 (2011). "Identification of Rothia bacteria as gluten-degrading natural colonizers of the upper gastro-intestinal tract."

\* cited by examiner

FIG. 7A

```
         Gliadin 33-mer Residue#
          1 2 3 4 5 6 7 8 9 10 11 12 13 14 15 16 17 18 19 20 21 22 23 24 25 26 27 28 29 30 31 32 33
Peptide #
   1      L Q L Q P F P Q P Q  L  P  Y  P  Q  P  Q  L  P  Y  P  Q  P  Q  L  P  Y  P  Q  P  Q  P  F
   2      L Q L Q P F P Q P Q  L  P  Y  P  Q  P  Q  L  P  Y  P  Q  P  Q  L
   3      L Q L Q P F P Q P Q  L  P  Y  P  Q  P  Q  L  P  Y  P  Q
   4      L Q L Q P F P Q P Q  L  P  Y  P  Q  P  Q  L
   5      L Q L Q P F P Q P Q  L  P  Y  P  Q
   6      L Q L Q P F P Q P Q  L  P  Y  P
   7      L Q L Q P F P Q P Q  L  P  Y
   8      L Q L Q P F P Q P Q  L  P
   9      L Q L Q P F P Q P Q  L
  10      L Q L Q P F P Q P Q
  11      L Q L Q P F P Q P 12                                                              Y  P  Q  P  Q  P  F
  13                                                           P  Y  P  Q  P  Q  P  F
  14                                                        L  P  Y  P  Q  P  Q  P  F
  15                                                  P  Q  L  P  Y  P  Q  P  Q  P  F
  16                                               Q  P  Q  L  P  Y  P  Q  P  Q  P  F
  17                                            P  Q  P  Q  L  P  Y  P  Q  P  Q  P  F
  18                                         Y  P  Q  P  Q  L  P  Y  P  Q  P  Q  P  F
  19                                      P  Y  P  Q  P  Q  L  P  Y  P  Q  P  Q  P  F
  20                                   L  P  Y  P  Q  P  Q  L  P  Y  P  Q  P  Q  P  F
  21                                Q  L  P  Y  P  Q  P  Q  L  P  Y  P  Q  P  Q  P  F
  22                             P  Q  L  P  Y  P  Q  P  Q  L  P  Y  P  Q  P  Q  P  F
  23                       P  Q  P  Q  L  P  Y  P  Q  P  Q  L  P  Y  P  Q  P  Q  P  F
  24                    Y  P  Q  P  Q  L  P  Y  P  Q  P  Q  L  P  Y  P  Q  P  Q  P  F
  25                 P  Y  P  Q  P  Q  L  P  Y  P  Q  P  Q  L  P  Y  P  Q  P  Q  P  F
  26              L  P  Y  P  Q  P  Q  L  P  Y  P  Q  P  Q  L  P  Y  P  Q  P  Q  P  F
  27        P  Q  L  P  Y  P  Q  P  Q  L  P  Y  P  Q  P  Q  L  P  Y  P  Q  P  Q  P  F
  28  P Q  P Q L P Y  P  Q  P  Q  L  P  Y  P  Q  P  Q  L  P  Y  P  Q  P  Q  P  F
  29      F P Q P Q L P Y P Q  P  Q  L  P  Y  P  Q  P  Q  L  P  Y  P  Q  P  Q  P  F
  30        P F P Q P Q L P Y  P  Q  P  Q  L  P  Y  P  Q  P  Q  L  P  Y  P  Q  P  Q  P  F
  31          Q P F P Q P Q L  P  Y  P  Q  P  Q  L  P  Y  P  Q  P  Q  L  P  Y  P  Q  P  Q  P  F
  32        L Q P F P Q P Q L  P  Y  P  Q  P  Q  L  P  Y  P  Q  P  Q  L  P  Y  P  Q  P  Q  P  F
  33      Q L Q P F P Q P Q L  P  Y  P  Q  P  Q  L  P  Y  P  Q  P  Q  L  P  Y  P  Q  P  Q  P  F 34              F P Q P Q L  P  Y  P  Q  P  Q  L  P
  35                  Q P Q L  P  Y  P  Q  P  Q  L  P  Y  P  Q  P  Q
  36                  Q P Q L  P  Y  P  Q  P  Q  L  P  Y  P  Q  P  Q  L
  37                  Q P Q L  P  Y  P  Q  P  Q  L  P  Y  P  Q  P  Q  L  P  Y
  38                  Q P Q L  P  Y  P  Q  P  Q  L  P  Y  P  Q  P  Q  L  P  Y  P
  39                  Q P Q L  P  Y  P  Q  P  Q  L  P  Y  P  Q  P  Q  L  P  Y  P  Q
  40                  Q P Q L  P  Y  P  Q  P  Q  L  P  Y  P  Q  P  Q  L  P  Y  P  Q  P  Q  P
  41                    P Q L  P  Y  P  Q  P  Q  L  P  Y  P  Q  P  Q  L  P  Y
  42                      Q L  P  Y  P  Q  P  Q  L  P  Y  P  Q  P  Q  L  P  Y  P  Q  P
  43                         L  P  Y  P  Q  P  Q  L  P  Y  P  Q  P  Q  L  P  Y  P
  44                         L  P  Y  P  Q  P  Q  L  P  Y  P  Q  P  Q  L  P  Y  P  Q  P
  45                            P  Y  P  Q  P  Q  L  P  Y  P  Q  P  Q  L  P
  46                                  Q  P  Q  L  P  Y  P  Q  P  Q  L  P  Y  P  Q  P  Q
```

| | Gliadin 26-mer Residue # | | | | | | | | | | | | | | | | | | | | | | | | | |
|---|---|---|---|---|---|---|---|---|---|---|---|---|---|---|---|---|---|---|---|---|---|---|---|---|---|---|
| Peptide # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 |
| 1 | F | L | Q | P | Q | Q | P | F | P | Q | Q | P | Q | Q | P | Y | P | Q | Q | P | Q | Q | P | F | P | Q |
| 2 | F | L | Q | P | Q | Q | P | F | P | Q | Q | P | Q | Q | P | Y | P | Q | Q | P | Q | Q | P | F | P | |
| 3 | F | L | Q | P | Q | Q | P | F | P | Q | Q | P | Q | Q | P | Y | P | Q | Q | P | Q | Q | P | | | |
| 4 | F | L | Q | P | Q | Q | P | F | P | Q | Q | P | Q | Q | P | Y | P | Q | Q | P | Q | Q | | | | |
| 5 | F | L | Q | P | Q | Q | P | F | P | Q | Q | P | Q | Q | P | Y | P | Q | Q | P | Q | | | | | |
| 6 | F | L | Q | P | Q | Q | P | F | P | Q | Q | P | Q | Q | P | Y | P | Q | Q | P | | | | | | |
| 7 | F | L | Q | P | Q | Q | P | F | P | Q | Q | P | Q | Q | P | Y | P | Q | Q | | | | | | | |
| 8 | F | L | Q | P | Q | Q | P | F | P | Q | Q | P | Q | Q | P | Y | P | Q | | | | | | | | |
| 9 | F | L | Q | P | Q | Q | P | F | P | Q | Q | P | Q | Q | P | Y | P | | | | | | | | | |
| 10 | F | L | Q | P | Q | Q | P | F | P | Q | Q | P | Q | Q | P | Y | | | | | | | | | | |
| 11 | F | L | Q | P | Q | Q | P | F | P | Q | Q | P | Q | Q | P | | | | | | | | | | | |
| 12 | F | L | Q | P | Q | Q | P | F | P | Q | Q | P | Q | Q | | | | | | | | | | | | |
| 13 | F | L | Q | P | Q | Q | P | F | P | Q | Q | P | Q | | | | | | | | | | | | | |
| 14 | F | L | Q | P | Q | Q | P | F | P | Q | Q | P | | | | | | | | | | | | | | |
| 15 | F | L | Q | P | Q | Q | P | F | P | Q | Q | | | | | | | | | | | | | | | |
| 16 | F | L | Q | P | Q | Q | P | F | P | Q | | | | | | | | | | | | | | | | |
| 17 | F | L | Q | P | Q | Q | P | F | P | | | | | | | | | | | | | | | | | |
| 18 | F | L | Q | P | Q | Q | P | F | | | | | | | | | | | | | | | | | | |
| 19 | | | | | | | | | | | | | | | | | P | Q | Q | P | Q | Q | P | F | P | Q |
| 20 | | | | | | | | | | | | | | | | P | Y | P | Q | Q | P | Q | Q | P | F | P | Q |
| 21 | | | | | | | | | | | | | | | P | Y | P | Q | Q | P | Q | Q | P | F | P | Q |
| 22 | | | | | | | | | | | | | | Q | P | Y | P | Q | Q | P | Q | Q | P | F | P | Q |
| 23 | | | | | | | | | | | | | Q | Q | P | Y | P | Q | Q | P | Q | Q | P | F | P | Q |
| 24 | | | | | | | | | | | | P | Q | Q | P | Y | P | Q | Q | P | Q | Q | P | F | P | Q |
| 25 | | | | | | | | | | | Q | P | Q | Q | P | Y | P | Q | Q | P | Q | Q | P | F | P | Q |
| 26 | | | | | | | | | | Q | Q | P | Q | Q | P | Y | P | Q | Q | P | Q | Q | P | F | P | Q |
| 27 | | | | | | | | | P | Q | Q | P | Q | Q | P | Y | P | Q | Q | P | Q | Q | P | F | P | Q |
| 28 | | | | | | | | F | P | Q | Q | P | Q | Q | P | Y | P | Q | Q | P | Q | Q | P | F | P | Q |
| 29 | | | | | | | P | F | P | Q | Q | P | Q | Q | P | Y | P | Q | Q | P | Q | Q | P | F | P | Q |
| 30 | | | | | | Q | P | F | P | Q | Q | P | Q | Q | P | Y | P | Q | Q | P | Q | Q | P | F | P | Q |
| 31 | | | | | Q | Q | P | F | P | Q | Q | P | Q | Q | P | Y | P | Q | Q | P | Q | Q | P | F | P | Q |
| 32 | | | | Q | P | Q | Q | P | F | P | Q | Q | P | Q | Q | P | Y | P | Q | Q | P | Q | Q | P | F | P | Q |
| 33 | | | L | Q | P | Q | Q | P | F | P | Q | Q | P | Q | Q | P | Y | P | Q | Q | P | Q | Q | P | F | P | Q |

Proteins identified in DEAE-P1A-HIC-P3

| Protein | # peptides |
|---|---|
| gi\|255325942\|ref\|ZP_05367032.1\| Tat pathway signal sequence domain protein [Rothia mucilaginosa ATCC 25296] | 99 |
| gi\|255326668\|ref\|ZP_05367744.1\| hypothetical protein ROTMU0001_0500 [Rothia mucilaginosa ATCC 25296] | 19 |
| gi\|255326151\|ref\|ZP_05367238.1\| hypothetical protein ROTMU0001_1834 [Rothia mucilaginosa ATCC 25296] | 39 |

FIG. 13

| Clan | Fam. | MEROPS ID | MW | Peptidase or homologue (subtype) | Type |
|---|---|---|---|---|---|
| MH | M18 | M18.002 | 46 kD | aspartyl aminopeptidase | Hydrolase (Metallo) |
| PA | S1 | S01.513 | 40 kD | Rv3671c peptidase (*Mycobacterium tuberculosis*) | Hydrolase |
| SB | S8 | unassigned | 66 kD | subfamily S8A unassigned peptidases | Hydrolase (serine) |
| SC | S9 | non-peptidase homologue | 52 kD | family S9 non-peptidase homologues | Esterase |
| SC | S9 | unassigned | 30 kD | family S9 unassigned peptidases | ? |
| SC | S9 | unassigned | 27 kD | family S9 unassigned peptidases | Hydrolase |
| SC | S9 | unassigned | 54 kD | family S9 unassigned peptidases | Hydrolase/transferase |
| SC | S33 | unassigned | 47 kD | family S33 unassigned peptidases | Homoserine-O-acetyl transferase |
| SC | S33 | unassigned | 37 kD | family S33 unassigned peptidases | Hydrolase |
| SC | S33 | unassigned | 47 kD | family S33 unassigned peptidases | Homoserine-O-acetyl transferase |
| SC | S33 | unassigned | 53 kD | family S33 unassigned peptidases | Prolyl amino peptidase |

*FIG. 14*

>gi|255325942|ref|ZP_05367032.1| Tat pathway signal sequence domain protein [Rothia mucilaginosa ATCC 25296]

MSTNISRRKVVAGAAWAAAPVVAASAAVPAFASSTECDYASAPKFNISGQPSGAKDTVKFTVPAKVDKIKFEVAGGAGGGSNQVAGGSGALVTGVIP
VKEGQVIELVAASGGVAYLESVRGVDSPALWQTRPATGGKGYGNGGDVNEQPVPADVKAQVDANWSKPSDMKRYLYGGSGGGSSALINGTPVAVA
GGGGGAGIRTQPGTNNMPSGKYYNPKAVDASTTRLSDPDVKSVLPAGASASAAVGDSAETSISHYTVLKPHTTDGTAMKVAGGHGGGNGQGGAGGE
QPLLYSTLGNVYGVLGFKSQNKQELFSSATAGDKGGSGFDGKGADGVFAYSYQIDNNDISKLEIVHATNPVNLNDKTNLDEDSTRKSFNGYQTVVS
AGGGAGYGGGGSGAARGLSSIITSQKWNGNEEPTRYRQNVSALLQAGAGAGGSYVAPSVTGGAIASANNAAKASGVRNPGYVKVYLCERS

FIG. 15

>gi|255326668|ref|ZP_05367744.1| hypothetical protein ROTMU0001_0500 [Rothia mucilaginosa ATCC 25296]

MTQPISRRSVAKAGVWSAPVIATSAAVPAYAASSRSDDSEEKLTIQSGLFVSAQYGGGFVGYASSTSTGPIHPTTPEAYF
ASSSKPQSDLNWDDSASKPTNPDLFINGEGTFTPVNNSQTASPGSYVASSGFWWSVPTTAPKTGTGYVAGSTATLAAGAT
FVTDVEYTVPANALNGAKSGKVNGQAWTPNGRAPKGTLAELVASAGQARYLSVAQAAGNWSASVPTVTKNSDGTYTFKGR
ITFTTTKAYTLKQTGNKLYGQVVIMPGIVFFNPAQGWVSYKQTSSIQNATINYSGNGYTDTKVLSGAETTTQINP

*FIG. 16*

>gi|255326151|ref|ZP_05367238.1| hypothetical protein ROTMU0001_1834 [Rothia mucilaginosa ATCC 25296

]MDIHSTKSHSEQSGKLMGRRTLVKGAAWATPVVAATAVVPAYAASKNPCEYGTIVSVPWGERANRRYKGTVNEEYE
WAVMPTSNCSPQPQTYFIDNTTPENKLAYPWGRYEGVSDFPPIYPPNGKDTPDYTSKDGVGGVIINVRVENVAG
DVSYAPTPTGADRFAFGESDANRKNMYYAEGYKGKGANPPVVRLNDNYKGSRSTYIAHGKYNYLHFPDGPRPPKENS
PLWTYAYGKHYTTAEGRDGWSWDIQVMANITHPNAGQDVVSYMTYLRKHTYGDPAHQSAKVIPVQYRVIVTSPWGTVT
YLSAAV

*FIG. 17*

SEQUENCE LISTING

```
<160> NUMBER OF SEQ ID NOS: 169

<210> SEQ ID NO 1
<211> LENGTH: 33
<212> TYPE: PRT
<213> ORGANISM: Unknown
<220> FEATURE:
<223> OTHER INFORMATION: Description of Unknown: Alpha2-gliadin
      peptide

<400> SEQUENCE: 1

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 2
<211> LENGTH: 26
<212> TYPE: PRT
<213> ORGANISM: Unknown
<220> FEATURE:
<223> OTHER INFORMATION: Description of Unknown: Gamma-gliadin
      peptide

<400> SEQUENCE: 2

Phe Leu Gln Pro Gln Gln Pro Phe Pro Gln Gln Pro Gln Gln Pro Tyr
1               5                   10                  15

Pro Gln Gln Pro Gln Gln Pro Phe Pro Gln
            20                  25

<210> SEQ ID NO 3
<211> LENGTH: 12
<212> TYPE: PRT
<213> ORGANISM: Unknown
<220> FEATURE:
<223> OTHER INFORMATION: Description of Unknown: Toxic gluten
      oligopeptide derived during human digestion of
      gliadins and related storage proteins

<400> SEQUENCE: 3

Gln Leu Gln Pro Phe Pro Gln Pro Gln Leu Pro Tyr
1               5                   10

<210> SEQ ID NO 4
<211> LENGTH: 9
<212> TYPE: PRT
<213> ORGANISM: Unknown
<220> FEATURE:
<223> OTHER INFORMATION: Description of Unknown: Toxic gluten
      oligopeptide derived during human digestion of
      gliadins and related storage proteins

<400> SEQUENCE: 4

Pro Phe Pro Gln Pro Gln Leu Pro Tyr
1               5

<210> SEQ ID NO 5
<211> LENGTH: 14
<212> TYPE: PRT
<213> ORGANISM: Unknown
```

```
<220> FEATURE:
<223> OTHER INFORMATION: Description of Unknown: Toxic gluten
      oligopeptide derived during human digestion of
      gliadins and related storage proteins

<400> SEQUENCE: 5

Pro Gln Pro Gln Leu Pro Tyr Pro Gln Pro Gln Leu Pro Tyr
1               5                   10

<210> SEQ ID NO 6
<211> LENGTH: 9
<212> TYPE: PRT
<213> ORGANISM: Unknown
<220> FEATURE:
<223> OTHER INFORMATION: Description of Unknown: Toxic gluten
      oligopeptide derived during human digestion of
      gliadins and related storage proteins

<400> SEQUENCE: 6

Pro Gln Pro Gln Leu Pro Tyr Pro Gln
1               5

<210> SEQ ID NO 7
<211> LENGTH: 10
<212> TYPE: PRT
<213> ORGANISM: Unknown
<220> FEATURE:
<223> OTHER INFORMATION: Description of Unknown: Toxic gluten
      oligopeptide derived during human digestion of
      gliadins and related storage proteins

<400> SEQUENCE: 7

Gln Pro Gln Gln Ser Phe Pro Gln Gln Gln
1               5                   10

<210> SEQ ID NO 8
<211> LENGTH: 9
<212> TYPE: PRT
<213> ORGANISM: Unknown
<220> FEATURE:
<223> OTHER INFORMATION: Description of Unknown: Toxic gluten
      oligopeptide derived during human digestion of
      gliadins and related storage proteins

<400> SEQUENCE: 8

Pro Gln Gln Ser Phe Pro Gln Gln Gln
1               5

<210> SEQ ID NO 9
<211> LENGTH: 12
<212> TYPE: PRT
<213> ORGANISM: Unknown
<220> FEATURE:
<223> OTHER INFORMATION: Description of Unknown: Toxic gluten
      oligopeptide derived during human digestion of
      gliadins and related storage proteins

<400> SEQUENCE: 9

Gln Leu Gln Pro Phe Pro Gln Pro Glu Leu Pro Tyr
1               5                   10

<210> SEQ ID NO 10
<211> LENGTH: 14
<212> TYPE: PRT
<213> ORGANISM: Unknown
<220> FEATURE:
<223> OTHER INFORMATION: Description of Unknown: Toxic gluten
      oligopeptide derived during human digestion of
      gliadins and related storage proteins
```

<400> SEQUENCE: 10

Pro Gln Pro Glu Leu Pro Tyr Pro Gln Pro Glu Leu Pro Tyr
1               5                   10

<210> SEQ ID NO 11
<211> LENGTH: 10
<212> TYPE: PRT
<213> ORGANISM: Unknown
<220> FEATURE:
<223> OTHER INFORMATION: Description of Unknown: Toxic gluten
      oligopeptide derived during human digestion of
      gliadins and related storage proteins

<400> SEQUENCE: 11

Gln Pro Gln Gln Ser Phe Pro Glu Gln Gln
1               5                   10

<210> SEQ ID NO 12
<211> LENGTH: 9
<212> TYPE: PRT
<213> ORGANISM: Unknown
<220> FEATURE:
<223> OTHER INFORMATION: Description of Unknown: Toxic gluten
      oligopeptide derived during human digestion of
      gliadins and related storage proteins

<400> SEQUENCE: 12

Ile Gln Pro Gln Gln Pro Ala Gln Leu
1               5

<210> SEQ ID NO 13
<211> LENGTH: 9
<212> TYPE: PRT
<213> ORGANISM: Unknown
<220> FEATURE:
<223> OTHER INFORMATION: Description of Unknown: Toxic gluten
      oligopeptide derived during human digestion of
      gliadins and related storage proteins

<400> SEQUENCE: 13

Gln Gln Pro Gln Gln Pro Tyr Pro Gln
1               5

<210> SEQ ID NO 14
<211> LENGTH: 9
<212> TYPE: PRT
<213> ORGANISM: Unknown
<220> FEATURE:
<223> OTHER INFORMATION: Description of Unknown: Toxic gluten
      oligopeptide derived during human digestion of
      gliadins and related storage proteins

<400> SEQUENCE: 14

Ser Gln Pro Gln Gln Gln Phe Pro Gln
1               5

<210> SEQ ID NO 15
<211> LENGTH: 9
<212> TYPE: PRT
<213> ORGANISM: Unknown
<220> FEATURE:
<223> OTHER INFORMATION: Description of Unknown: Toxic gluten
      oligopeptide derived during human digestion of
      gliadins and related storage proteins

<400> SEQUENCE: 15

Gln Gln Pro Phe Pro Gln Gln Pro Gln

```
<210> SEQ ID NO 16
<211> LENGTH: 9
<212> TYPE: PRT
<213> ORGANISM: Unknown
<220> FEATURE:
<223> OTHER INFORMATION: Description of Unknown: Toxic gluten
      oligopeptide derived during human digestion of
      gliadins and related storage proteins

<400> SEQUENCE: 16

Pro Phe Ser Gln Gln Gln Gln Pro Val
1               5

<210> SEQ ID NO 17
<211> LENGTH: 33
<212> TYPE: PRT
<213> ORGANISM: Unknown
<220> FEATURE:
<223> OTHER INFORMATION: Description of Unknown: Gliadin fragment
      peptide

<400> SEQUENCE: 17

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 18
<211> LENGTH: 25
<212> TYPE: PRT
<213> ORGANISM: Unknown
<220> FEATURE:
<223> OTHER INFORMATION: Description of Unknown: Gliadin fragment
      peptide

<400> SEQUENCE: 18

Leu Gln Leu Gln Pro Phe Pro Gln Pro Gln Leu Pro Tyr Pro Gln Pro
1               5                   10                  15

Gln Leu Pro Tyr Pro Gln Pro Gln Leu
            20                  25

<210> SEQ ID NO 19
<211> LENGTH: 22
<212> TYPE: PRT
<213> ORGANISM: Unknown
<220> FEATURE:
<223> OTHER INFORMATION: Description of Unknown: Gliadin fragment
      peptide

<400> SEQUENCE: 19

Leu Gln Leu Gln Pro Phe Pro Gln Pro Gln Leu Pro Tyr Pro Gln Pro
1               5                   10                  15

Gln Leu Pro Tyr Pro Gln
            20

<210> SEQ ID NO 20
<211> LENGTH: 18
<212> TYPE: PRT
<213> ORGANISM: Unknown
<220> FEATURE:
<223> OTHER INFORMATION: Description of Unknown: Gliadin fragment
      peptide
```

```
<400> SEQUENCE: 20

Leu Gln Leu Gln Pro Phe Pro Gln Pro Gln Leu Pro Tyr Pro Gln Pro
1               5                   10                  15

Gln Leu

<210> SEQ ID NO 21
<211> LENGTH: 15
<212> TYPE: PRT
<213> ORGANISM: Unknown
<220> FEATURE:
<223> OTHER INFORMATION: Description of Unknown: Gliadin fragment
      peptide

<400> SEQUENCE: 21

Leu Gln Leu Gln Pro Phe Pro Gln Pro Gln Leu Pro Tyr Pro Gln
1               5                   10                  15

<210> SEQ ID NO 22
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 22

Leu Gln Leu Gln Pro Phe Pro Gln Pro Gln Leu Pro Tyr Pro
1               5                   10

<210> SEQ ID NO 23
<211> LENGTH: 13
<212> TYPE: PRT
<213> ORGANISM: Unknown
<220> FEATURE:
<223> OTHER INFORMATION: Description of Unknown: Gliadin fragment
      peptide

<400> SEQUENCE: 23

Leu Gln Leu Gln Pro Phe Pro Gln Pro Gln Leu Pro Tyr
1               5                   10

<210> SEQ ID NO 24
<211> LENGTH: 12
<212> TYPE: PRT
<213> ORGANISM: Unknown
<220> FEATURE:
<223> OTHER INFORMATION: Description of Unknown: Gliadin fragment
      peptide

<400> SEQUENCE: 24

Leu Gln Leu Gln Pro Phe Pro Gln Pro Gln Leu Pro
1               5                   10

<210> SEQ ID NO 25
<211> LENGTH: 11
<212> TYPE: PRT
<213> ORGANISM: Unknown
<220> FEATURE:
<223> OTHER INFORMATION: Description of Unknown: Gliadin fragment
      peptide

<400> SEQUENCE: 25

Leu Gln Leu Gln Pro Phe Pro Gln Pro Gln Leu
1               5                   10

<210> SEQ ID NO 26
```

```
<211> LENGTH: 10
<212> TYPE: PRT
<213> ORGANISM: Unknown
<220> FEATURE:
<223> OTHER INFORMATION: Description of Unknown: Gliadin fragment
      peptide

<400> SEQUENCE: 26

Leu Gln Leu Gln Pro Phe Pro Gln Pro Gln
1               5                   10

<210> SEQ ID NO 27
<211> LENGTH: 9
<212> TYPE: PRT
<213> ORGANISM: Unknown
<220> FEATURE:
<223> OTHER INFORMATION: Description of Unknown: Gliadin fragment
      peptide

<400> SEQUENCE: 27

Leu Gln Leu Gln Pro Phe Pro Gln Pro
1               5

<210> SEQ ID NO 28
<211> LENGTH: 7
<212> TYPE: PRT
<213> ORGANISM: Unknown
<220> FEATURE:
<223> OTHER INFORMATION: Description of Unknown: Gliadin fragment
      peptide

<400> SEQUENCE: 28

Tyr Pro Gln Pro Gln Pro Phe
1               5

<210> SEQ ID NO 29
<211> LENGTH: 8
<212> TYPE: PRT
<213> ORGANISM: Unknown
<220> FEATURE:
<223> OTHER INFORMATION: Description of Unknown: Gliadin fragment
      peptide

<400> SEQUENCE: 29

Pro Tyr Pro Gln Pro Gln Pro Phe
1               5

<210> SEQ ID NO 30
<211> LENGTH: 9
<212> TYPE: PRT
<213> ORGANISM: Unknown
<220> FEATURE:
<223> OTHER INFORMATION: Description of Unknown: Gliadin fragment
      peptide

<400> SEQUENCE: 30

Leu Pro Tyr Pro Gln Pro Gln Pro Phe
1               5

<210> SEQ ID NO 31
<211> LENGTH: 11
<212> TYPE: PRT
<213> ORGANISM: Unknown
<220> FEATURE:
<223> OTHER INFORMATION: Description of Unknown: Gliadin fragment
      peptide

<400> SEQUENCE: 31
```

Pro Gln Leu Pro Tyr Pro Gln Pro Gln Pro Phe
1               5                   10

<210> SEQ ID NO 32
<211> LENGTH: 12
<212> TYPE: PRT
<213> ORGANISM: Unknown
<220> FEATURE:
<223> OTHER INFORMATION: Description of Unknown: Gliadin fragment
      peptide

<400> SEQUENCE: 32

Gln Pro Gln Leu Pro Tyr Pro Gln Pro Gln Pro Phe
1               5                   10

<210> SEQ ID NO 33
<211> LENGTH: 13
<212> TYPE: PRT
<213> ORGANISM: Unknown
<220> FEATURE:
<223> OTHER INFORMATION: Description of Unknown: Gliadin fragment
      peptide

<400> SEQUENCE: 33

Pro Gln Pro Gln Leu Pro Tyr Pro Gln Pro Gln Pro Phe
1               5                   10

<210> SEQ ID NO 34
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 34

Tyr Pro Gln Pro Gln Leu Pro Tyr Pro Gln Pro Gln Pro Phe
1               5                   10

<210> SEQ ID NO 35
<211> LENGTH: 15
<212> TYPE: PRT
<213> ORGANISM: Unknown
<220> FEATURE:
<223> OTHER INFORMATION: Description of Unknown: Gliadin fragment
      peptide

<400> SEQUENCE: 35

Pro Tyr Pro Gln Pro Gln Leu Pro Tyr Pro Gln Pro Gln Pro Phe
1               5                   10                  15

<210> SEQ ID NO 36
<211> LENGTH: 16
<212> TYPE: PRT
<213> ORGANISM: Unknown
<220> FEATURE:
<223> OTHER INFORMATION: Description of Unknown: Gliadin fragment
      peptide

<400> SEQUENCE: 36

Leu Pro Tyr Pro Gln Pro Gln Leu Pro Tyr Pro Gln Pro Gln Pro Phe
1               5                   10                  15

<210> SEQ ID NO 37
<211> LENGTH: 17
<212> TYPE: PRT
<213> ORGANISM: Unknown
<220> FEATURE:

```
<223> OTHER INFORMATION: Description of Unknown: Gliadin fragment
      peptide

<400> SEQUENCE: 37

Gln Leu Pro Tyr Pro Gln Pro Gln Leu Pro Tyr Pro Gln Pro Gln Pro
1               5                   10                  15

Phe

<210> SEQ ID NO 38
<211> LENGTH: 18
<212> TYPE: PRT
<213> ORGANISM: Unknown
<220> FEATURE:
<223> OTHER INFORMATION: Description of Unknown: Gliadin fragment
      peptide

<400> SEQUENCE: 38

Pro Gln Leu Pro Tyr Pro Gln Pro Gln Leu Pro Tyr Pro Gln Pro Gln
1               5                   10                  15

Pro Phe

<210> SEQ ID NO 39
<211> LENGTH: 20
<212> TYPE: PRT
<213> ORGANISM: Unknown
<220> FEATURE:
<223> OTHER INFORMATION: Description of Unknown: Gliadin fragment
      peptide

<400> SEQUENCE: 39

Pro Gln Pro Gln Leu Pro Tyr Pro Gln Pro Gln Leu Pro Tyr Pro Gln
1               5                   10                  15

Pro Gln Pro Phe
            20

<210> SEQ ID NO 40
<211> LENGTH: 21
<212> TYPE: PRT
<213> ORGANISM: Unknown
<220> FEATURE:
<223> OTHER INFORMATION: Description of Unknown: Gliadin fragment
      peptide

<400> SEQUENCE: 40

Tyr Pro Gln Pro Gln Leu Pro Tyr Pro Gln Pro Gln Leu Pro Tyr Pro
1               5                   10                  15

Gln Pro Gln Pro Phe
            20

<210> SEQ ID NO 41
<211> LENGTH: 22
<212> TYPE: PRT
<213> ORGANISM: Unknown
<220> FEATURE:
<223> OTHER INFORMATION: Description of Unknown: Gliadin fragment
      peptide

<400> SEQUENCE: 41

Pro Tyr Pro Gln Pro Gln Leu Pro Tyr Pro Gln Pro Gln Leu Pro Tyr
1               5                   10                  15

Pro Gln Pro Gln Pro Phe
            20

<210> SEQ ID NO 42
```

```
<211> LENGTH: 23
<212> TYPE: PRT
<213> ORGANISM: Unknown
<220> FEATURE:
<223> OTHER INFORMATION: Description of Unknown: Gliadin fragment
      peptide

<400> SEQUENCE: 42

Leu Pro Tyr Pro Gln Pro Gln Leu Pro Tyr Pro Gln Pro Gln Leu Pro
1               5                   10                  15

Tyr Pro Gln Pro Gln Pro Phe
            20

<210> SEQ ID NO 43
<211> LENGTH: 25
<212> TYPE: PRT
<213> ORGANISM: Unknown
<220> FEATURE:
<223> OTHER INFORMATION: Description of Unknown: Gliadin fragment
      peptide

<400> SEQUENCE: 43

Pro Gln Leu Pro Tyr Pro Gln Pro Gln Leu Pro Tyr Pro Gln Pro Gln
1               5                   10                  15

Leu Pro Tyr Pro Gln Pro Gln Pro Phe
            20                  25

<210> SEQ ID NO 44
<211> LENGTH: 27
<212> TYPE: PRT
<213> ORGANISM: Unknown
<220> FEATURE:
<223> OTHER INFORMATION: Description of Unknown: Gliadin fragment
      peptide

<400> SEQUENCE: 44

Pro Gln Pro Gln Leu Pro Tyr Pro Gln Pro Gln Leu Pro Tyr Pro Gln
1               5                   10                  15

Pro Gln Leu Pro Tyr Pro Gln Pro Gln Pro Phe
            20                  25

<210> SEQ ID NO 45
<211> LENGTH: 28
<212> TYPE: PRT
<213> ORGANISM: Unknown
<220> FEATURE:
<223> OTHER INFORMATION: Description of Unknown: Gliadin fragment
      peptide

<400> SEQUENCE: 45

Phe Pro Gln Pro Gln Leu Pro Tyr Pro Gln Pro Gln Leu Pro Tyr Pro
1               5                   10                  15

Gln Pro Gln Leu Pro Tyr Pro Gln Pro Gln Pro Phe
            20                  25

<210> SEQ ID NO 46
<211> LENGTH: 29
<212> TYPE: PRT
<213> ORGANISM: Unknown
<220> FEATURE:
<223> OTHER INFORMATION: Description of Unknown: Gliadin fragment
      peptide

<400> SEQUENCE: 46

Pro Phe Pro Gln Pro Gln Leu Pro Tyr Pro Gln Pro Gln Leu Pro Tyr
1               5                   10                  15
```

```
Pro Gln Pro Gln Leu Pro Tyr Pro Gln Pro Gln Pro Phe
            20                  25
```

<210> SEQ ID NO 47
<211> LENGTH: 30
<212> TYPE: PRT
<213> ORGANISM: Unknown
<220> FEATURE:
<223> OTHER INFORMATION: Description of Unknown: Gliadin fragment
      peptide

<400> SEQUENCE: 47

```
Gln Pro Phe Pro Gln Pro Gln Leu Pro Tyr Pro Gln Pro Gln Leu Pro
1               5                   10                  15

Tyr Pro Gln Pro Gln Leu Pro Tyr Pro Gln Pro Gln Pro Phe
            20                  25                  30
```

<210> SEQ ID NO 48
<211> LENGTH: 31
<212> TYPE: PRT
<213> ORGANISM: Unknown
<220> FEATURE:
<223> OTHER INFORMATION: Description of Unknown: Gliadin fragment
      peptide

<400> SEQUENCE: 48

```
Leu Gln Pro Phe Pro Gln Pro Gln Leu Pro Tyr Pro Gln Pro Gln Leu
1               5                   10                  15

Pro Tyr Pro Gln Pro Gln Leu Pro Tyr Pro Gln Pro Gln Pro Phe
            20                  25                  30
```

<210> SEQ ID NO 49
<211> LENGTH: 32
<212> TYPE: PRT
<213> ORGANISM: Unknown
<220> FEATURE:
<223> OTHER INFORMATION: Description of Unknown: Gliadin fragment
      peptide

<400> SEQUENCE: 49

```
Gln Leu Gln Pro Phe Pro Gln Pro Gln Leu Pro Tyr Pro Gln Pro Gln
1               5                   10                  15

Leu Pro Tyr Pro Gln Pro Gln Leu Pro Tyr Pro Gln Pro Gln Pro Phe
            20                  25                  30
```

<210> SEQ ID NO 50
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 50

```
Phe Pro Gln Pro Gln Leu Pro Tyr Pro Gln Pro Gln Leu Pro
1               5                   10
```

<210> SEQ ID NO 51
<211> LENGTH: 17
<212> TYPE: PRT
<213> ORGANISM: Unknown
<220> FEATURE:
<223> OTHER INFORMATION: Description of Unknown: Gliadin fragment
      peptide

<400> SEQUENCE: 51

Gln Pro Gln Leu Pro Tyr Pro Gln Pro Leu Pro Tyr Pro Gln Pro
1               5                   10                  15

Gln

<210> SEQ ID NO 52
<211> LENGTH: 18
<212> TYPE: PRT
<213> ORGANISM: Unknown
<220> FEATURE:
<223> OTHER INFORMATION: Description of Unknown: Gliadin fragment
      peptide

<400> SEQUENCE: 52

Gln Pro Gln Leu Pro Tyr Pro Gln Pro Leu Pro Tyr Pro Gln Pro
1               5                   10                  15

Gln Leu

<210> SEQ ID NO 53
<211> LENGTH: 20
<212> TYPE: PRT
<213> ORGANISM: Unknown
<220> FEATURE:
<223> OTHER INFORMATION: Description of Unknown: Gliadin fragment
      peptide

<400> SEQUENCE: 53

Gln Pro Gln Leu Pro Tyr Pro Gln Pro Leu Pro Tyr Pro Gln Pro
1               5                   10                  15

Gln Leu Pro Tyr
            20

<210> SEQ ID NO 54
<211> LENGTH: 21
<212> TYPE: PRT
<213> ORGANISM: Unknown
<220> FEATURE:
<223> OTHER INFORMATION: Description of Unknown: Gliadin fragment
      peptide

<400> SEQUENCE: 54

Gln Pro Gln Leu Pro Tyr Pro Gln Pro Leu Pro Tyr Pro Gln Pro
1               5                   10                  15

Gln Leu Pro Tyr Pro
            20

<210> SEQ ID NO 55
<211> LENGTH: 22
<212> TYPE: PRT
<213> ORGANISM: Unknown
<220> FEATURE:
<223> OTHER INFORMATION: Description of Unknown: Gliadin fragment
      peptide

<400> SEQUENCE: 55

Gln Pro Gln Leu Pro Tyr Pro Gln Pro Leu Pro Tyr Pro Gln Pro
1               5                   10                  15

Gln Leu Pro Tyr Pro Gln
            20

<210> SEQ ID NO 56
<211> LENGTH: 25
<212> TYPE: PRT
<213> ORGANISM: Unknown
<220> FEATURE:

-continued

<223> OTHER INFORMATION: Description of Unknown: Gliadin fragment
      peptide

<400> SEQUENCE: 56

Gln Pro Gln Leu Pro Tyr Pro Gln Pro Gln Leu Pro Tyr Pro Gln Pro
1               5                   10                  15

Gln Leu Pro Tyr Pro Gln Pro Gln Pro
            20                  25

<210> SEQ ID NO 57
<211> LENGTH: 20
<212> TYPE: PRT
<213> ORGANISM: Unknown
<220> FEATURE:
<223> OTHER INFORMATION: Description of Unknown: Gliadin fragment
      peptide

<400> SEQUENCE: 57

Pro Gln Leu Pro Tyr Pro Gln Pro Gln Leu Pro Tyr Pro Gln Pro Gln
1               5                   10                  15

Leu Pro Tyr Pro
            20

<210> SEQ ID NO 58
<211> LENGTH: 21
<212> TYPE: PRT
<213> ORGANISM: Unknown
<220> FEATURE:
<223> OTHER INFORMATION: Description of Unknown: Gliadin fragment
      peptide

<400> SEQUENCE: 58

Gln Leu Pro Tyr Pro Gln Pro Gln Leu Pro Tyr Pro Gln Pro Gln Leu
1               5                   10                  15

Pro Tyr Pro Gln Pro
            20

<210> SEQ ID NO 59
<211> LENGTH: 18
<212> TYPE: PRT
<213> ORGANISM: Unknown
<220> FEATURE:
<223> OTHER INFORMATION: Description of Unknown: Gliadin fragment
      peptide

<400> SEQUENCE: 59

Leu Pro Tyr Pro Gln Pro Gln Leu Pro Tyr Pro Gln Pro Gln Leu Pro
1               5                   10                  15

Tyr Pro

<210> SEQ ID NO 60
<211> LENGTH: 20
<212> TYPE: PRT
<213> ORGANISM: Unknown
<220> FEATURE:
<223> OTHER INFORMATION: Description of Unknown: Gliadin fragment
      peptide

<400> SEQUENCE: 60

Leu Pro Tyr Pro Gln Pro Gln Leu Pro Tyr Pro Gln Pro Gln Leu Pro
1               5                   10                  15

Tyr Pro Gln Pro
            20

```
<210> SEQ ID NO 61
<211> LENGTH: 15
<212> TYPE: PRT
<213> ORGANISM: Unknown
<220> FEATURE:
<223> OTHER INFORMATION: Description of Unknown: Gliadin fragment
      peptide

<400> SEQUENCE: 61

Pro Tyr Pro Gln Pro Gln Leu Pro Tyr Pro Gln Pro Gln Leu Pro
1               5                  10                  15

<210> SEQ ID NO 62
<211> LENGTH: 17
<212> TYPE: PRT
<213> ORGANISM: Unknown
<220> FEATURE:
<223> OTHER INFORMATION: Description of Unknown: Gliadin fragment
      peptide

<400> SEQUENCE: 62

Gln Pro Gln Leu Pro Tyr Pro Gln Pro Gln Leu Pro Tyr Pro Gln Pro
1               5                  10                  15

Gln

<210> SEQ ID NO 63
<211> LENGTH: 26
<212> TYPE: PRT
<213> ORGANISM: Unknown
<220> FEATURE:
<223> OTHER INFORMATION: Description of Unknown: Gliadin fragment
      peptide

<400> SEQUENCE: 63

Phe Leu Gln Pro Gln Gln Pro Phe Pro Gln Gln Pro Gln Gln Pro Tyr
1               5                  10                  15

Pro Gln Gln Pro Gln Gln Pro Phe Pro Gln
            20                  25

<210> SEQ ID NO 64
<211> LENGTH: 25
<212> TYPE: PRT
<213> ORGANISM: Unknown
<220> FEATURE:
<223> OTHER INFORMATION: Description of Unknown: Gliadin fragment
      peptide

<400> SEQUENCE: 64

Phe Leu Gln Pro Gln Gln Pro Phe Pro Gln Gln Pro Gln Gln Pro Tyr
1               5                  10                  15

Pro Gln Gln Pro Gln Gln Pro Phe Pro
            20                  25

<210> SEQ ID NO 65
<211> LENGTH: 23
<212> TYPE: PRT
<213> ORGANISM: Unknown
<220> FEATURE:
<223> OTHER INFORMATION: Description of Unknown: Gliadin fragment
      peptide

<400> SEQUENCE: 65

Phe Leu Gln Pro Gln Gln Pro Phe Pro Gln Gln Pro Gln Gln Pro Tyr
1               5                  10                  15

Pro Gln Gln Pro Gln Gln Pro
            20
```

<210> SEQ ID NO 66
<211> LENGTH: 22
<212> TYPE: PRT
<213> ORGANISM: Unknown
<220> FEATURE:
<223> OTHER INFORMATION: Description of Unknown: Gliadin fragment
      peptide

<400> SEQUENCE: 66

Phe Leu Gln Pro Gln Gln Pro Phe Pro Gln Gln Pro Gln Gln Pro Tyr
1               5                   10                  15

Pro Gln Gln Pro Gln Gln
            20

<210> SEQ ID NO 67
<211> LENGTH: 21
<212> TYPE: PRT
<213> ORGANISM: Unknown
<220> FEATURE:
<223> OTHER INFORMATION: Description of Unknown: Gliadin fragment
      peptide

<400> SEQUENCE: 67

Phe Leu Gln Pro Gln Gln Pro Phe Pro Gln Gln Pro Gln Gln Pro Tyr
1               5                   10                  15

Pro Gln Gln Pro Gln
            20

<210> SEQ ID NO 68
<211> LENGTH: 20
<212> TYPE: PRT
<213> ORGANISM: Unknown
<220> FEATURE:
<223> OTHER INFORMATION: Description of Unknown: Gliadin fragment
      peptide

<400> SEQUENCE: 68

Phe Leu Gln Pro Gln Gln Pro Phe Pro Gln Gln Pro Gln Gln Pro Tyr
1               5                   10                  15

Pro Gln Gln Pro
            20

<210> SEQ ID NO 69
<211> LENGTH: 19
<212> TYPE: PRT
<213> ORGANISM: Unknown
<220> FEATURE:
<223> OTHER INFORMATION: Description of Unknown: Gliadin fragment
      peptide

<400> SEQUENCE: 69

Phe Leu Gln Pro Gln Gln Pro Phe Pro Gln Gln Pro Gln Gln Pro Tyr
1               5                   10                  15

Pro Gln Gln

<210> SEQ ID NO 70
<211> LENGTH: 18
<212> TYPE: PRT
<213> ORGANISM: Unknown
<220> FEATURE:
<223> OTHER INFORMATION: Description of Unknown: Gliadin fragment
      peptide

<400> SEQUENCE: 70

Phe Leu Gln Pro Gln Gln Pro Phe Pro Gln Pro Gln Gln Pro Tyr
1               5                   10                  15
Pro Gln

<210> SEQ ID NO 71
<211> LENGTH: 17
<212> TYPE: PRT
<213> ORGANISM: Unknown
<220> FEATURE:
<223> OTHER INFORMATION: Description of Unknown: Gliadin fragment
      peptide

<400> SEQUENCE: 71

Phe Leu Gln Pro Gln Gln Pro Phe Pro Gln Pro Gln Gln Pro Tyr
1               5                   10                  15
Pro

<210> SEQ ID NO 72
<211> LENGTH: 16
<212> TYPE: PRT
<213> ORGANISM: Unknown
<220> FEATURE:
<223> OTHER INFORMATION: Description of Unknown: Gliadin fragment
      peptide

<400> SEQUENCE: 72

Phe Leu Gln Pro Gln Gln Pro Phe Pro Gln Pro Gln Gln Pro Tyr
1               5                   10                  15

<210> SEQ ID NO 73
<211> LENGTH: 15
<212> TYPE: PRT
<213> ORGANISM: Unknown
<220> FEATURE:
<223> OTHER INFORMATION: Description of Unknown: Gliadin fragment
      peptide

<400> SEQUENCE: 73

Phe Leu Gln Pro Gln Gln Pro Phe Pro Gln Pro Gln Gln Pro
1               5                   10                  15

<210> SEQ ID NO 74
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 74

Phe Leu Gln Pro Gln Gln Pro Phe Pro Gln Pro Gln Gln
1               5                   10

<210> SEQ ID NO 75
<211> LENGTH: 13
<212> TYPE: PRT
<213> ORGANISM: Unknown
<220> FEATURE:
<223> OTHER INFORMATION: Description of Unknown: Gliadin fragment
      peptide

<400> SEQUENCE: 75

Phe Leu Gln Pro Gln Gln Pro Phe Pro Gln Pro Gln
1               5                   10

<210> SEQ ID NO 76

```
<211> LENGTH: 12
<212> TYPE: PRT
<213> ORGANISM: Unknown
<220> FEATURE:
<223> OTHER INFORMATION: Description of Unknown: Gliadin fragment
      peptide

<400> SEQUENCE: 76

Phe Leu Gln Pro Gln Gln Pro Phe Pro Gln Gln Pro
1               5                   10

<210> SEQ ID NO 77
<211> LENGTH: 11
<212> TYPE: PRT
<213> ORGANISM: Unknown
<220> FEATURE:
<223> OTHER INFORMATION: Description of Unknown: Gliadin fragment
      peptide

<400> SEQUENCE: 77

Phe Leu Gln Pro Gln Gln Pro Phe Pro Gln Gln
1               5                   10

<210> SEQ ID NO 78
<211> LENGTH: 10
<212> TYPE: PRT
<213> ORGANISM: Unknown
<220> FEATURE:
<223> OTHER INFORMATION: Description of Unknown: Gliadin fragment
      peptide

<400> SEQUENCE: 78

Phe Leu Gln Pro Gln Gln Pro Phe Pro Gln
1               5                   10

<210> SEQ ID NO 79
<211> LENGTH: 9
<212> TYPE: PRT
<213> ORGANISM: Unknown
<220> FEATURE:
<223> OTHER INFORMATION: Description of Unknown: Gliadin fragment
      peptide

<400> SEQUENCE: 79

Phe Leu Gln Pro Gln Gln Pro Phe Pro
1               5

<210> SEQ ID NO 80
<211> LENGTH: 8
<212> TYPE: PRT
<213> ORGANISM: Unknown
<220> FEATURE:
<223> OTHER INFORMATION: Description of Unknown: Gliadin fragment
      peptide

<400> SEQUENCE: 80

Phe Leu Gln Pro Gln Gln Pro Phe
1               5

<210> SEQ ID NO 81
<211> LENGTH: 10
<212> TYPE: PRT
<213> ORGANISM: Unknown
<220> FEATURE:
<223> OTHER INFORMATION: Description of Unknown: Gliadin fragment
      peptide

<400> SEQUENCE: 81
```

```
Pro Gln Gln Pro Gln Gln Pro Phe Pro Gln
1               5                   10
```

<210> SEQ ID NO 82
<211> LENGTH: 11
<212> TYPE: PRT
<213> ORGANISM: Unknown
<220> FEATURE:
<223> OTHER INFORMATION: Description of Unknown: Gliadin fragment
      peptide

<400> SEQUENCE: 82

```
Tyr Pro Gln Gln Pro Gln Gln Pro Phe Pro Gln
1               5                   10
```

<210> SEQ ID NO 83
<211> LENGTH: 12
<212> TYPE: PRT
<213> ORGANISM: Unknown
<220> FEATURE:
<223> OTHER INFORMATION: Description of Unknown: Gliadin fragment
      peptide

<400> SEQUENCE: 83

```
Pro Tyr Pro Gln Gln Pro Gln Gln Pro Phe Pro Gln
1               5                   10
```

<210> SEQ ID NO 84
<211> LENGTH: 13
<212> TYPE: PRT
<213> ORGANISM: Unknown
<220> FEATURE:
<223> OTHER INFORMATION: Description of Unknown: Gliadin fragment
      peptide

<400> SEQUENCE: 84

```
Gln Pro Tyr Pro Gln Gln Pro Gln Gln Pro Phe Pro Gln
1               5                   10
```

<210> SEQ ID NO 85
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 85

```
Gln Gln Pro Tyr Pro Gln Gln Pro Gln Gln Pro Phe Pro Gln
1               5                   10
```

<210> SEQ ID NO 86
<211> LENGTH: 15
<212> TYPE: PRT
<213> ORGANISM: Unknown
<220> FEATURE:
<223> OTHER INFORMATION: Description of Unknown: Gliadin fragment
      peptide

<400> SEQUENCE: 86

```
Pro Gln Gln Pro Tyr Pro Gln Gln Pro Gln Gln Pro Phe Pro Gln
1               5                   10                  15
```

<210> SEQ ID NO 87
<211> LENGTH: 16
<212> TYPE: PRT
<213> ORGANISM: Unknown
<220> FEATURE:

<223> OTHER INFORMATION: Description of Unknown: Gliadin fragment
      peptide

<400> SEQUENCE: 87

Gln Pro Gln Gln Pro Tyr Pro Gln Gln Pro Gln Gln Pro Phe Pro Gln
1               5                   10                  15

<210> SEQ ID NO 88
<211> LENGTH: 17
<212> TYPE: PRT
<213> ORGANISM: Unknown
<220> FEATURE:
<223> OTHER INFORMATION: Description of Unknown: Gliadin fragment
      peptide

<400> SEQUENCE: 88

Gln Gln Pro Gln Gln Pro Tyr Pro Gln Gln Pro Gln Gln Pro Phe Pro
1               5                   10                  15

Gln

<210> SEQ ID NO 89
<211> LENGTH: 18
<212> TYPE: PRT
<213> ORGANISM: Unknown
<220> FEATURE:
<223> OTHER INFORMATION: Description of Unknown: Gliadin fragment
      peptide

<400> SEQUENCE: 89

Pro Gln Gln Pro Gln Gln Pro Tyr Pro Gln Gln Pro Gln Gln Pro Phe
1               5                   10                  15

Pro Gln

<210> SEQ ID NO 90
<211> LENGTH: 19
<212> TYPE: PRT
<213> ORGANISM: Unknown
<220> FEATURE:
<223> OTHER INFORMATION: Description of Unknown: Gliadin fragment
      peptide

<400> SEQUENCE: 90

Phe Pro Gln Gln Pro Gln Gln Pro Tyr Pro Gln Gln Pro Gln Gln Pro
1               5                   10                  15

Phe Pro Gln

<210> SEQ ID NO 91
<211> LENGTH: 20
<212> TYPE: PRT
<213> ORGANISM: Unknown
<220> FEATURE:
<223> OTHER INFORMATION: Description of Unknown: Gliadin fragment
      peptide

<400> SEQUENCE: 91

Pro Phe Pro Gln Gln Pro Gln Gln Pro Tyr Pro Gln Gln Pro Gln Gln
1               5                   10                  15

Pro Phe Pro Gln
            20

<210> SEQ ID NO 92
<211> LENGTH: 21
<212> TYPE: PRT
<213> ORGANISM: Unknown
<220> FEATURE:

-continued

```
<223> OTHER INFORMATION: Description of Unknown: Gliadin fragment
      peptide

<400> SEQUENCE: 92

Gln Pro Phe Pro Gln Gln Pro Gln Gln Pro Tyr Pro Gln Gln Pro Gln
1               5                   10                  15

Gln Pro Phe Pro Gln
            20

<210> SEQ ID NO 93
<211> LENGTH: 22
<212> TYPE: PRT
<213> ORGANISM: Unknown
<220> FEATURE:
<223> OTHER INFORMATION: Description of Unknown: Gliadin fragment
      peptide

<400> SEQUENCE: 93

Gln Gln Pro Phe Pro Gln Gln Pro Gln Gln Pro Tyr Pro Gln Gln Pro
1               5                   10                  15

Gln Gln Pro Phe Pro Gln
            20

<210> SEQ ID NO 94
<211> LENGTH: 24
<212> TYPE: PRT
<213> ORGANISM: Unknown
<220> FEATURE:
<223> OTHER INFORMATION: Description of Unknown: Gliadin fragment
      peptide

<400> SEQUENCE: 94

Gln Pro Gln Gln Pro Phe Pro Gln Gln Pro Gln Gln Pro Tyr Pro Gln
1               5                   10                  15

Gln Pro Gln Gln Pro Phe Pro Gln
            20

<210> SEQ ID NO 95
<211> LENGTH: 25
<212> TYPE: PRT
<213> ORGANISM: Unknown
<220> FEATURE:
<223> OTHER INFORMATION: Description of Unknown: Gliadin fragment
      peptide

<400> SEQUENCE: 95

Leu Gln Pro Gln Gln Pro Phe Pro Gln Gln Pro Gln Gln Pro Tyr Pro
1               5                   10                  15

Gln Gln Pro Gln Gln Pro Phe Pro Gln
            20                  25

<210> SEQ ID NO 96
<211> LENGTH: 9
<212> TYPE: PRT
<213> ORGANISM: Unknown
<220> FEATURE:
<223> OTHER INFORMATION: Description of Unknown: Gliadin fragment
      peptide

<400> SEQUENCE: 96

Leu Gln Pro Gln Gln Pro Phe Pro Gln
1               5

<210> SEQ ID NO 97
<211> LENGTH: 11
```

```
<212> TYPE: PRT
<213> ORGANISM: Unknown
<220> FEATURE:
<223> OTHER INFORMATION: Description of Unknown: Gliadin fragment
      peptide

<400> SEQUENCE: 97

Leu Gln Pro Gln Gln Pro Phe Pro Gln Gln Pro
1               5                   10

<210> SEQ ID NO 98
<211> LENGTH: 13
<212> TYPE: PRT
<213> ORGANISM: Unknown
<220> FEATURE:
<223> OTHER INFORMATION: Description of Unknown: Gliadin fragment
      peptide

<400> SEQUENCE: 98

Leu Gln Pro Gln Gln Pro Phe Pro Gln Gln Pro Gln Gln
1               5                   10

<210> SEQ ID NO 99
<211> LENGTH: 16
<212> TYPE: PRT
<213> ORGANISM: Unknown
<220> FEATURE:
<223> OTHER INFORMATION: Description of Unknown: Gliadin fragment
      peptide

<400> SEQUENCE: 99

Leu Gln Pro Gln Gln Pro Phe Pro Gln Gln Pro Gln Gln Pro Tyr Pro
1               5                   10                  15

<210> SEQ ID NO 100
<211> LENGTH: 17
<212> TYPE: PRT
<213> ORGANISM: Unknown
<220> FEATURE:
<223> OTHER INFORMATION: Description of Unknown: Gliadin fragment
      peptide

<400> SEQUENCE: 100

Leu Gln Pro Gln Gln Pro Phe Pro Gln Gln Pro Gln Gln Pro Tyr Pro
1               5                   10                  15

Gln

<210> SEQ ID NO 101
<211> LENGTH: 18
<212> TYPE: PRT
<213> ORGANISM: Unknown
<220> FEATURE:
<223> OTHER INFORMATION: Description of Unknown: Gliadin fragment
      peptide

<400> SEQUENCE: 101

Leu Gln Pro Gln Gln Pro Phe Pro Gln Gln Pro Gln Gln Pro Tyr Pro
1               5                   10                  15

Gln Gln

<210> SEQ ID NO 102
<211> LENGTH: 20
<212> TYPE: PRT
<213> ORGANISM: Unknown
<220> FEATURE:
<223> OTHER INFORMATION: Description of Unknown: Gliadin fragment
      peptide
```

<400> SEQUENCE: 102

Leu Gln Pro Gln Gln Pro Phe Pro Gln Gln Pro Gln Gln Pro Tyr Pro
1               5                   10                  15
Gln Gln Pro Gln
            20

<210> SEQ ID NO 103
<211> LENGTH: 16
<212> TYPE: PRT
<213> ORGANISM: Unknown
<220> FEATURE:
<223> OTHER INFORMATION: Description of Unknown: Gliadin fragment
      peptide

<400> SEQUENCE: 103

Gln Pro Gln Gln Pro Phe Pro Gln Gln Pro Gln Gln Pro Tyr Pro Gln
1               5                   10                  15

<210> SEQ ID NO 104
<211> LENGTH: 7
<212> TYPE: PRT
<213> ORGANISM: Unknown
<220> FEATURE:
<223> OTHER INFORMATION: Description of Unknown: Gliadin fragment
      peptide

<400> SEQUENCE: 104

Pro Gln Gln Pro Phe Pro Gln
1               5

<210> SEQ ID NO 105
<211> LENGTH: 13
<212> TYPE: PRT
<213> ORGANISM: Unknown
<220> FEATURE:
<223> OTHER INFORMATION: Description of Unknown: Gliadin fragment
      peptide

<400> SEQUENCE: 105

Gln Pro Phe Pro Gln Gln Pro Gln Gln Pro Tyr Pro Gln
1               5                   10

<210> SEQ ID NO 106
<211> LENGTH: 12
<212> TYPE: PRT
<213> ORGANISM: Unknown
<220> FEATURE:
<223> OTHER INFORMATION: Description of Unknown: Gliadin fragment
      peptide

<400> SEQUENCE: 106

Pro Phe Pro Gln Gln Pro Gln Gln Pro Tyr Pro Gln
1               5                   10

<210> SEQ ID NO 107
<211> LENGTH: 10
<212> TYPE: PRT
<213> ORGANISM: Unknown
<220> FEATURE:
<223> OTHER INFORMATION: Description of Unknown: Gliadin fragment
      peptide

<400> SEQUENCE: 107

Phe Pro Gln Gln Pro Gln Gln Pro Tyr Pro
1               5                   10

```
<210> SEQ ID NO 108
<211> LENGTH: 11
<212> TYPE: PRT
<213> ORGANISM: Unknown
<220> FEATURE:
<223> OTHER INFORMATION: Description of Unknown: Gliadin fragment
      peptide

<400> SEQUENCE: 108

Phe Pro Gln Gln Pro Gln Gln Pro Tyr Pro Gln
1               5                   10

<210> SEQ ID NO 109
<211> LENGTH: 13
<212> TYPE: PRT
<213> ORGANISM: Unknown
<220> FEATURE:
<223> OTHER INFORMATION: Description of Unknown: Gliadin fragment
      peptide

<400> SEQUENCE: 109

Phe Pro Gln Gln Pro Gln Gln Pro Tyr Pro Gln Gln Pro
1               5                   10

<210> SEQ ID NO 110
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 110

Phe Pro Gln Gln Pro Gln Gln Pro Tyr Pro Gln Gln Pro Gln
1               5                   10

<210> SEQ ID NO 111
<211> LENGTH: 12
<212> TYPE: PRT
<213> ORGANISM: Unknown
<220> FEATURE:
<223> OTHER INFORMATION: Description of Unknown: Gliadin fragment
      peptide

<400> SEQUENCE: 111

Gln Gln Pro Gln Gln Pro Tyr Pro Gln Gln Pro Gln
1               5                   10

<210> SEQ ID NO 112
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 112

Pro Gln Gln Pro Tyr Pro Gln Gln Pro Gln Gln Pro Phe Pro
1               5                   10

<210> SEQ ID NO 113
<211> LENGTH: 11
<212> TYPE: PRT
<213> ORGANISM: Unknown
<220> FEATURE:
<223> OTHER INFORMATION: Description of Unknown: Gliadin fragment
      peptide
```

```
<400> SEQUENCE: 113

Gln Pro Tyr Pro Gln Gln Pro Gln Gln Pro Phe
1               5                   10

<210> SEQ ID NO 114
<211> LENGTH: 12
<212> TYPE: PRT
<213> ORGANISM: Unknown
<220> FEATURE:
<223> OTHER INFORMATION: Description of Unknown: Gliadin fragment
      peptide

<400> SEQUENCE: 114

Gln Pro Tyr Pro Gln Gln Pro Gln Gln Pro Phe Pro
1               5                   10

<210> SEQ ID NO 115
<211> LENGTH: 10
<212> TYPE: PRT
<213> ORGANISM: Unknown
<220> FEATURE:
<223> OTHER INFORMATION: Description of Unknown: Gliadin fragment
      peptide

<400> SEQUENCE: 115

Tyr Pro Gln Gln Pro Gln Gln Pro Phe Pro
1               5                   10

<210> SEQ ID NO 116
<211> LENGTH: 20
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Pro, Ala or Gln
<220> FEATURE:
<221> NAME/KEY: MOD_RES
<222> LOCATION: (12)..(12)
<223> OTHER INFORMATION: Gly or Glu
<220> FEATURE:
<221> NAME/KEY: MOD_RES
<222> LOCATION: (13)..(13)
<223> OTHER INFORMATION: Gly or Asp
<220> FEATURE:
<221> NAME/KEY: MOD_RES
<222> LOCATION: (14)..(14)
<223> OTHER INFORMATION: Asn, Lys or Ser
<220> FEATURE:
<221> NAME/KEY: MOD_RES
<222> LOCATION: (15)..(15)
<223> OTHER INFORMATION: Lys, Ser, Gln, Arg or Asn
<220> FEATURE:
<221> NAME/KEY: MOD_RES
<222> LOCATION: (16)..(16)
<223> OTHER INFORMATION: Pro, Arg, Gln or Ser
<220> FEATURE:
<221> NAME/KEY: MOD_RES
<222> LOCATION: (17)..(17)
<223> OTHER INFORMATION: Gln or Ser
<220> FEATURE:
<221> NAME/KEY: MOD_RES
<222> LOCATION: (18)..(18)
<223> OTHER INFORMATION: Gly, Pro or Ser
<220> FEATURE:
<221> NAME/KEY: MOD_RES
<222> LOCATION: (19)..(19)
<223> OTHER INFORMATION: Pro, Gln, Ala or Arg
<220> FEATURE:
<221> NAME/KEY: MOD_RES
<222> LOCATION: (20)..(20)
<223> OTHER INFORMATION: Pro, Ser or Arg
```

-continued

```
<400> SEQUENCE: 116

Pro Pro Gly Lys Pro Gln Gly Pro Pro Xaa Gln Xaa Xaa Xaa Xaa Xaa
1               5                   10                  15

Xaa Xaa Xaa Xaa
            20

<210> SEQ ID NO 117
<211> LENGTH: 20
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: Gly or Asp
<220> FEATURE:
<221> NAME/KEY: MOD_RES
<222> LOCATION: (14)..(14)
<223> OTHER INFORMATION: Asn, Lys or Ser
<220> FEATURE:
<221> NAME/KEY: MOD_RES
<222> LOCATION: (15)..(15)
<223> OTHER INFORMATION: Lys, Ser or Gln
<220> FEATURE:
<221> NAME/KEY: MOD_RES
<222> LOCATION: (16)..(16)
<223> OTHER INFORMATION: Pro, Arg or Ser
<220> FEATURE:
<221> NAME/KEY: MOD_RES
<222> LOCATION: (17)..(17)
<223> OTHER INFORMATION: Gln, Arg or Ser
<220> FEATURE:
<221> NAME/KEY: MOD_RES
<222> LOCATION: (18)..(18)
<223> OTHER INFORMATION: Gly, Pro or Ser
<220> FEATURE:
<221> NAME/KEY: MOD_RES
<222> LOCATION: (19)..(19)
<223> OTHER INFORMATION: Pro, Ser, Ala or Arg
<220> FEATURE:
<221> NAME/KEY: MOD_RES
<222> LOCATION: (20)..(20)
<223> OTHER INFORMATION: Pro, Ser or Arg

<400> SEQUENCE: 117

Pro Pro Gly Lys Pro Gln Gly Pro Pro Gln Gly Xaa Xaa Xaa Xaa
1               5                   10                  15

Xaa Xaa Xaa Xaa
            20

<210> SEQ ID NO 118
<211> LENGTH: 21
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Arg or His
<220> FEATURE:
<221> NAME/KEY: MOD_RES
<222> LOCATION: (6)..(6)
<223> OTHER INFORMATION: Glu or Gln
<220> FEATURE:
<221> NAME/KEY: MOD_RES
<222> LOCATION: (8)..(8)
<223> OTHER INFORMATION: Pro, Gln or Ser
<220> FEATURE:
<221> NAME/KEY: MOD_RES
<222> LOCATION: (10)..(10)
<223> OTHER INFORMATION: Pro or Ser
<220> FEATURE:
<221> NAME/KEY: MOD_RES
<222> LOCATION: (12)..(12)
<223> OTHER INFORMATION: Gly or Glu
```

```
<220> FEATURE:
<221> NAME/KEY: MOD_RES
<222> LOCATION: (15)..(15)
<223> OTHER INFORMATION: Gln or Lys
<220> FEATURE:
<221> NAME/KEY: MOD_RES
<222> LOCATION: (16)..(16)
<223> OTHER INFORMATION: Ser or Pro
<220> FEATURE:
<221> NAME/KEY: MOD_RES
<222> LOCATION: (17)..(17)
<223> OTHER INFORMATION: Gln or Arg
<220> FEATURE:
<221> NAME/KEY: MOD_RES
<222> LOCATION: (18)..(18)
<223> OTHER INFORMATION: Gly or Arg

<400> SEQUENCE: 118

Xaa Pro Gly Lys Pro Xaa Gly Xaa Pro Xaa Gln Xaa Gly Asn Xaa Xaa
1               5                   10                  15

Xaa Xaa Pro Pro Pro
            20

<210> SEQ ID NO 119
<211> LENGTH: 21
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Glu or Gln
<220> FEATURE:
<221> NAME/KEY: MOD_RES
<222> LOCATION: (4)..(4)
<223> OTHER INFORMATION: Gly or Arg
<220> FEATURE:
<221> NAME/KEY: MOD_RES
<222> LOCATION: (5)..(6)
<223> OTHER INFORMATION: Pro or Arg
<220> FEATURE:
<221> NAME/KEY: MOD_RES
<222> LOCATION: (13)..(13)
<223> OTHER INFORMATION: Pro or Ser
<220> FEATURE:
<221> NAME/KEY: MOD_RES
<222> LOCATION: (14)..(14)
<223> OTHER INFORMATION: Gln or His
<220> FEATURE:
<221> NAME/KEY: MOD_RES
<222> LOCATION: (15)..(15)
<223> OTHER INFORMATION: Arg or Gly
<220> FEATURE:
<221> NAME/KEY: MOD_RES
<222> LOCATION: (16)..(16)
<223> OTHER INFORMATION: Pro or Thr
<220> FEATURE:
<221> NAME/KEY: MOD_RES
<222> LOCATION: (19)..(19)
<223> OTHER INFORMATION: Pro or His

<400> SEQUENCE: 119

Lys Pro Xaa Xaa Xaa Xaa Pro Gln Gly Gly Asn Gln Xaa Xaa Xaa Xaa
1               5                   10                  15

Pro Pro Xaa Pro Gly
            20

<210> SEQ ID NO 120
<211> LENGTH: 14
<212> TYPE: PRT
<213> ORGANISM: Homo sapiens

<400> SEQUENCE: 120
```

```
Asn Gln Pro Gln Gly Pro Pro Pro Pro Gly Lys Pro Gln
1               5                   10
```

<210> SEQ ID NO 121
<211> LENGTH: 14
<212> TYPE: PRT
<213> ORGANISM: Homo sapiens

<400> SEQUENCE: 121

```
Pro Pro Pro Gln Gly Asp Lys Ser Gln Ser Pro Arg Ser Pro
1               5                   10
```

<210> SEQ ID NO 122
<211> LENGTH: 15
<212> TYPE: PRT
<213> ORGANISM: Homo sapiens

<400> SEQUENCE: 122

```
Pro Pro Pro Gln Gly Gly Asn Gln Pro Gln Gly Pro Pro Pro Pro
1               5                   10                  15
```

<210> SEQ ID NO 123
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 123

```
Pro Gln Pro Gln Leu Pro Tyr Pro Gln Pro Gln Leu Pro Tyr
1               5                   10
```

<210> SEQ ID NO 124
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 124

```
Gln Pro Pro Phe Ser Gln Gln Gln Gln Ser Pro Phe Ser Gln
1               5                   10
```

<210> SEQ ID NO 125
<211> LENGTH: 15
<212> TYPE: PRT
<213> ORGANISM: Unknown
<220> FEATURE:
<223> OTHER INFORMATION: Description of Unknown: Gliadin fragment
      peptide

<400> SEQUENCE: 125

```
Val Gln Gly Gln Gly Ile Ile Gln Pro Gln Gln Pro Ala Gln Leu
1               5                   10                  15
```

<210> SEQ ID NO 126
<211> LENGTH: 14
<212> TYPE: PRT
<213> ORGANISM: Homo sapiens

<400> SEQUENCE: 126

```
Gly Asn Arg Pro Gln Gly Pro Pro Pro Gly Lys Pro Gln
1               5                   10
```

```
<210> SEQ ID NO 127
<211> LENGTH: 27
<212> TYPE: PRT
<213> ORGANISM: Homo sapiens

<400> SEQUENCE: 127

Gln Pro Gln Ala Pro Pro Ala Gly Gln Pro Gln Gly Pro Pro Arg Pro
1               5                   10                  15

Pro Gln Gly Gly Arg Pro Ser Arg Pro Pro Gln
            20                  25

<210> SEQ ID NO 128
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 128

Pro Phe Arg Pro Gln Gln Pro Tyr Pro Gln Pro Gln Pro Gln
1               5                   10

<210> SEQ ID NO 129
<211> LENGTH: 12
<212> TYPE: PRT
<213> ORGANISM: Unknown
<220> FEATURE:
<223> OTHER INFORMATION: Description of Unknown: Gliadin fragment
      peptide

<400> SEQUENCE: 129

Gln Leu Gln Pro Phe Pro Gln Pro Gln Leu Pro Tyr
1               5                   10

<210> SEQ ID NO 130
<211> LENGTH: 13
<212> TYPE: PRT
<213> ORGANISM: Unknown
<220> FEATURE:
<223> OTHER INFORMATION: Description of Unknown: Gliadin fragment
      peptide

<400> SEQUENCE: 130

Gln Gln Gly Tyr Tyr Pro Thr Ser Pro Gln Gln Ser Gly
1               5                   10

<210> SEQ ID NO 131
<211> LENGTH: 16
<212> TYPE: PRT
<213> ORGANISM: Unknown
<220> FEATURE:
<223> OTHER INFORMATION: Description of Unknown: Gliadin fragment
      peptide

<400> SEQUENCE: 131

Gln Pro Gln Gln Pro Gln Gln Ser Phe Pro Gln Gln Arg Pro Phe
1               5                   10                  15

<210> SEQ ID NO 132
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 132
```

```
Gln Gln Pro Phe Ser Gln Gln Gln Gln Pro Leu Pro Gln
1               5                   10

<210> SEQ ID NO 133
<211> LENGTH: 14
<212> TYPE: PRT
<213> ORGANISM: Homo sapiens

<400> SEQUENCE: 133

Gly Pro Pro Pro Gln Gly Asp Lys Ser Arg Ser Pro Arg Ser
1               5                   10

<210> SEQ ID NO 134
<211> LENGTH: 14
<212> TYPE: PRT
<213> ORGANISM: Homo sapiens

<400> SEQUENCE: 134

Asn Gln Pro Gln Gly Pro Pro Pro Pro Gly Lys Pro Gln
1               5                   10

<210> SEQ ID NO 135
<211> LENGTH: 15
<212> TYPE: PRT
<213> ORGANISM: Homo sapiens

<400> SEQUENCE: 135

Pro Pro Pro Gln Gly Gly Asn Gln Pro Gln Gly Pro Pro Pro
1               5                   10                  15

<210> SEQ ID NO 136
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 136

Gln Pro Pro Phe Ser Gln Gln Gln Gln Ser Pro Phe Ser Gln
1               5                   10

<210> SEQ ID NO 137
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 137

Pro Gln Pro Gln Leu Pro Tyr Pro Gln Pro Gln Leu Pro Tyr
1               5                   10

<210> SEQ ID NO 138
<211> LENGTH: 15
<212> TYPE: PRT
<213> ORGANISM: Unknown
<220> FEATURE:
<223> OTHER INFORMATION: Description of Unknown: Gliadin fragment
      peptide

<400> SEQUENCE: 138

Val Gln Gly Gln Gly Ile Ile Gln Pro Gln Gln Pro Ala Gln Leu
1               5                   10                  15
```

<210> SEQ ID NO 139
<211> LENGTH: 14
<212> TYPE: PRT
<213> ORGANISM: Homo sapiens

<400> SEQUENCE: 139

Gly Asn Lys Pro Gln Gly Pro Pro Pro Gly Lys Pro Gln
1               5                   10

<210> SEQ ID NO 140
<211> LENGTH: 27
<212> TYPE: PRT
<213> ORGANISM: Homo sapiens

<400> SEQUENCE: 140

Gln Pro Gln Ala Pro Pro Ala Gly Gln Pro Gln Gly Pro Pro Arg Pro
1               5                   10                  15

Pro Gln Gly Gly Arg Pro Ser Arg Pro Pro Gln
            20                  25

<210> SEQ ID NO 141
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 141

Pro Phe Arg Pro Gln Gln Pro Tyr Pro Gln Pro Gln Pro Gln
1               5                   10

<210> SEQ ID NO 142
<211> LENGTH: 12
<212> TYPE: PRT
<213> ORGANISM: Unknown
<220> FEATURE:
<223> OTHER INFORMATION: Description of Unknown: Gliadin fragment
      peptide

<400> SEQUENCE: 142

Gln Leu Gln Pro Phe Pro Gln Pro Gln Leu Pro Tyr
1               5                   10

<210> SEQ ID NO 143
<211> LENGTH: 13
<212> TYPE: PRT
<213> ORGANISM: Unknown
<220> FEATURE:
<223> OTHER INFORMATION: Description of Unknown: Gliadin fragment
      peptide

<400> SEQUENCE: 143

Gln Gln Gly Tyr Tyr Pro Thr Ser Pro Gln Gln Ser Gly
1               5                   10

<210> SEQ ID NO 144
<211> LENGTH: 16
<212> TYPE: PRT
<213> ORGANISM: Unknown
<220> FEATURE:
<223> OTHER INFORMATION: Description of Unknown: Gliadin fragment
      peptide

<400> SEQUENCE: 144

Gln Pro Gln Gln Pro Gln Gln Ser Phe Pro Gln Gln Gln Arg Pro Phe

```
<210> SEQ ID NO 145
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 145

Gln Gln Pro Phe Ser Gln Gln Gln Gln Pro Leu Pro Gln
1               5                   10

<210> SEQ ID NO 146
<211> LENGTH: 14
<212> TYPE: PRT
<213> ORGANISM: Homo sapiens

<400> SEQUENCE: 146

Gly Asn Lys Pro Gln Arg Pro Pro Pro Arg Arg Pro Gln
1               5                   10

<210> SEQ ID NO 147
<211> LENGTH: 14
<212> TYPE: PRT
<213> ORGANISM: Homo sapiens

<400> SEQUENCE: 147

Pro Pro Pro Pro Gly Gly Asn Pro Gln Gln Pro Leu Pro Pro
1               5                   10

<210> SEQ ID NO 148
<211> LENGTH: 16
<212> TYPE: PRT
<213> ORGANISM: Homo sapiens

<400> SEQUENCE: 148

Gly Lys Pro Gln Gly Pro Pro Pro Pro Gln Gly Gly Arg Pro His
1               5                   10                  15

<210> SEQ ID NO 149
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 149

Pro Phe Arg Pro Gln Gln Pro Tyr Pro Gln Pro Gln Pro Gln
1               5                   10

<210> SEQ ID NO 150
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 150

Gln Gln Pro Phe Ser Gln Gln Gln Gln Pro Leu Pro Gln
1               5                   10

<210> SEQ ID NO 151
```

```
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 151

Pro Gln Pro Gln Leu Pro Tyr Pro Gln Pro Gln Leu Pro Tyr
1               5                   10

<210> SEQ ID NO 152
<211> LENGTH: 20
<212> TYPE: PRT
<213> ORGANISM: Homo sapiens

<400> SEQUENCE: 152

Arg Arg Pro Gln Gly Gly Asn Gln Pro Gln Arg Pro Pro Pro Pro
1               5                   10                  15

Gly Lys Pro Gln
            20

<210> SEQ ID NO 153
<211> LENGTH: 13
<212> TYPE: PRT
<213> ORGANISM: Homo sapiens

<400> SEQUENCE: 153

Gln Glu Gly Asn Lys Pro Gln Gly Pro Pro Pro Pro Gly
1               5                   10

<210> SEQ ID NO 154
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 154

Pro Gln Pro Gln Leu Pro Tyr Pro Gln Pro Gln Leu Pro Tyr
1               5                   10

<210> SEQ ID NO 155
<211> LENGTH: 13
<212> TYPE: PRT
<213> ORGANISM: Unknown
<220> FEATURE:
<223> OTHER INFORMATION: Description of Unknown: Gliadin fragment
      peptide

<400> SEQUENCE: 155

Gln Gln Gly Tyr Tyr Pro Thr Ser Pro Gln Gln Ser Gly
1               5                   10

<210> SEQ ID NO 156
<211> LENGTH: 15
<212> TYPE: PRT
<213> ORGANISM: Unknown
<220> FEATURE:
<223> OTHER INFORMATION: Description of Unknown: Gliadin fragment
      peptide

<400> SEQUENCE: 156

Val Gln Gly Gln Gly Ile Ile Gln Pro Gln Gln Pro Ala Gln Leu
1               5                   10                  15
```

```
<210> SEQ ID NO 157
<211> LENGTH: 20
<212> TYPE: PRT
<213> ORGANISM: Homo sapiens

<400> SEQUENCE: 157

Arg Arg Pro Gln Gly Gly Asn Gln Pro Gln Arg Pro Pro Pro Pro Pro
1               5                   10                  15

Gly Lys Pro Gln
            20

<210> SEQ ID NO 158
<211> LENGTH: 13
<212> TYPE: PRT
<213> ORGANISM: Homo sapiens

<400> SEQUENCE: 158

Gln Glu Gly Asn Lys Pro Gln Gly Pro Pro Pro Pro Gly
1               5                   10

<210> SEQ ID NO 159
<211> LENGTH: 14
<212> TYPE: PRT
<213> ORGANISM: Unknown
<220> FEATURE:
<223> OTHER INFORMATION: Description of Unknown: Gliadin fragment
      peptide

<400> SEQUENCE: 159

Pro Gln Pro Gln Leu Pro Tyr Pro Gln Pro Gln Leu Pro Tyr
1               5                   10

<210> SEQ ID NO 160
<211> LENGTH: 13
<212> TYPE: PRT
<213> ORGANISM: Unknown
<220> FEATURE:
<223> OTHER INFORMATION: Description of Unknown: Gliadin fragment
      peptide

<400> SEQUENCE: 160

Gln Gln Gly Tyr Tyr Pro Thr Ser Pro Gln Gln Ser Gly
1               5                   10

<210> SEQ ID NO 161
<211> LENGTH: 15
<212> TYPE: PRT
<213> ORGANISM: Unknown
<220> FEATURE:
<223> OTHER INFORMATION: Description of Unknown: Gliadin fragment
      peptide

<400> SEQUENCE: 161

Val Gln Gly Gln Gly Ile Ile Gln Pro Gln Gln Pro Ala Gln Leu
1               5                   10                  15

<210> SEQ ID NO 162
<211> LENGTH: 475
<212> TYPE: PRT
<213> ORGANISM: Rothia mucilaginosa

<400> SEQUENCE: 162

Met Ser Thr Asn Ile Ser Arg Arg Lys Val Val Ala Gly Ala Ala Trp
1               5                   10                  15

Ala Ala Pro Val Val Ala Ala Ser Ala Ala Val Pro Ala Phe Ala Ser
```

-continued

```
                20                  25                  30
Ser Thr Glu Cys Asp Tyr Ala Ser Ala Pro Lys Phe Asn Ile Ser Gly
            35                  40                  45
Gln Pro Ser Gly Ala Lys Asp Thr Val Lys Phe Thr Val Pro Ala Lys
        50                  55                  60
Val Asp Lys Ile Lys Phe Glu Val Ala Gly Ala Gly Gly Gly Gly Ser
 65                  70                  75                  80
Asn Gln Val Ala Gly Gly Ser Gly Ala Leu Val Thr Gly Val Ile Pro
                85                  90                  95
Val Lys Glu Gly Gln Val Ile Glu Leu Val Ala Ser Gly Gly Val
            100                 105                 110
Ala Tyr Leu Glu Ser Val Arg Gly Val Asp Ser Pro Ala Leu Trp Gln
            115                 120                 125
Thr Arg Pro Ala Thr Gly Gly Lys Gly Tyr Gly Asn Gly Gly Asp Val
        130                 135                 140
Asn Glu Gln Pro Val Pro Ala Asp Val Lys Ala Gln Val Asp Ala Asn
145                 150                 155                 160
Trp Ser Lys Pro Ser Asp Met Lys Arg Tyr Leu Tyr Gly Gly Ser Gly
                165                 170                 175
Gly Gly Ser Ser Ala Leu Ile Ile Asn Gly Thr Pro Val Ala Val Ala
            180                 185                 190
Gly Gly Gly Gly Ala Gly Ile Arg Thr Gln Pro Gly Thr Asn Asn
            195                 200                 205
Met Pro Ser Gly Lys Tyr Tyr Asn Pro Lys Ala Val Asp Ala Ser Thr
        210                 215                 220
Thr Arg Leu Ser Asp Pro Asp Val Lys Ser Val Leu Pro Ala Gly Ala
225                 230                 235                 240
Ser Ala Ser Ala Ala Val Gly Asp Ser Ala Glu Thr Ser Ile Ser His
                245                 250                 255
Tyr Thr Val Leu Lys Pro His Thr Thr Asp Gly Thr Ala Met Lys Val
            260                 265                 270
Ala Gly Gly His Gly Gly Gly Asn Gly Gln Gly Gly Ala Gly Gly Glu
            275                 280                 285
Gln Pro Leu Leu Tyr Ser Thr Leu Gly Asn Val Tyr Gly Val Leu Gly
        290                 295                 300
Phe Lys Ser Gln Asn Lys Gln Glu Leu Phe Ser Ser Ala Thr Ala Gly
305                 310                 315                 320
Asp Lys Gly Gly Ser Gly Phe Asp Gly Lys Gly Ala Asp Gly Val Phe
                325                 330                 335
Ala Tyr Ser Tyr Gln Ile Asp Asn Asn Asp Ile Ser Lys Leu Glu Ile
            340                 345                 350
Val His Ala Thr Asn Pro Val Asn Leu Asn Asp Lys Thr Asn Leu Asp
            355                 360                 365
Glu Asp Ser Thr Arg Lys Ser Phe Asn Gly Tyr Gln Thr Val Val Ser
        370                 375                 380
Ala Gly Gly Gly Ala Gly Tyr Gly Gly Gly Ser Gly Ala Ala Arg
385                 390                 395                 400
Gly Leu Ser Ser Ile Ile Thr Ser Gln Lys Trp Asn Gly Asn Glu Glu
                405                 410                 415
Pro Thr Arg Tyr Arg Gln Asn Val Ser Ala Leu Leu Gln Ala Gly Ala
            420                 425                 430
Gly Gly Ala Gly Gly Ser Tyr Val Ala Pro Ser Val Thr Gly Gly Ala
            435                 440                 445
```

```
Ile Ala Ser Ala Asn Asn Ala Ala Lys Ala Ser Gly Val Arg Asn Pro
    450                 455                 460

Gly Tyr Val Lys Val Tyr Leu Cys Glu Arg Ser
465                 470                 475

<210> SEQ ID NO 163
<211> LENGTH: 315
<212> TYPE: PRT
<213> ORGANISM: Rothia mucilaginosa

<400> SEQUENCE: 163

Met Thr Gln Pro Ile Ser Arg Arg Ser Val Lys Ala Gly Val Trp
1               5                   10                  15

Ser Ala Pro Val Ile Ala Thr Ser Ala Ala Val Pro Ala Tyr Ala Ala
                20                  25                  30

Ser Ser Arg Ser Asp Asp Ser Glu Glu Lys Leu Thr Ile Gln Ser Gly
            35                  40                  45

Leu Phe Val Ser Ala Gln Tyr Gly Gly Gly Phe Val Gly Tyr Ala Ser
    50                  55                  60

Ser Thr Ser Thr Gly Pro Ile His Pro Thr Thr Pro Glu Ala Tyr Phe
65                  70                  75                  80

Ala Ser Ser Ser Lys Pro Gln Ser Asp Leu Asn Trp Asp Asp Ser Ala
                85                  90                  95

Ser Lys Pro Thr Asn Pro Asp Leu Phe Ile Asn Gly Glu Gly Thr Phe
            100                 105                 110

Thr Pro Val Asn Asn Ser Gln Thr Ala Ser Pro Gly Ser Tyr Val Ala
    115                 120                 125

Ser Ser Gly Phe Trp Trp Ser Val Pro Thr Thr Ala Pro Lys Thr Gly
130                 135                 140

Thr Gly Tyr Val Ala Gly Ser Thr Ala Thr Leu Ala Ala Gly Ala Thr
145                 150                 155                 160

Phe Val Thr Asp Val Glu Tyr Thr Val Pro Ala Asn Ala Leu Asn Gly
                165                 170                 175

Ala Lys Ser Gly Lys Val Asn Gly Gln Ala Trp Thr Pro Asn Gly Arg
            180                 185                 190

Ala Pro Lys Gly Thr Leu Ala Glu Leu Val Ala Ser Ala Gly Gln Ala
    195                 200                 205

Arg Tyr Leu Ser Val Ala Gln Ala Ala Gly Asn Trp Ser Ala Ser Val
210                 215                 220

Pro Thr Val Thr Lys Asn Ser Asp Gly Thr Tyr Thr Phe Lys Gly Arg
225                 230                 235                 240

Ile Thr Phe Thr Thr Lys Ala Tyr Thr Leu Lys Gln Thr Gly Asn
                245                 250                 255

Lys Leu Tyr Gly Gln Val Val Ile Met Pro Gly Ile Val Phe Phe Asn
            260                 265                 270

Pro Ala Gln Gly Trp Val Ser Tyr Lys Gln Thr Ser Ser Ile Gln Asn
    275                 280                 285

Ala Thr Ile Asn Tyr Ser Gly Asn Gly Tyr Thr Asp Thr Lys Val Leu
290                 295                 300

Ser Gly Ala Glu Thr Thr Thr Gln Ile Asn Pro
305                 310                 315

<210> SEQ ID NO 164
<211> LENGTH: 317
<212> TYPE: PRT
```

<213> ORGANISM: Rothia mucilaginosa

<400> SEQUENCE: 164

Met Asp Ile His Ser Thr Lys Ser His Ser Glu Gln Ser Gly Lys Leu
1               5                   10                  15

Met Gly Arg Arg Thr Leu Val Lys Gly Ala Ala Trp Ala Thr Pro Val
            20                  25                  30

Val Ala Ala Thr Ala Val Val Pro Ala Tyr Ala Ser Lys Asn Pro
        35                  40                  45

Cys Glu Tyr Gly Thr Ile Val Ser Val Pro Trp Gly Glu Arg Ala Asn
    50                  55                  60

Arg Arg Arg Tyr Lys Gly Thr Val Asn Glu Glu Tyr Glu Trp Ala Val
65                  70                  75                  80

Met Pro Thr Ser Asn Cys Ser Pro Gln Pro Gln Thr Tyr Phe Ile Asp
                85                  90                  95

Asn Thr Thr Pro Glu Asn Lys Leu Ala Tyr Pro Trp Gly Arg Tyr Glu
            100                 105                 110

Gly Val Ser Asp Phe Pro Pro Ile Tyr Pro Asn Gly Lys Asp Thr
        115                 120                 125

Pro Asp Tyr Thr Ser Lys Asp Gly Val Gly Val Gly Gly Val
    130                 135                 140

Ile Ile Asn Val Arg Val Glu Asn Val Ala Gly Asp Val Ser Tyr Ala
145                 150                 155                 160

Pro Thr Pro Thr Gly Ala Asp Arg Phe Ala Phe Gly Glu Ser Asp Ala
                165                 170                 175

Asn Arg Lys Asn Asn Met Tyr Tyr Ala Glu Gly Tyr Lys Gly Lys Gly
            180                 185                 190

Ala Asn Pro Pro Val Val Arg Leu Asn Asp Asn Tyr Lys Gly Ser Arg
        195                 200                 205

Ser Thr Tyr Ile Ala His Gly Lys Tyr Asn Tyr Leu His Phe Pro Asp
    210                 215                 220

Gly Pro Arg Pro Pro Lys Glu Asn Ser Pro Leu Trp Thr Tyr Ala Tyr
225                 230                 235                 240

Gly Lys His Tyr Thr Thr Ala Glu Gly Arg Asp Gly Trp Ser Trp Asp
                245                 250                 255

Ile Gln Val Met Ala Asn Ile Thr His Pro Asn Ala Gly Gln Asp Val
            260                 265                 270

Val Ser Tyr Met Thr Tyr Leu Arg Lys His Thr Tyr Gly Asp Pro Ala
        275                 280                 285

His Gln Ser Ala Lys Val Ile Pro Val Gln Tyr Arg Val Ile Val Thr
    290                 295                 300

Ser Pro Trp Gly Thr Val Thr Tyr Leu Ser Ala Ala Val
305                 310                 315

<210> SEQ ID NO 165
<211> LENGTH: 13
<212> TYPE: PRT
<213> ORGANISM: Unknown
<220> FEATURE:
<223> OTHER INFORMATION: Description of Unknown: Gliadin fragment
      peptide

<400> SEQUENCE: 165

Pro Gln Pro Glu Leu Pro Tyr Pro Gln Pro Gln Leu Pro
1               5                   10

```
<210> SEQ ID NO 166
<211> LENGTH: 416
<212> TYPE: PRT
<213> ORGANISM: Homo sapiens

<400> SEQUENCE: 166
```

| | | | | | | | | | | | | | | | |
|---|---|---|---|---|---|---|---|---|---|---|---|---|---|---|---|
| Met | Leu | Leu | Ile | Leu | Leu | Ser | Val | Ala | Leu | Ala | Leu | Ser | Ser | Ala |
| 1 | | | | 5 | | | | | 10 | | | | | 15 |
| Gln | Asn | Leu | Asn | Glu | Asp | Val | Ser | Gln | Glu | Glu | Ser | Pro | Ser | Leu | Ile |
| | | | 20 | | | | | 25 | | | | | 30 | | |
| Ala | Gly | Asn | Pro | Gln | Gly | Ala | Pro | Pro | Gln | Gly | Gly | Asn | Lys | Pro | Gln |
| | | | 35 | | | | | 40 | | | | | 45 | | |
| Gly | Pro | Pro | Ser | Pro | Pro | Gly | Lys | Pro | Gln | Gly | Pro | Pro | Pro | Gln | Gly |
| | | 50 | | | | | 55 | | | | | 60 | | | |
| Gly | Asn | Gln | Pro | Gln | Gly | Pro | Pro | Pro | Pro | Gly | Lys | Pro | Gln | Gly |
| 65 | | | | | 70 | | | | | 75 | | | | | 80 |
| Pro | Pro | Pro | Gln | Gly | Gly | Asn | Lys | Pro | Gln | Gly | Pro | Pro | Pro | Gly |
| | | | | 85 | | | | | 90 | | | | | 95 |
| Lys | Pro | Gln | Gly | Pro | Pro | Gln | Gly | Asp | Lys | Ser | Arg | Ser | Pro | Arg |
| | | | 100 | | | | | 105 | | | | | 110 | | |
| Ser | Pro | Pro | Gly | Lys | Pro | Gln | Gly | Pro | Pro | Gln | Gly | Gly | Asn | Gln |
| | | | 115 | | | | | 120 | | | | | 125 | | |
| Pro | Gln | Gly | Pro | Pro | Pro | Pro | Gly | Lys | Pro | Gln | Gly | Pro | Pro | Pro |
| | | 130 | | | | | 135 | | | | | 140 | | | |
| Gln | Gly | Gly | Asn | Lys | Pro | Gln | Gly | Pro | Pro | Pro | Gly | Lys | Pro | Gln |
| 145 | | | | | 150 | | | | | 155 | | | | | 160 |
| Gly | Pro | Pro | Pro | Gln | Gly | Asp | Asn | Lys | Ser | Arg | Ser | Arg | Ser | Pro |
| | | | | 165 | | | | | 170 | | | | | 175 |
| Pro | Gly | Lys | Pro | Gln | Gly | Pro | Pro | Gln | Gly | Gly | Asn | Gln | Pro | Gln |
| | | | 180 | | | | | 185 | | | | | 190 | | |
| Gly | Pro | Pro | Pro | Pro | Gly | Lys | Pro | Gln | Gly | Pro | Pro | Gln | Gly |
| | | | 195 | | | | | 200 | | | | | 205 | | |
| Gly | Asn | Lys | Pro | Gln | Gly | Pro | Pro | Pro | Gly | Lys | Pro | Gln | Gly | Pro |
| | | | 210 | | | | | 215 | | | | | 220 | | |
| Pro | Pro | Gln | Gly | Asp | Asn | Lys | Ser | Gln | Ser | Ala | Arg | Ser | Pro | Pro | Gly |
| 225 | | | | | 230 | | | | | 235 | | | | | 240 |
| Lys | Pro | Gln | Gly | Pro | Pro | Gln | Gly | Gly | Asn | Gln | Pro | Gln | Gly | Pro |
| | | | | 245 | | | | | 250 | | | | | 255 |
| Pro | Pro | Pro | Pro | Gly | Lys | Pro | Gln | Gly | Pro | Pro | Gln | Gly | Gly | Asn |
| | | | 260 | | | | | 265 | | | | | 270 | | |
| Lys | Ser | Gln | Gly | Pro | Pro | Pro | Gly | Lys | Pro | Gln | Gly | Pro | Pro | Pro |
| | | | 275 | | | | | 280 | | | | | 285 | | |
| Gln | Gly | Gly | Ser | Lys | Ser | Arg | Ser | Ser | Arg | Ser | Pro | Pro | Gly | Lys | Pro |
| | | 290 | | | | | 295 | | | | | 300 | | | |
| Gln | Gly | Pro | Pro | Gln | Gly | Gly | Asn | Gln | Pro | Gly | Pro | Pro | Pro |
| 305 | | | | | 310 | | | | | 315 | | | | | 320 |
| Pro | Pro | Gly | Lys | Pro | Gln | Gly | Pro | Pro | Gln | Gly | Gly | Asn | Lys | Pro |
| | | | | 325 | | | | | 330 | | | | | 335 |
| Gln | Gly | Pro | Pro | Pro | Gly | Lys | Pro | Gln | Gly | Pro | Pro | Gln | Gly |
| | | | 340 | | | | | 345 | | | | | 350 | | |
| Gly | Ser | Lys | Ser | Arg | Ser | Ala | Arg | Ser | Pro | Gly | Lys | Pro | Gln | Gly |
| | | | 355 | | | | | 360 | | | | | 365 | | |
| Pro | Pro | Gln | Gln | Glu | Gly | Asn | Asn | Pro | Gln | Gly | Pro | Pro | Pro | Ala |
| | | 370 | | | | | 375 | | | | | 380 | | | |

-continued

Gly Gly Asn Pro Gln Gln Pro Gln Ala Pro Ala Gly Gln Pro Gln
385                 390                 395                 400

Gly Pro Pro Arg Pro Pro Gln Gly Gly Arg Pro Ser Arg Pro Pro Gln
            405                 410                 415

<210> SEQ ID NO 167
<211> LENGTH: 439
<212> TYPE: PRT
<213> ORGANISM: Triticum aestivum

<400> SEQUENCE: 167

Met Lys Thr Phe Ile Ile Phe Val Leu Leu Ala Met Ala Met Asn Ile
1               5                   10                  15

Ala Ser Ala Ser Arg Leu Leu Ser Pro Arg Gly Lys Glu Leu His Thr
            20                  25                  30

Pro Gln Glu Gln Phe Pro Gln Gln Gln Phe Pro Gln Pro Gln Gln
        35                  40                  45

Phe Pro Gln Gln Gln Ile Pro Gln Gln His Gln Ile Pro Gln Gln Pro
50                  55                  60

Gln Gln Phe Pro Gln Gln Gln Phe Leu Gln Gln Gln Ile Pro
65                  70                  75                  80

Gln Gln Ile Pro Gln His Gln Ile Pro Gln Pro Gln Gln
                85                  90                  95

Phe Pro Gln Gln Gln Phe Pro Gln His Gln Ser Pro Gln Gln
            100                 105                 110

Gln Phe Pro Gln Gln Gln Phe Pro Gln Gln Lys Leu Pro Gln Gln Glu
            115                 120                 125

Phe Pro Gln Gln Gln Ile Ser Gln Gln Pro Gln Gln Leu Pro Gln Gln
130                 135                 140

Gln Gln Ile Pro Gln Pro Gln Gln Phe Leu Gln Gln Gln Gln Phe
145                 150                 155                 160

Pro Gln Gln Gln Pro Pro Gln Gln His Gln Phe Pro Gln Gln Gln Leu
                165                 170                 175

Pro Gln Gln Gln Ile Pro Gln Gln Gln Ile Pro Gln Gln Pro
            180                 185                 190

Gln Gln Ile Pro Gln Gln Gln Gln Ile Pro Gln Gln Pro Gln Gln Phe
            195                 200                 205

Pro Gln Gln Gln Phe Pro Gln Gln Gln Phe Pro Gln Gln Gln Phe Pro
            210                 215                 220

Gln Gln Glu Phe Pro Gln Gln Gln Phe Pro Gln Gln Gln Ile Ala
225                 230                 235                 240

Arg Gln Pro Gln Gln Leu Pro Gln Gln Gln Ile Pro Gln Gln Pro
                245                 250                 255

Gln Gln Phe Pro Gln Gln Gln Phe Pro Gln Gln Gln Ser Pro Gln
            260                 265                 270

Gln Gln Gln Phe Pro Gln Gln Gln Phe Pro Gln Gln Gln Leu Pro
            275                 280                 285

Gln Lys Gln Phe Pro Gln Pro Gln Ile Pro Gln Gln Gln Ile
            290                 295                 300

Pro Gln Pro Gln Gln Phe Pro Gln Gln Phe Pro Gln Gln Gln
305                 310                 315                 320

Gln Phe Pro Gln Gln Gln Glu Phe Pro Gln Gln Gln Phe Pro Gln Gln
            325                 330                 335

Gln Phe His Gln Gln Gln Leu Pro Gln Gln Gln Phe Pro Gln Gln Gln
            340                 345                 350

```
Phe Pro Gln Gln Gln Phe Pro Gln Gln Gln Phe Pro Gln Gln Gln
            355                 360                 365

Gln Leu Thr Gln Gln Gln Phe Pro Arg Pro Gln Gln Ser Pro Glu Gln
    370                 375                 380

Gln Gln Phe Pro Gln Gln Gln Phe Pro Gln Gln Pro Pro Gln Gln Phe
385                 390                 395                 400

Pro Gln Gln Gln Phe Pro Ile Pro Tyr Pro Pro Gln Gln Ser Glu Glu
                405                 410                 415

Pro Ser Pro Tyr Gln Gln Tyr Pro Gln Gln Gln Pro Ser Gly Ser Asp
                420                 425                 430

Val Ile Ser Ile Ser Gly Leu
            435

<210> SEQ ID NO 168
<211> LENGTH: 6
<212> TYPE: PRT
<213> ORGANISM: Unknown
<220> FEATURE:
<223> OTHER INFORMATION: Description of Unknown: Gliadin fragment
      peptide

<400> SEQUENCE: 168

Pro Gln Pro Gln Leu Pro
1               5

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Abz
<220> FEATURE:
<221> NAME/KEY: MOD_RES
<222> LOCATION: (7)..(7)
<223> OTHER INFORMATION: Tyr(NO2)

<400> SEQUENCE: 169

Xaa Gln Pro Gln Gln Pro Tyr Asp
1               5
```

ROTHIA SPECIES GLUTEN-DEGRADING ENZYMES AND USES THEREOF

CROSS-REFERENCE TO RELATED APPLICATIONS

This application is a 35 U.S.C. §371 National Phase Entry Application of International Application No. PCT/US2011/043118 filed Jul. 7, 2011, which designates the U.S., and which claims benefit under 35 U.S.C. §119(e) of the U.S. Provisional Application No. 61/362,000 filed Jul. 7, 2010, the contents of which are incorporated herein by reference in their entireties.

GOVERNMENT SUPPORT

This invention was made with Government support under contract No. DE18132 and AI087803 awarded by the National Institutes of Health. The Government has certain rights in the invention.

REFERENCE TO SEQUENCE LISTING

This application contains a Sequence Listing which has been submitted in ASCII format via EFS-Web and is hereby incorporated by reference in its entirety. Said ASCII copy, created on Dec. 31, 2012, is named 20130107_Sequence-Listing-TextFile_701586_068342_US and is 64,094 bytes in size.

FIELD OF THE INVENTION

The field of the invention relates to gluten-degrading enzymes and/or the treatment of celiac disease or a related disorder.

BACKGROUND OF THE INVENTION

Celiac disease, also called celiac sprue or gluten-sensitive enteropathy, is a disease which develops in susceptible individuals in response to the intake of dietary gluten. The disease is caused by an immune reaction to gluten, most noticeably, to gliadin-derived peptides. These peptides elicit an immune response damaging the villi, which are tiny protrusions that line the small intestine. Their destruction causes malabsorbtion of nutrients leading to a variety of generalized gastro-intestinal disease symptoms such as diarrhea and abdominal pain. Additional and secondary symptoms include weight loss, fatigue, anemia, osteopenia and skin and tooth enamel defects.

A related disease/disorder is dermatitis herpetiformis, which is a chronic eruption of the skin characterized by clusters of intensely pruritic vesicles, papules, and urticaria-like lesions. IgA deposits occur in almost all normal-appearing and perilesional skin. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine and colchicines are sometimes prescribed for relief of itching.

Gluten allergy/gluten intolerance is a related ailment which results from overreaction of a subject's immune system to gluten and gliadin that are normally considered harmless. The symptoms are very similar to celiac sprue or gluten-sensitive enteropathy but without the enteropathy. Afflicted subjects have an abundance of IgG, IgA antibodies against α/β-gliadin. Typical symptoms are abdominal pain, gas, bloating and diarrhea; there is a general feeling of sickness and fatigue after grain-based products are consumed. Severe allergy can led to Gluten-sensitive idiopathic neuropathy where the typical symptoms are ataxia and peripheral neuropathies because the primary tissue targeted are the central nervous system and peripheral nerves.

There is currently no good marketed treatment for celiac disease. In most cases, the symptoms are reversible and can be avoided if the patients refrain from the intake of gluten. However, complete elimination of gluten from the diet is not easy to achieve and maintain. Glutens are abundantly contained in dietary products made of wheat, barley and rye. Moreover, gluten is also widely used, for example in commercial soups, sauces, ice creams, hot dogs, and other foods, that patients need detailed lists of foodstuffs to avoid and expert advice from a dietitian familiar with celiac disease. Ingesting even small amounts of gluten may prevent remission or induce relapse. Supplementary vitamins, minerals, and hematinics may also be required, depending on deficiency. A few patients respond poorly or not at all to gluten withdrawal, either because the diagnosis is incorrect or because the disease is refractory. In the latter case, oral corticosteroids (e.g., prednisone 10 to 20 mg bid) may induce response.

The gluten-free diet advice is to be followed for a lifetime, and intake of gluten, even in small amounts, can cause an immediate immunological response. In view of the serious and widespread nature of Celiac Sprue, the development of a non-dietary therapy would allow patients to lead a more normal life and find a broad application in the gluten-sensitive patient population.

Current approaches geared towards the development of treatment options for celiac disease and allergic gluten sensitivity focus on enzyme preparations that are able to digest the immunogenic gluten/gliadin oligopeptides into smaller fragments that do not elicit an immune response. Gluten proteins are remarkably resistant to human digestive enzymes operating in the gastro-intestinal tract due to the low content of lysine/arginine and the high proline content. Enzymes capable of gluten digestion are considered an attractive therapeutic option.

SUMMARY OF THE INVENTION

The methods and compositions described herein are based, in part, on the discovery of novel gluten-degrading enzymes from *Rothia* species bacteria that are found in human plaque or saliva and which retain their activity in acidic pH environments (e.g., pH of 3.0-5.0). These gluten-degrading enzymes can be formulated for the treatment of celiac disease and/or a related disorder, and are especially useful for oral delivery as they retain their activity at acidic and basic pH allowing the enzymes to degrade gluten in the gut as well as transit safely through the acidic environment of the stomach. Compositions for treatment of celiac disease include, but are not limited to, an isolated enzyme, a plurality of isolated enzymes, an extract from *Rothia* species, or even a *Rothia* species bacteria itself.

Accordingly, in one embodiment, provided herein is an isolated enzyme composition comprising at least one gluten-degrading enzyme isolated from a *Rothia* species bacteria, wherein the at least one enzyme retains protease activity at an acidic pH of 3.0 as measured in an in vitro gliadin degradation assay for 3 hours using a synthetic substrate Z-YPQ-pNA, and wherein the at least one enzyme comprises an isoelectric point in a pH range of 2.0-7.0, inclusive.

In another embodiment, provided herein is a probiotic composition comprising an effective amount of *Rothia* species bacteria comprising a gluten-degrading enzyme retains protease activity at acidic pH of 3.0 as measured in an in vitro gliadin degradation assay for 3 hours using a synthetic substrate Z-YPQ-pNA, and wherein the at least one enzyme and comprises an iso-electric point in a pH range of 2.0-7.0, inclusive, and a pharmaceutically acceptable carrier.

In one embodiment, provided herein is a method for treating celiac disease or a related disorder, the method comprising administering to a subject an effective amount of at least one gluten-degrading enzyme isolated from a *Rothia* species bacteria, wherein the at least one enzyme retains protease activity at acidic pH of 3.0 as measured in an in vitro gliadin degradation assay for 3 hours using a synthetic substrate Z-YPQ-pNA, and wherein the at least one enzyme comprises an iso-electric point in a pH range of 2.0-7.0, inclusive, and attenuates gluten toxicity in the subject.

In another embodiment, provided herein is a method for degrading gluten in a gluten-containing foodstuff prior to ingestion, the method comprises contacting the gluten-containing foodstuff with an effective amount of at least one gluten-degrading enzyme isolated from a *Rothia* species bacteria, wherein the at least one enzyme retains protease activity at acidic pH of 3.0 as measured in an in vitro gliadin degradation assay for 3 hours using a synthetic substrate Z-YPQ-pNA, and wherein the at least one enzyme comprises an iso-electric point in a pH range of 2.0-7.0, inclusive.

In one aspect, the compositions described herein relate to an isolated enzyme composition for the treatment of celiac disease or a related disorder, the composition comprising at least one gluten-degrading enzyme isolated from a *Rothia* species bacteria, wherein the at least one enzyme retains activity at varying pH (e.g., acidic pH). In one embodiment, the pH at which the enzyme retains protease activity is pH 2.5. In another embodiment, the pH at which the enzyme retains protease activity is pH 3.0. The enzyme retains at least 5% of the activity when assayed in the in vitro gliadin degradation assay at pH 8.0 for 3 hours using a synthetic substrate Z-YPQ-pNA.

In another aspect, the compositions described herein relate to an isolated enzyme composition for the treatment of gluten-containing foodstuff, the composition comprising at least one gluten-degrading enzyme isolated from a *Rothia* species bacteria, wherein the at least one enzyme retains protease activity at varying pH (e.g., acidic pH). In one embodiment, the pH at which the enzyme retains protease activity is acidic pH. The composition can be admixed to the gluten-containing foodstuff in vivo or in vitro. In vitro treatment of gluten-containing foodstuff reduces the gluten toxicity of the foodstuff prior to ingesting by a subject. In other words, the composition described herein can be used to "pre-digest" gluten-containing foodstuffs to reduce the gluten toxicity. The "pre-digestion" can be complete or partial. In some embodiments, the partial "pre-digestion" can occur in stages such that a final complete digestion occurs prior to ingestion. For example, after an initial "pre-digestion" of a gluten-containing foodstuff with a composition described herein, the partially digested gluten-containing foodstuff is package for shipping or sale. Then, just before a subject is to ingest this partially digested gluten-containing foodstuff, the composition described herein can be sprinkled on to or admixed to the partially digested gluten-containing foodstuff for further digestion to completion before the food reaches the stomach. In other embodiments when the "pre-digestion" is partial, further digestion that reduces or completely eliminate gluten toxicity can occur in vivo after ingestion. In these embodiments, the subject ingests the partially digested gluten-containing foodstuff along with a composition described herein or shortly prior or after eating the partially digested gluten-containing foodstuff. This method ensures that the partially digested gluten-containing foodstuff will be completely digested or eliminated of gluten toxicity (i.e., eliminated of the proline-glutamine rich peptides that are known to be immunogenic on the subject.

It is contemplated that the compositions described herein relating to composition for the treatment of celiac disease or a related disorder, for the treatment of gluten-containing foodstuff, and for the detoxifying gluten-containing foodstuff can comprises an isolated enzyme, a plurality of isolated enzymes, an extract from *Rothia* species, a plurality of extracts from more than one *Rothia* species, a *Rothia* species bacteria itself, or a plurality of *Rothia* species bacteria. It is further contemplated that the composition described herein can comprises a mixture of an isolated enzyme, a plurality of isolated enzymes, an extract from *Rothia* species, or a *Rothia* species bacteria itself.

In one embodiment, the *Rothia* species is *Rothia* species ot 188 (strain WSA-8), also known as *Rothia* sp. HOT-188 and *Rothia aeria*.

In another embodiment, the composition is an oral formulation (e.g., a capsule, liquid, tablet, suspension, or enteric coated capsule or enteric-coated tablet).

In another embodiment, the composition is formulated for treatment of gluten-containing foodstuff prior to ingestion by a subject having celiac disease or a related disorder.

In another embodiment, the at least one gluten-degrading enzyme comprises an iso-electric point in a pH range of 2.0-7.0, inclusive or in a pH range of 2.0-4.0, inclusive.

In other embodiments, the at least one gluten-degrading enzyme comprises a molecular weight between 120-150 kDa, inclusive or between 135-145 kDa, inclusive.

In other embodiments, the at least one enzyme comprises a molecular weight between 50 and 90 kDa, inclusive or between 65 and 75 kDa, inclusive (e.g., 70 kDa).

In some embodiments, the pH can vary between 2.5 and 10, inclusive or between a pH of 2.5-5.0, inclusive or between a pH of 2.8-3.5, inclusive.

In another embodiment, the at least one enzyme degrades a gliadin protein or fragment thereof, such as e.g., a 33-mer peptide of α2-gliadin (e.g., LQLQP-FPQPQLPYPQPQLPYPQPQLPYPQPQPF) (SEQ. ID. NO: 1) or a 26-mer domain derived from γ-gliadin (e.g., FLQPQQPFPQQPQQPYPQQPQQPFPQ) (SEQ. ID. NO: 2).

In another embodiment, degradation or digestion occurs by cleaving the peptide bond, after an amino acid sequence selected from the group consisting of -XPQ-, -QQP-, -PPF-, -LPY- and -PFP-; preferably the amino acid sequence is -XPQ- (e.g., -YPQ-). In other embodiments, degradation or digestion occurs by cleaving the peptide bonds after amino acid sequences XPQ and QQP; XPQ and PPF; XPQ and PFP; XPQ and LPY; QQP and LPY; PPF and LPY; PFP and LPY; XPQ, QQP and PPF; XPQ, QQP and PFP; XPQ, QQP and LPY; QQP, PPF, and PFP; XPQ, PPF and PFP; QQP, PPF and LPY; XPQ, PPF and LPY; PY, PPF, and PFP; QQP, PFP and LPY; XPQ, PFP and LPY; XPQ, QQP, PPF and LYP; LYP, QQP, PPF and PFP; XPQ, LYP, PPF and PFP;

XPQ, QQP, PFP and LYP; XPQ, QQP, PPF and PFP; or XPQ, QQP, PPF, LPY and PFP.

Another aspect described herein relates to a probiotic composition (e.g., living bacteria or lyophilized bacteria) comprising an effective amount of *Rothia* species bacteria comprising a gluten-degrading enzyme that retains activity at varying pH (e.g., acidic pH) and a pharmaceutically acceptable carrier. For example, retaining activity at pH less than 7, pH less than 6, pH less than 5, pH less than 4, pH less than 3 or pH at about 2.5.

In one embodiment, the composition comprises *Rothia* species ot 188 (strain WSA-8) also known as *Rothia* sp. HOT-188 and *Rothia aeria*.

In another embodiment, the composition is formulated for oral delivery (e.g., a capsule, liquid, suspension, tablet, or enteric coated capsule or enteric coated tablet.

In another embodiment, the gluten-degrading enzyme comprises an iso-electric point in a pH range of 2.0-7.0, inclusive or alternatively, in a pH range of 2.5 to 4.0, inclusive.

In another embodiment, the gluten-degrading enzyme comprises a molecular weight between 120-150 kDa, inclusive or between 135-145 kDa, inclusive.

In another embodiment, the gluten-degrading enzyme degrades a gliadin protein or fragment thereof (e.g., a 33-mer peptide of α2-gliadin (e.g., LQLQP-FPQPQLPYPQPQLPYPQPQLPYPQPQPF) (SEQ. ID. NO: 1) or a 26-mer domain derived from γ-gliadin (e.g., FLQPQQPFPQQPQQPYPQQPQQPFPQ) (SEQ. ID. NO: 2)).

In another embodiment, degradation occurs by cleaving the peptide bond after an amino acid sequence selected from the group consisting of -XPQ-, -QQP-, -PPF-, -LYP- and -PFP-. In other embodiments, degradation or digestion occurs by cleaving the peptide bonds after amino acid sequences XPQ and QQP; XPQ and PPF; XPQ and PFP; XPQ and LPY; QQP and LPY; PPF and LPY; PFP and LPY; XPQ, QQP and PPF; XPQ, QQP and PFP; XPQ, QQP and LPY; QQP, PPF, and PFP; XPQ, PPF and PFP; QQP, PPF and LPY; XPQ, PPF and LPY; PY, PPF, and PFP; QQP, PPF and LPY; XPQ, PFP and LPY; XPQ, QQP, PPF and LYP; LYP, QQP, PPF and PFP; XPQ, LYP, PPF and PFP; XPQ, QQP, PFP and LYP; XPQ, QQP, PPF and PFP; or XPQ, QQP, PPF, LPY and PFP.

Also disclosed herein are methods for treating celiac disease or a related disorder, one such method comprising: administering to a subject an effective amount of at least one gluten-degrading enzyme isolated from a *Rothia* species bacteria, wherein the at least one enzyme retains activity at acidic pH and attenuates gluten toxicity in the subject.

In some embodiments, the related disorder is selected from the group consisting of refractory celiac disease, gluten allergy, gluten intolerance, and dermatitis herpetiformis.

In another embodiment, the *Rothia* species is *Rothia* species ot 188 (strain WSA-8) also known as *Rothia* sp. HOT-188 and *Rothia aeria*.

In another embodiment, the at least one gluten-degrading enzyme is administered as an oral formulation.

In another embodiment, the at least one gluten-degrading enzyme is administered just prior to, during or just after consumption of a gluten-containing foodstuff.

In another embodiment, the oral formulation is a capsule, liquid, suspension, tablet, or enteric coated capsule or tablet.

In another embodiment, the gluten-degrading enzyme comprises an iso-electric point in a pH range of 2.0-7.0, inclusive or within a range 2.5-4.0, inclusive (e.g., 2.5, 3, 3.5, 4).

In another embodiment, the gluten-degrading enzyme comprises a molecular weight between 120-150 kDa, inclusive. In another embodiment, the gluten-degrading enzyme comprises a molecular weight of 135-145 kDa, inclusive.

In another embodiment, the gluten-degrading enzyme degrades a gliadin protein or fragment thereof. In another embodiment, the fragment thereof is a 33-mer peptide of α2-gliadin or a 26-mer domain derived from γ-gliadin. In other embodiments, the 33-mer peptide is LQLQP-FPQPQLPYPQPQLPYPQPQLPYPQPQPF (SEQ. ID. NO: 1) and/or the 26-mer domain is FLQPQQP-FPQQPQQPYPQQPQQPFPQ (SEQ. ID. NO: 2).

In another embodiment, degradation occurs by cleaving the peptide bond after an amino acid sequence selected from the group consisting of -XPQ-, -QQP-, -PPF-, -LYP- and -PFP-. In other embodiments, degradation or digestion occurs by cleaving the peptide bonds after amino acid sequences XPQ and QQP; XPQ and PPF; XPQ and PFP; XPQ and LPY; QQP and LPY; PPF and LPY; PFP and LPY; XPQ, QQP and PPF; XPQ, QQP and PFP; XPQ, QQP and LPY; QQP, PPF, and PFP; XPQ, PPF and PFP; QQP, PPF and LPY; XPQ, PPF and LPY; PY, PPF, and PFP; QQP, PPF and LPY; XPQ, PFP and LPY; XPQ, QQP, PPF and LYP; LYP, QQP, PPF and PFP; XPQ, LYP, PPF and PFP; XPQ, QQP, PFP and LYP; XPQ, QQP, PPF and PFP; or XPQ, QQP, PPF, LPY and PFP.

In another embodiment, the enzyme is administered in an admixture with a gluten-containing foodstuff or ingredient thereof. In one embodiment, the enzyme is admixed to the gluten-containing foodstuff during the manufacture of the gluten-containing foodstuff, e.g., in a factory. For example, in the manufacture of wheat-based cereals or wheat-based ramen noodles. In one embodiment, the enzyme is admixed to the gluten-containing foodstuff during the preparation and/or cooking of the food for ingestion, e.g., in a restaurant or in a home setting. For example, in the preparation of a pizza or calzone at a pizzeria.

It is contemplated that the compositions described herein are used for admixture with a gluten-containing foodstuff. The compositions can comprises an isolated enzyme, a plurality of isolated enzymes, an extract from *Rothia* species, a plurality of extracts from more than one *Rothia* species, a *Rothia* species bacteria itself, or a plurality of *Rothia* species bacteria. It is further contemplated that the composition described herein can comprises a mixture of an isolated enzyme, a plurality of isolated enzymes, an extract from *Rothia* species, or a *Rothia* species bacteria.

It is contemplated that the enzyme in the compositions degrades the gluten in the gluten-containing foodstuff or ingredient thereof in vitro. The degradation can be partial or complete. The degree of degradation depends on many factors, e.g., the amount of composition used, the amount of gluten containing foodstuff or ingredient used, the temperature of degradation reaction/environment, the pH of the reaction/environment, the choice of enzyme used etc. One skilled in the art will be able to make adjustment the various factors to achieve the desired final result, i.e., partial or complete degradation. The partially degraded gluten foodstuff can be further degraded in vitro at a later time point, e.g., at a different stage of manufacture of the foodstuff. Alternatively, the partially degraded gluten foodstuff can be further degraded in vivo when a subject ingests the partially degraded food. The subject can be administered a composition and/or enzyme described herein just prior or after ingesting the partially degraded food. In this way, complete degradation takens place in the stomach of the subject.

Also described herein are methods for treating celiac disease or a related disorder, the method comprising administering an isolated enzyme composition or probiotic compositions described herein.

Also provided herein are methods for detoxifying gluten (e.g., in a gluten-containing foodstuff), the method comprising contacting gluten-containing foodstuff with an effective amount of at least one gluten-degrading enzyme isolated from a *Rothia* species bacteria, wherein the at least one enzyme retains activity at acidic pH to cleave a gluten protein, thereby detoxifying gluten.

It is contemplated that the methods for detoxifying gluten comprises contacting gluten-containing foodstuff with an effective amount of an isolated enzyme, a plurality of isolated enzymes, an extract from *Rothia* species, a plurality of extracts from more than one *Rothia* species, a *Rothia* species bacteria itself, or a plurality of *Rothia* species bacteria. It is further contemplated that the contacting comprises a mixture of an isolated enzyme, a plurality of isolated enzymes, an extract from *Rothia* species, or a *Rothia* species bacteria.

In one embodiment, the *Rothia* species is *Rothia* species ot 188 (strain WSA-8) also known as *Rothia* sp. HOT-188 and *Rothia aeria*.

In another embodiment, the gluten-degrading enzyme comprises an iso-electric point in a pH range of 2.0-7.0, inclusive. In another embodiment, the gluten-degrading enzyme comprises an iso-electric point in a pH range of 2.5-4.0, inclusive.

In another embodiment, the gluten-degrading enzyme comprises a molecular weight between 120-150 kDa, inclusive.

In some embodiments, the varying pH is between 2.5 and 10, inclusive or between a pH of 2.8-3.5, inclusive.

In another embodiment, the gluten-degrading enzyme comprises a molecular weight of 135-145 kDa, inclusive.

In another embodiment, the gluten-degrading enzyme degrades a gliadin protein or fragment thereof.

In another embodiment, the fragment thereof is a 33-mer peptide of α2-gliadin or a 26-mer domain derived from γ-gliadin (e.g., the 33-mer peptide is LQLQP-FPQPQLPYPQPQLPYPQPQLPYPQPQPF (SEQ. ID. NO: 1); the 26-mer domain is FLQPQQP-FPQQPQQPYPQQPQQPFPQ (SEQ. ID. NO: 2)).

In another embodiment, degradation occurs by cleaving the peptide bond after an amino acid sequence selected from the group consisting of -XPQ-, -QQP-, -PPF-, -LYP- and -PFP-. In other embodiments, degradation or digestion occurs by cleaving the peptide bonds after amino acid sequences XPQ and QQP; XPQ and PPF; XPQ and PFP; XPQ and LPY; QQP and LPY; PPF and LPY; PFP and LPY; XPQ, QQP and PPF; XPQ, QQP and PFP; XPQ, QQP and LPY; QQP, PPF, and PFP; XPQ, PPF and PFP; QQP, PPF and LPY; XPQ, PPF and LPY; PY, PPF, and PFP; QQP, PFP and LPY; XPQ, PFP and LPY; XPQ, QQP, PPF and LYP; LYP, QQP, PPF and PFP; XPQ, LYP, PPF and PFP; XPQ, QQP, PFP and LYP; XPQ, QQP, PPF and PFP; or XPQ, QQP, PPF, LPY and PFP.

Also provided herein are gluten-free foodstuff compositions, comprising a gluten-containing foodstuff in an admixture with the isolated enzyme described herein in its active form. In other embodiments, the gluten-free foodstuff compositions comprise a gluten-containing foodstuff in an admixture with an isolated enzyme, a plurality of isolated enzymes, an extract from *Rothia* species, a plurality of extracts from more than one *Rothia* species, a *Rothia* species bacteria itself, or a plurality of *Rothia* species bacteria or combinations thereof.

DEFINITIONS

As used herein, the term "treating" or "treatment" with respect to a medical disease or disorder means to stabilize and/or improve the clinical symptoms of a subject afflicted with celiac disease or a related disorder. In one embodiment, "treating" or "treatment" means to relieve or alleviate at least one symptom associated with such condition, or to slow or reverse the progression or anticipated progression of such condition, or bringing about ameliorations of the symptoms of the pathology. Evidence of a therapeutic effect may be any diminution in the severity of disease, particularly as measured by the severity of one or more symptoms such as fatigue, chronic diarrhea, malabsorption of nutrients, weight loss, abdominal distension, anemia, and other symptoms of Celiac Sprue. Other disease indicia include the presence of antibodies specific for glutens, the presence of antibodies specific for tissue transglutaminase, the presence of pro-inflammatory T cells and cytokines, damage to the villus structure of the small intestine as evidenced by histological or other examination, enhanced intestinal permeability, and the like. In some embodiment, effective treatment according to the methods described herein is determined by a reduction in at least one symptom of Celiac Sprue, gluten allergy, gluten intolerance and/or dermatitis herpetiformis by at least 20%, at least 30%, at least 40%, at least 50%, at least 60%, at least 70%, at least 80%, at least 90%, at least 95%, at least 99% or even 100% (e.g., remission or absence of symptoms). In one embodiment, treatment according to the methods and compositions described herein induces a state of remission in celiac disease or a related disorder.

As used herein, the term "treating" or "treatment" with respect to a gluten-containing foodstuff means degrading or digesting the foodstuff to reduce the production of toxic gluten oligopeptides when the foodstuff is subsequently ingested and further digestion by a subject. Preferably the subject is a human. In one embodiment, "treating" or "treatment" of a gluten-containing foodstuff results in complete elimination of toxic gluten oligopeptides when the foodstuff is subsequently ingested and further digestion by a subject. In another embodiment, the "treating" or "treatment" of a gluten-containing foodstuff results in at least 10% reduction of toxic gluten oligopeptides when the foodstuff is subsequently ingested and further digestion by a subject. In other embodiments, the "treating" or "treatment" of a gluten-containing foodstuff results in at least 20%, at least 30%, at least 40%, at least 50%, at least 60%, at least 70%, at least 80%, at least 90%, at least 95%, at least 99% or even 100% reduction of toxic gluten oligopeptides when the foodstuff is subsequently ingested and further digestion by a subject.

As used herein, the term "effective dose" with respect to a medical disease or disorder refers to an amount of a biologically active molecule or conjugate thereof, enzyme, or bacterial formulation (e.g., probiotic formulation) sufficient to exhibit a detectable therapeutic effect, e.g. reduction in the symptoms associated with Celiac sprue, gluten allergy and/or dermatitis herpetiformis, e.g. fatigue, chronic diarrhea, malabsorption of nutrients, weight loss, abdominal distension, anemia, the presence of antibodies specific for tissue transglutaminase, the presence of pro-inflammatory T cells and cytokines, and damage to the villus structure of the small intestines. The specific amount that is therapeutically effective can be readily determined by an ordinary medical practitioner, and can vary depending on factors known in the art, such as, for example, the subject's history and age, the stage of pathological processes, and the administration of other agents or therapeutics that inhibit pathological processes in Celiac sprue, gluten allergy and/or dermatitis herpetiformis.

As used herein, the term "effective dose" or "effective amount" with respect to the treatment of a gluten-containing foodstuff refers to the amount of a biologically active molecule or conjugate thereof, enzyme, or bacterial formulation (e.g., probiotic formulation) sufficient to produce at least 10% reduction of toxic gluten oligopeptides when the foodstuff is subsequently ingested and further digestion by a subject.

As used herein, the term "an extract from a *Rothia* species" refers to a clarified aqueous solution that formerly comprised a *Rothia* species for example, a suspension of *Rothia* species in phosphate buffered saline (PBS) that was agitated for 1 hour at room temperature and then centrifuged at 1000×G for 10 minutes to sediment the bacteria. The supernatant PBS fluid is "an extract from a *Rothia* species". Similarly, a clarified saliva sample is "an extract from a *Rothia* species". "An extract from a *Rothia* species" can also mean a clarified periplasmic extraction of a *Rothia* species, for example, a suspension of *Rothia* species in phosphate buffered saline (PBS) with 20% or 500 mM sucrose and is then agitated for 1 hour at 4° C. and then centrifuged at 1000×G for 10 minutes to sediment the bacteria. In the presence of high sucrose concentration, the bacteria undergo osmotic shock. Such methods of making periplasm extracts are well known to those skilled in the art, e. g. as described in U.S. Pat. No. 5,856,142. "An extract from a *Rothia* species" can also mean a clarified cell lysate of a *Rothia* species, wherein the bacteria are lysed in a suitable buffer and the lysate is centrifuged at 20,000×G for 30 minutes to sediment the cell debris. Ultracentrifugation clarified cell lysate of a *Rothia* species is also "an extract from a *Rothia* species". "An extract from a *Rothia* species" can also mean a chromatography fraction containing a 70 kDa protein or a 140 kDA protein with gluten-degrading activity (e.g., glutamine endopeptidase activity) as assayed by gliadin zymography and other methods described herein.

As used herein, in one embodiment, the term "a glutamine endopeptidase" refers to a proteolytic peptidase that breaks peptide bonds of non-terminal amino acids (i.e. within a protein or peptide molecule) at the -XPQ- or -Xaa-Pro-Gln-triplet sequence and the breakage occurs immediately after the glutamine residue. X or Xaa=any amino acids, P or Pro=proline, and Q or Gln=glutamine (e.g., -YPQ- where Y or Tyr=tyrosine). In another embodiment, a glutamine endopeptidase breaks peptide bonds at either one of the following the -QQP-, -PPF- and -PFP triplet sequences. In other embodiments, a glutamine endopeptidase is capable of breaking several of the -XPQ-, -QQP-, -PPF- and -PFP-triplet sequences. It is also noted that the term "glutamine endopeptidase" encompasses proteases that typically degrade salivary basic proline-rich proteins in saliva, and as such, have glutamine endopeptidase activity to degrade proline-rich glutens.

As used herein, in one embodiment, the term "digest" or "degrade" with respect to a gluten-containing foodstuff, gluten, gliadin or fragment thereof refers to breaking a peptide bond in the protein or peptide molecule in the gluten-containing foodstuff, gluten, gliadin or fragment thereof.

As used herein, the term "acidic pH" refers to pH values less than 7.0 (e.g., 1.0, 1.5, 2.0, 2.5, 3.0, 3.5, 4.0, 4.5, 5.0, 5.5, 6.0, 6.5). As used herein the term "basic pH" refers to pH values greater than 8.0 (e.g., 8.5, 9.0, 9.5, 10.0, 10.5, 11.0, 11.5, 12.0, 12.5, 13.0, 13.5, 14.0). As used herein the term "neutral pH" refers to pH values from 7.0 to 8.0, inclusive (e.g., 7.0, 7.2, 7.4, 7.6, 7.8, 8.0).

As used herein, the term "attenuates gluten toxicity" refers to a decrease in the level of gluten proteins or gluten toxic intermediates (e.g., as measured in a subject having celiac disease and administered a gluten challenge) of at least 20% following treatment with the enzyme compositions described herein compared to an untreated subject; preferably the level of gluten proteins or gluten toxic intermediates are decreased by at least 30%, at least 40%, at least 50%, at least 60%, at least 70%, at least 80%, at least 90%, at least 95%, at least 99%, or even 100% (i.e. no detectable glutens or gluten toxic intermediates).

As used herein, the term "toxic intermediates" refers to gluten protein fragments produced by the digestion of gluten with human digestive enzymes such as trypsin, chymotrypsin, and pepsin, that induce symptoms of celiac disease or a related disorder (see also "toxic gluten oligopeptides" definition herein).

As used herein, the term "related disorder" refers to diseases induced by gluten and include, but are not limited to, gluten intolerance, gluten allergy, refractory celiac disease, and dermatitis herpetiformis.

As used herein, the term "admix" in the context of gluten-containing foodstuff refers to mixing or blending with gluten-containing foodstuff.

As used herein, the term "glutens" refers to a mixture of proteins, including gliadins and glutelins, found in wheat grains, which are not soluble in water and which give wheat dough its elastic texture. "Glutens" also refer to the prolamins that are found in rye, barley, and oats.

As used herein, the term "glutelin" refers to prolamin-like proteins that are found in grass seeds, e. g. wheat, and are soluble in dilute acids or bases, detergents, chaotropic or reducing agents. "Glutelin" tend to be rich in prolines and glutamine.

As used herein, the term "prolamins" refers to a group of plant storage proteins having high proline content and is found in the seeds of cereal grains such as wheat (gliadin), barley (hordein), rye (secalin), corn (zein) and as a minor protein, avenin in oats. They are characterized by a high glutamine and proline content and are generally soluble only in strong alcohol solutions. Some prolamins, notably gliadin from wheat, and similar proteins found in the grass seed of the *Triticeae* species can induce celiac disease in genetically predisposed individuals.

As used herein, the term "gliadin" refers to the alcohol-soluble, glutamine and proline-rich prolamin glycoprotein that is found in wheat. This is one of the proteins that induce celiac disease in genetically predisposed individuals. Examples of gliadin sequences include but are not limited to wheat alpha gliadin sequences, for example as provided in GENBANK accession numbers AJ133612; AJ133611; AJ133610; AJ133609; AJ133608; AJ133607; AJ133606; AJ133605; AJ133604; AJ133603; AJ133602; D84341.1; U51307; U51306; U51304; U51303; U50984; and U08287. A sequence of wheat omega gliadin is set forth in Genbank accession number AF280605.

As used herein, the term "gluten-containing foodstuff" refers to food and/or ingredients of food that has gluten and other proteins found in wheat, barley, and rye. "Gluten-containing foodstuff" also refers to food and/or ingredients of foods that are made of wheat, barley, and rye. It is also contemplated that "gluten-containing foodstuff" can be foodstuff that is merely contaminated with gluten by way of the use of common manufacturing equipment. For example, oats do not contain gluten, however, because oats are a major agricultural product they are handled by the same mills, processing plants, and grain elevators that handle wheat, barley and rye. This results in enough contamination of the oats that they can readily trigger a gluten allergy when ingested. Also included in the term "gluten-containing foodstuff" are formulations of drugs, medications, vitamin supplements or mineral supplements that are contaminated by or prepared using gluten-containing foods such as wheat, barley, or rye.

As used herein, the term "consuming gluten-containing foodstuff" refers to ingesting food made of wheat, rye, and barley, e. g. pizza, cake, bread, etc. as well as ingesting food made with ingredients that are made with wheat, rye, and barley, e. g. soy sauce.

As used herein, the term "diagnosed of Celiac sprue, gluten allergy/gluten intolerance and/or dermatitis herpetiformis" refers to having the symptoms associated with Celiac sprue, gluten allergy and/or dermatitis herpetiformis, e. g. fatigue, chronic diarrhea, malabsorption of nutrients, weight loss, abdominal distension, anemia, the presence of antibodies specific for tissue transglutaminase (ATA), antibodies specific for α/β,γ-gliadin (AGA), the presence of pro-inflammatory T cells and cytokines, and damage to the villus structure of the small intestines.

As used herein, the term "toxic gluten oligopeptides" refers to peptides derived during normal human digestion of gliadins and related storage proteins from dietary cereals, e.g. wheat, rye, barley, and the like. Such oligopeptides act as antigens for T cells in Celiac Sprue. For binding to Class II MHC proteins, immunogenic peptides are usually from about 8 to 20 amino acids in length, more usually from about 10 to 18 amino acids. Such peptides may include PXP motifs, such as the motif PQPQLP (SEQ ID NO: 168). Determination of whether an oligopeptide is immunogenic for a particular patient is readily determined by standard T cell activation and other assays known to those of skill in the art. Other examples of immunogenic gliadin oligopeptides are described in Wieser (1995) Baillieres Clin Gastroenterol 9(2):191-207, incorporated herein by reference. "Toxic gluten oligopeptides" also refers are peptides that comprise known T cell epitopes in gluten, e.g. QLQPFPQPQLPY (SEQ. ID. NO: 3) or PFPQPQLPY (SEQ. ID. NO: 4), PQPQLPYPQPQLPY (SEQ. ID. NO: 5) or PQPQLPYPQ (SEQ. ID. NO: 6), QPQQSFPQQQ (SEQ. ID. NO: 7) or PQQSFPQQQ (SEQ. ID. NO: 8), QLQPFPQPELPY (SEQ. ID. NO: 9), PQPELPYPQPELPY (SEQ. ID. NO: 10), QPQQSFPEQQ (SEQ. ID. NO: 11); IQPQQPAQL (SEQ. ID. NO: 12); QQPQQPYPQ (SEQ. ID. NO: 13); SQPQQQFPQ (SEQ. ID. NO: 14); QQPFPQQPQ (SEQ. ID. NO: 15); or PFSQQQQPV (SEQ. ID. NO: 16), including 33-mer from alpha-gliadin, LQLQPF(PQPQLPY)₃PQPQPF (SEQ. ID. NO: 1), and the 26-mer from gamma-gliadin, FLQPQQPFPQQPQQPYPQQPQQPFPQ (SEQ. ID. NO: 2).

The term "isolated" refers to an enzyme protein which is substantially or essentially free from bacterial components which normally accompany or interact with the enzyme as found in the bacteria. As used herein, the term "isolated" can also refer to mixtures of enzyme proteins comprising a plurality of different enzymes substantially free from bacterial components (e.g., 2, 3, 4, 5, 6, 7, 8, 9, 10, 15, 20 or more different enzymes).

As used herein, the term "inhibited" or "inhibition" when used in the context with the glutamine endopeptidase activity means the reduction of the cleavage of -XPQ-, -QQP-, -PPF- and/or -PFP-containing peptides by at least about 50%, about 60%, about 70%, about 80%, about 90%, about 100% (i.e., level of XPQ-containing peptides is undetectable by standard methods) by any assay described herein or known in the art, wherein X is any amino acid, P is proline and Q is glutamine.

As used herein, the term "gluten degrading activity" with respect to the compositions comprising an isolated enzyme, a plurality of isolated enzymes, an extract from Rothia species, a plurality of extracts from more than one Rothia species, a Rothia species bacteria itself, or a plurality of Rothia species bacteria refers to the capability of the composition to cleave -XPQ-, -QQP-, -PPF- and/or -PFP-containing peptides by at least about 50%, about 60%, about 70%, about 80%, about 90%, about 100% (i.e., level of XPQ-containing peptides is undetectable by standard methods) by any assay described herein or known in the art, wherein X is any amino acid, P is proline and Q is glutamine. In one embodiment, the cleavage is preferably at peptide bonds of non-terminal amino acids (i.e. within a protein or peptide molecule) and the breakage occurs immediately after the glutamine residue for -XPQ- sequence, immediately after the proline residue for -QQP- or -PFP- sequence, and immediately after the phenylalanine residue for -PPF- sequence.

As used herein, the phrase "retain activity in acidic pH environment" or "retain protease activity" refers to an isolated enzyme from Rothia species described herein that is still has gluten degrading activity when the enzyme is in an environment with pH less than 7.0.

As used herein, the term "inclusive" when used with pH or molecular weight of a molecule means that all possible gradation of the pH or molecular weight in contemplated within the specified range. For example, if pH is 3.0 to 4.0 inclusive, then pHs of 3.02, 3.1, 3.14, 3.2, 3.75, 3.99 etc are also contemplated.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in e.g., absorption, carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

BRIEF DESCRIPTION OF THE FIGURES

FIG. 7A. Fragmentation of gliadin 33-mer by oral microbial enzymes in dental plaque. The gliadin peptides were added to plaque suspension in saliva ion buffer ($OD_{620}$ 1.2) to a final concentration of 250 μg/mL and incubated for 5 hours. Samples were analyzed by RP-HPLC, degradation fragments were collected and subjected to LC-ESI-MS/MS. The peptides identified in the individual RP-HPLC fractions were combined. Peptides 1-46 are SEQ. ID. NOS: 17-62 according to the order of appearance.

FIG. 7B. Fragmentation of gliadin 26-mer by oral microbial enzymes in dental plaque as described in FIG. 7A. Peptides 1-53 are SEQ. ID. NOS: 63-115 according to the order of appearance.

FIG. 9A. Sequence similarities between salivary basic proline-rich protein PRB1 and immunotoxic gliadin epitopes. Displayed are selected regions within the basic PRP structures (top sequences, bolded) and gliadin epitopes (underneath). The amino acids that are homologous in the compared sequences are indicated with an asterisk. SEQ. ID. NOS: 120-132 according to the order of appearance.

FIG. 9B. Sequence similarities between salivary basic proline-rich protein PRB2 and immunotoxic gliadin epitopes. Displayed are selected regions within the basic PRP structures (top sequences, bolded) and gliadin epitopes (underneath). The amino acids that are homologous in the compared sequences are indicated with an asterisk. SEQ. ID. NOS: 133-145 according to the order of appearance.

FIG. 9C. Sequence similarities between salivary basic proline-rich protein PRB3 and immunotoxic gliadin epitopes. Displayed are selected regions within the basic PRP structures (top sequences, bolded) and gliadin epitopes (underneath). The amino acids that are homologous in the compared sequences are indicated with an asterisk. SEQ. ID. NOS: 146-151 according to the order of appearance.

FIG. 13. LC-ESI-MS/MS analysis of proteins in DEAE-P1A-HIC-P3. Three proteins were identified.

FIG. 14. *Rothia mucilaginosa* 25296 proteases predicted from MEROPS website (See the Sanger Genome sequencing website).

FIG. 15. Tat pathway signal sequence domain protein from *Rothia mucilaginosa* ATCC 25296. NCBI Reference Sequence: ZP_05367032.1, SEQ. ID. NO: 162.

FIG. 16. Hypothetical protein ROTMU0001_0500 predicated from *Rothia mucilaginosa* ATCC 25296 genome sequencing. NCBI Reference Sequence: ZP_05367744.1, SEQ. ID. NO: 163.

FIG. 17. Hypothetical protein ROTMU0001_1834 predicated from *Rothia mucilaginosa* ATCC 25296 genome sequencing. NCBI Reference Sequence: ZP_05367238.1, SEQ. ID. NO: 164.

DETAILED DESCRIPTION

Figure 1A:
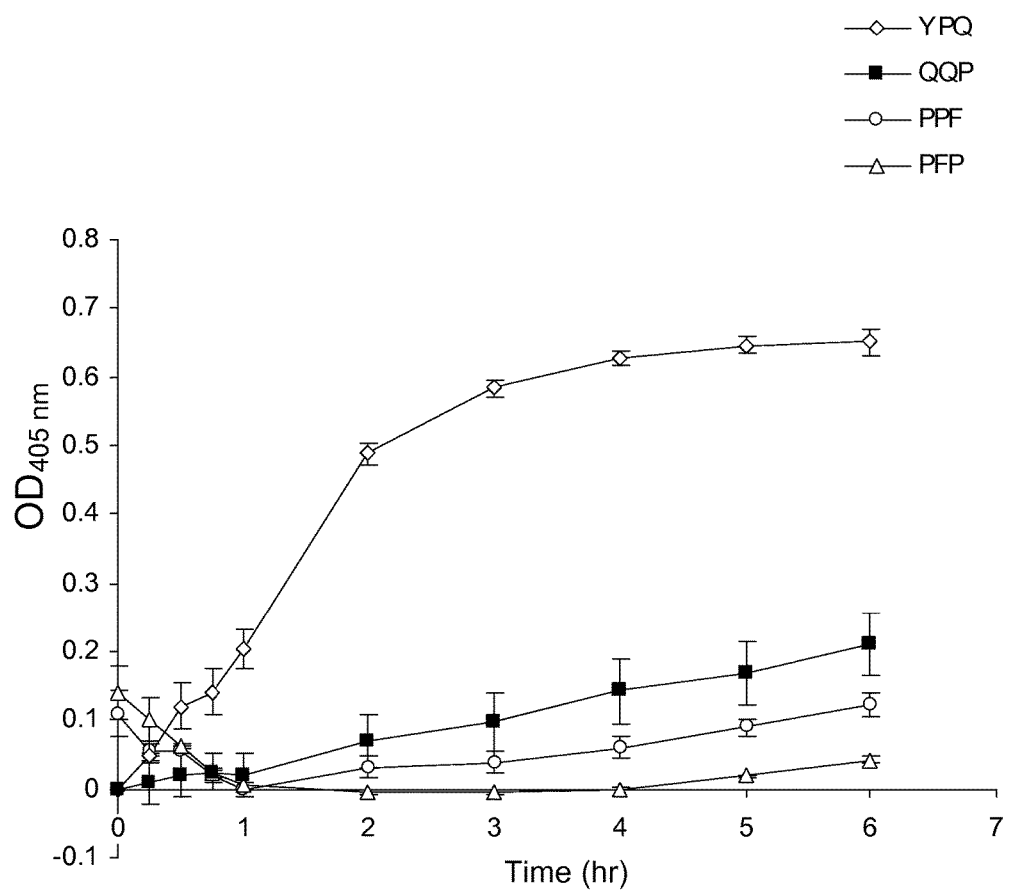
FIGS. 1A-1B. Hydrolysis of gliadin-derived enzymatic substrates. Dental plaque was suspended in saliva ion buffer to an $OD_{620}$ of 1.2. Substrates Z-YPQ-pNA, Z-QQP-pNA, Z-PPF-pNA and Z-PFP-pNA were added to final concentrations of 200 μM. Substrate conversion was monitored spectrophotometrically at 405 nm. 1 A, hydrolysis measured during the 0-6 hr time interval; 1B, hydrolysis measured after 6 h, 24 h and 48 h. Notably, an OD of 0.6-0.7 indicates complete hydrolysis.

Described herein are gluten-degrading enzyme compositions derived from *Rothia* species bacteria that retain activity at acidic pH, as well as uses thereof in the treatment of celiac disease or a related disorder. The methods and compositions described herein are advantageous over other *Rothia* species enzyme compositions in that they retain gluten-degrading activity over a wide range of pH and thus, are active throughout the digestive tract of a subject diagnosed with celiac disease or a related disorder.

Accordingly, in one embodiment, provided herein is a composition comprising isolated enzymes derived from *Rothia* species bacteria, more specifically comprising at least one gluten-degrading enzyme isolated from a *Rothia* species bacteria, wherein the at least one enzyme retains protease activity at an acidic pH of 3.0 assayed in an in vitro gliadin degradation assay using a synthetic substrate Z-YPQ-pNA, and wherein the at least one enzyme comprises an iso-electric point in a pH range of 2.0-7.0, inclusive.

In one embodiment, provided herein is a probiotic composition comprising an effective amount of *Rothia* species bacteria comprising at least a gluten-degrading enzyme that retains protease activity at acidic pH of 3.0 in an in vitro gliadin degradation assay using a synthetic substrate Z-YPQ-pNA, and wherein the at least one enzyme and comprises an iso-electric point in a pH range of 2.0-7.0, inclusive, and a pharmaceutically acceptable carrier.

In one embodiment, provided herein is a method for treating celiac disease or a related disorder, the method comprising administering to a subject an effective amount of at least one gluten-degrading enzyme isolated from a *Rothia* species bacteria, wherein the at least one enzyme retains protease activity at acidic pH of 3.0 in an in vitro gliadin degradation assay using a synthetic substrate Z-YPQ-pNA, and wherein the at least one enzyme comprises an iso-electric point in a pH range of 2.0-7.0, inclusive, and attenuates gluten toxicity in the subject.

In another embodiment, provided herein is a method for treating celiac disease or a related disorder, the method comprising administering the isolated enzyme composition and/or the probiotic composition described herein.

In one embodiment, provided herein is a method for detoxifying gluten, the method comprising contacting gluten-containing foodstuff with an effective amount of at least one gluten-degrading enzyme isolated from a *Rothia* species bacteria to cleave a gluten protein and thereby detoxifying gluten, wherein the at least one enzyme retains protease activity at acidic pH of 3.0 in an in vitro gliadin degradation assay using a synthetic substrate Z-YPQ-pNA, and wherein the at least one enzyme comprises an iso-electric point in a pH range of 2.0-7.0, inclusive.

In another embodiment, provided herein is a method for detoxifying gluten, the method comprising contacting gluten-containing foodstuff with an effective amount of the isolated enzyme composition and/or the probiotic composition described herein.

In another embodiment, provided herein is a method for degrading gluten in gluten-containing foodstuff prior to ingestion by a subject, the method comprises contacting the gluten-containing foodstuff with an effective amount of at least one gluten-degrading enzyme isolated from a *Rothia* species bacteria, wherein the at least one enzyme retains protease activity at acidic pH of 3.0 in an in vitro gliadin degradation assay using a synthetic substrate Z-YPQ-pNA, and wherein the at least one enzyme comprises an iso-electric point in a pH range of 2.0-7.0, inclusive.

In another embodiment, provided herein is a method for degrading gluten in gluten-containing foodstuff prior to ingestion by a subject, the method comprises contacting the gluten-containing foodstuff with the isolated enzyme composition and/or the probiotic composition described herein.

In one embodiment, provided herein is a gluten-free foodstuff composition comprising a gluten-containing foodstuff in an admixture with at least one gluten-degrading enzyme isolated from a *Rothia* species bacteria, wherein the at least one enzyme retains protease activity at acidic pH of 3.0 in an in vitro gliadin degradation assay using a synthetic substrate Z-YPQ-pNA, and wherein the at least one enzyme comprises an iso-electric point in a pH range of 2.0-7.0, inclusive.

In one embodiment, provided herein is a gluten-free foodstuff composition comprising a gluten-containing foodstuff in an admixture with the isolated enzyme composition and/or the probiotic composition described herein.

In one embodiment, the *Rothia* species is *Rothia* species ot 188, also known as *Rothia* sp. HOT-188 and *Rothia aeria* (strain WSA-8).

In one embodiment, the composition is an oral formulation, such as in the form of a capsule, liquid, tablet, suspension, or enteric coated capsule or tablet.

In one embodiment, the composition is formulated for treatment of celiac disease or a related disorder in a subject In one embodiment, the composition is formulated for treatment of a gluten-containing foodstuff prior to ingestion by a subject having celiac disease or a related disorder, wherein the gluten-containing foodstuff is degraded in vitro.

In one embodiment, the at least one gluten-degrading enzyme, the isolated enzyme composition and/or the probiotic composition is administered in an admixture with a gluten-containing foodstuff for the purpose of degrading the gluten in the food. In one embodiment, the enzyme is admixed with the ingredients during the manufacture of the food. In one embodiment, the enzyme is admixed with the ingredients during the preparation and/or cooking of the food.

In one embodiment, the isolated enzyme retains activity in the admixture.

In one embodiment, the gluten-containing foodstuff is degraded partially prior to ingestion by the subject.

In another embodiment, the gluten-containing foodstuff is degraded completely prior to ingestion by the subject.

In one embodiment, the iso-electric point of the enzyme is in a pH range of 2.0-4.0, inclusive.

In one embodiment, the at least one enzyme comprises a molecular weight between 120-150 kDa, inclusive.

In one embodiment, the at least one enzyme comprises a molecular weight of 135-145 kDa, inclusive.

In one embodiment, the at least one enzyme comprises a molecular weight between 50 and 90 kDa, inclusive.

In one embodiment, the at least one enzyme comprises a molecular weight between 65 and 75 kDa, inclusive.

In other embodiment, the acidic pH in which the enzyme retains activity can vary between 2.5 and 5.0, inclusive.

In one embodiment, the pH is a pH of 2.5-3.0, inclusive.

In one embodiment, the at least one enzyme degrades a gliadin protein or fragment thereof.

In one embodiment, the fragment thereof is a 33-mer peptide of α2-gliadin or a 26-mer domain derived from γ-gliadin.

In one embodiment, the 33-mer peptide is (SEQ. ID. NO: 1)
LQLQPFPQPQLPYPQPQLPYPQPQLPYPQPQPF.

In one embodiment, the 26-mer domain is FLQPQQP-FPQQPQQPYPQQPQQPFPQ (SEQ. ID. NO: 2).

In some embodiments, the degradation of gluten-containing foodstuff occurs by cleaving the peptide bond after an amino acid sequence selected from the group consisting of -XPQ- -QQP-, -PPF-, and/or -PFP-. In one embodiment, the amino acid sequence is -XPQ-.

In one embodiment, the method of treatment of celiac disease or related disorder further comprises selecting a subject who has been diagnosed or been suspected of suffering from the disease.

In one embodiment, the celiac related disorder is selected from the group consisting of refractory celiac disease, gluten allergy, gluten intolerance, and dermatitis herpetiformis.

In one embodiment, the at least one gluten-degrading enzyme, the isolated enzyme composition and/or the probiotic composition is administered to the subject as an oral formulation.

In one embodiment, the at least one gluten-degrading enzyme, the isolated enzyme composition and/or the probiotic composition is administered just prior to, during or just after consumption of a gluten-containing foodstuff.

Due to the close similarity of human saliva-derived basic PRPs and wheat-derived gliadins, and the proline and glutamine rich peptides produced upon digestion, the PRPs can potentially act as gluten-like proteins and cause celiac disease. In one embodiment, provided herein is a method of assessing whether a subject has or is likely to develop celiac disease or related disorder, the method comprising providing a peptide profile of the salivary basic proline rich protein (PRP) from the subject and comparing the profile with that of a normal healthy subject who does not have celiac disease or related disorder, wherein if the query peptide profile is at least 10% different from that of the healthy subject indicates that the likelihood that the subject has or is likely to develop celiac disease or related disorder. Methods of peptide profiling are well in the art, e.g., by liquid chromatography and mass spectrometry.

Figure 9B:
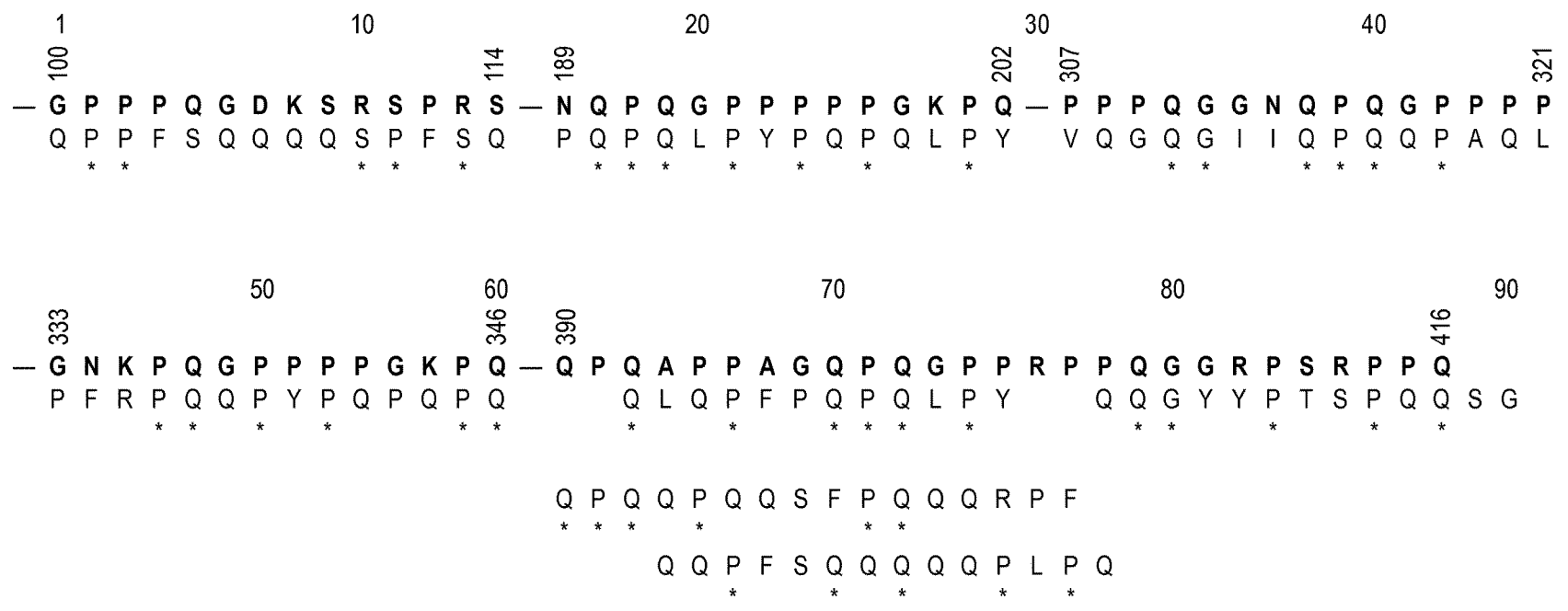
Figure 9C:
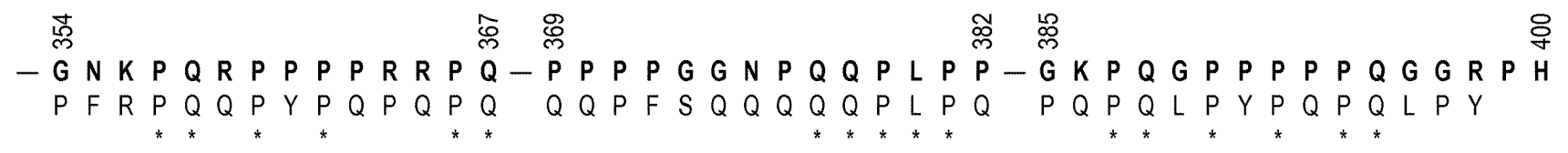
Figure 9D:
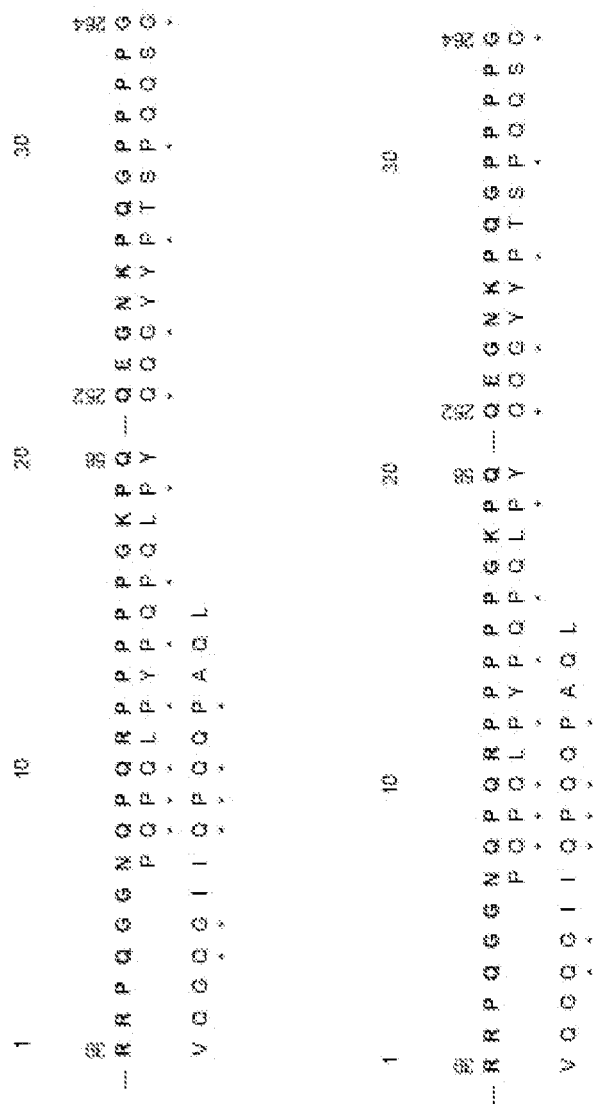
FIG. 9D. Sequence similarities between salivary basic proline-rich protein PRB4 and immunotoxic gliadin epitopes. Displayed are selected regions within the basic PRP structures (top sequences, bolded) and gliadin epitopes (underneath). The amino acids that are homologous in the compared sequences are indicated with an asterisk. SEQ. ID. NOS: 152-161 according to the order of appearance.
Figure 10:
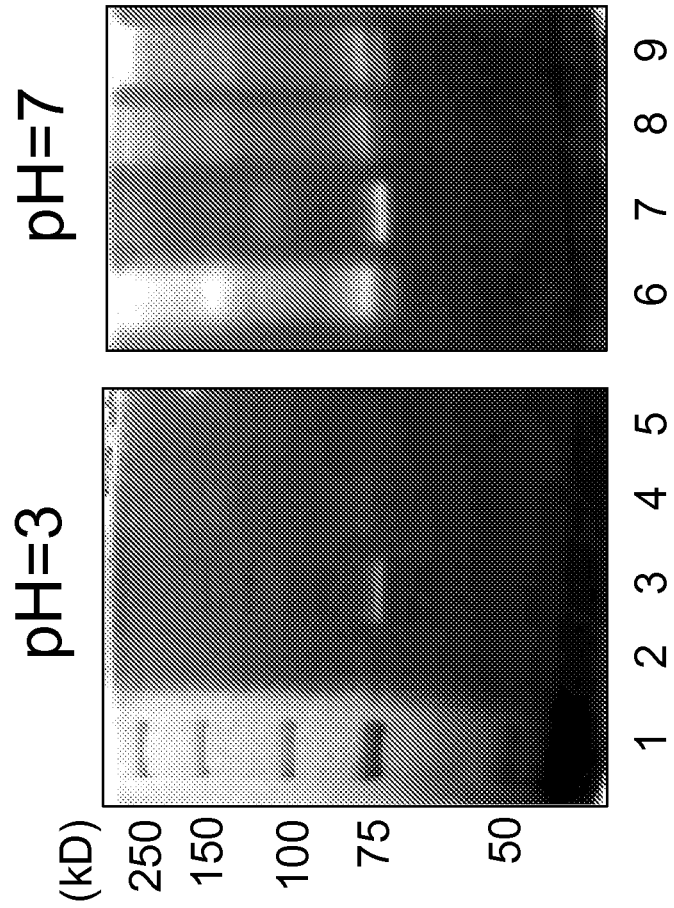
FIG. 10. Gliadin zymography (6%) of *Rothia* strains developed at low and neutral pH. Per lane 150 μL cells ($OD_{620}$=5.0) were loaded. Lane 1, MW standard, lanes 2 and 6, strain WSA-2B (*Rothia mucilaginosa*); lanes 3 and 7: strain WSA-8 (*Rothia* spp. ot 188), lanes 4 and 8: strain WSA-26 (*Rothia mucilaginosa*); lanes 5 and 9: *Rothia mucilaginosa* (ATCC 25296). After electrophoresis, the gel was cut in the middle and one half was renatured and developed at pH=3, the WSA-8 protease remained active whereas the other *Rothia* strains display no activity at this pH.

In one embodiment, the comparison is made with regard to the 42 peptide sequences described in FIG. 9. In one embodiment, the query peptide profile identifies and/or quantifies these 42 peptide sequences. In one embodiment, when at least 10% of the 42 peptide sequences are detected in the query peptide profile of the subject indicates the likelihood that the subject has or is likely to develop celiac disease or related disorder. In other embodiments, at least 20%, at least 30%, at least 40%, at least 50%, at least 60%, at least 70%, at least 80%, at least 90%, at least 95%, at least 99% or even 100% of the 42 peptide sequences are detected in the query peptide profile of the subject.

In another embodiment, when at least 10% of the 42 peptide sequences are detected and the levels are at least 10% higher in the query peptide profile of the subject compared to a healthy subject indicates the likelihood that the subject has or is likely to develop celiac disease or related disorder. In other embodiments, at least 20%, at least 30%, at least 40%, at least 50%, at least 60%, at least 70%, at least 80%, at least 90%, at least 95%, at least 99% or even 100% of the 42 peptide sequences are detected in the query peptide profile of the subject and the levels of the peptides are at least 20%, at least 30%, at least 40%, at least 50%, at least 60%, at least 70%, at least 80%, at least 90%, at least 95%, at least 99% or even 100% higher than those of the 42 peptides in a healthy subject.

In another embodiment, when the peptides in the prolife in the query peptide profile of the subject are at least 10% higher than those of a healthy subject, this indicates that the likelihood that the subject has or is likely to develop celiac disease or related disorder. In other embodiments, the levels of the peptides are at least 20%, at least 30%, at least 40%, at least 50%, at least 60%, at least 70%, at least 80%, at least 90%, at least 95%, at least 99% or even 100% higher than those of the 42 peptides in a healthy subject.

In some embodiments, the PRP can serve in a positive way, e.g. by inducing tolerance to gluten. The PRP or the 42 peptides disclosed in FIG. 8 can be administered to a subject to inducing tolerance to gluten.

Celiac Disease and Related Disorders

The gastrointestinal (GI) tract consists of distinct but connected anatomical regions, comprising the oral cavity, the oesophagus, the stomach, the small and the large intestine (DeSesso J M, and Jacobson C F. *Food Chem Toxicol* 2001; 39:209-28). The oral microbiome is described in Dewhirst et al., J Bacteriol. 2010, 192:5002-17. The entire GI tract is colonized with microorganisms with colonization levels showing a gradient being lowest in the stomach and increasing in density toward the proximal and distal ends. The proximal region, the oral cavity, provides a rich environment for bacterial colonization as it contains a variety of different habitats and ecological niches. It harbors over 600 different types of bacteria belonging to 141 different taxa representing 6 different bacterial phyla, including the Firmicutes, Actinobacteria, Proteobacteria, Bacteroidetes, Fusobacteria and the TM7 phylum (Aas J A, et al. *J Clin Microbiol* 2005; 43:5721-32; Paster B J, et al. *J Bacteriol* 2001; 183:3770-83). The distal GI microbiome is likewise phylogenetically diverse with members representing at least 9 different phyla (Eckburg P B, et al. *Science* 2005; 308: 1635-8; Frank D N, et al. *Proc Natl Acad Sci USA* 2007; 104:13780-5).

The GI tract is considered a "super organ" with functions contributed by human as well as bacterial genes (Camp J G, et al. *Gastroenterology* 2009; 136:1989-2002; Turnbaugh P J, et al. *Nature* 2006; 444:1027-31). Most GI-colonizing microorganisms live in symbiosis with the host. The mutually beneficial relationship between the host and its colonizers is most evident in aspects related to digestion. Complex carbohydrates that cannot be degraded by the arsenal of human digestive enzymes can in most cases be hydrolyzed by bacterial glycosidases. For instance, bacteria belonging to the *Bacteroides* genus, turn the non-digestable polysaccharides into small chain fatty acids that are subsequently metabolized by the host (Turnbaugh P J, et al. *Nature* 2006; 444:1027-31). Ingested proteins are in part degraded by host proteolytic enzymes such as pepsin, elastase, carboxypeptidase, trypsin, and chymotrypsin converting them into oligopeptides and single amino acids which can then enter the enterocyte via selective transporters and be further metabolized or transported (Daniel H. *Annu Rev Physiol* 2004; 66:361-84). Evidently, this mechanism is contingent upon the susceptibility of the substrate proteins to digestion by host enzymes.

Examples of dietary proteins that are difficult to digest by host proteolytic enzymes are glutens. Gluten proteins, comprising gliadins and glutenins, are abundantly contained in dietary products made of wheat, barley and rye (Wieser H. *Food Microbiol* 2007; 24:115-9). They are unusual with respect to their high content of the amino acids proline and glutamine, which are largely resistant to cleavage by the major human GI digestive enzymes (e.g., pepsin, trypsin, chymotrypsin). Thus pepsin or trypsin are unable to cleave the peptide bonds C-terminal to these residues (Siegel M, et al. *Chem Biol* 2006; 13:649-58). The proteolytic resistance of some highly T cell stimulatory gluten-derived peptides that reach the duodenum, e.g. a 33-mer peptide from α2-gliadin and a 26-mer peptide from γ-gliadin, is paradigmatic for the inability of the human body to thoroughly digest gluten, resulting in the destructive immunological responses in the proximal intestine of patients with celiac disease (Koning F, et al. *Best Pract Res Clin Gastroenterol* 2005; 19:373-87; Jabri B, and Sollid L M. *Nat Clin Pract Gastroenterol Hepatol* 2006; 3:516-25; Schuppan D, et al., *Gastroenterology* 2009; 137:1912-33).

Celiac sprue, also known as celiac disease, gluten-sensitive enteropathy, and gluten-induced enteropathy, is a chronic disease of the digestive tract that interferes with the digestion and absorption of nutrients from food. People with celiac sprue cannot tolerate gluten. Celiac disease is an inherited, autoimmune disease in which the lining of the small intestine is damaged from eating gluten and other proteins found in wheat, barley, rye, and gluten-contaminated oats. There is a propensity of Celiac disease in individuals who possess the HLA-DQ8 class II antigen receptor gene. The exact cause of celiac disease is unknown although it is believed that intestinal damage is caused by interactions between specific gliadin oligopeptides and the HLA-DQ2, DQ2.5, DQ2.2/DQ7 or DQ8 antigen, which in turn induce proliferation of T lymphocytes in the sub-epithelial layers. T helper 1 cells and cytokines can play a major role in a local inflammatory process leading to villus atrophy of the small intestine. The intestines contain projections, called villi that absorb nutrients. The lining villi become damaged due to the body's immune reaction. In undiagnosed or untreated celiac disease, these villi become flattened. Because the lining of the intestine contains essential enzymes for digestion and absorption, its destruction leads to malabsorption, a difficulty in absorption of food and essential nutrients. As a result, Celiac sprue is often considered a malabsorption disorder. This affects the ability to absorb nutrients properly. The disease can develop at any point in life, from infancy to late adulthood. Those with a family member with celiac disease are at greater risk for developing the disease. The disorder is most common in Caucasians and those of European ancestry and women are affected more commonly than men.

The symptoms of celiac disease can vary significantly from person to person. This is part of the reason the diagnosis is frequently delayed. For example, one person may have constipation, a second may have diarrhea, and a third may have no irregularity in stools. A non-limiting list of gastrointestinal symptoms include abdominal pain, abdominal distention, bloating, gas, indigestion, constipation, decreased appetite that may also be increased or unchanged, diarrhea, chronic or occasional lactose intolerance which is common upon diagnosis, but usually goes away following treatment, nausea and vomiting, stools that float, are foul smelling, bloody, or "fatty", and unexplained weight loss although people can be overweight or of normal weight upon diagnosis.

A non-limiting list of non-intestinal symptoms include anemia (low red blood cell count), bone and joint pain, bone disease such as osteoporosis, kyphoscoliosis, and fracture, breathlessness due to anemia, bruising easily, dental enamel defects and discoloration, depression, fatigue, growth delay in children, hair loss, hypoglycemia, irritability and behavioral changes, malnutrition, mouth ulcers, muscle cramps, nosebleeds, seizures, short stature, unexplained skin disorders (dermatitis herpetiformis), swelling which can be general or abdominal, and vitamin or mineral deficiency which can include single or multiple nutrient (for example, iron, folate, vitamin K).

There is currently no treatment for celiac disease except the advice to follow a lifelong gluten-free diet, which allows the intestinal villi to heal. Patients are advised to eliminate foods, beverages, and medications that contain wheat, barley, rye, and in some cases oats. The health care provider may prescribe vitamin and mineral supplements to correct nutritional deficiencies. Occasionally, corticosteroids (such as prednisone) may also be prescribed for short-term use or in patients suffering from refractory sprue. Following a well-balanced, gluten-free diet is generally the only treatment needed to stay well.

The current diagnosis method includes a complete blood count (CBC) to detect signs of anemia, testing for an increase in alkaline phosphatase level which may indicate bone loss, testing for low cholesterol and albumin levels which may be signs of malabsorption and malnutrition, testing for an increase in liver enzymes and abnormal blood clotting, and detection of specific antibodies to tissue transglutaminase and gliadin. The health care provider will order these antibody tests if Celiac sprue is suspected. If the tests are positive, upper endoscopy is usually performed to sample a piece of tissue (biopsy) from the first part of the small intestine (duodenum). An endoscopy with enteroscopy, particularly of the lower sections of the intestine most commonly affected, will show a flattening of the villi. A follow-up biopsy or blood work may be ordered several months after the diagnosis and treatment to confirm the disease. Normal results mean that the patient has responded to treatment, thereby confirming the diagnosis.

In one embodiment, the subject treated according to the methods and compositions described herein has been diagnosed with Celiac Sprue, gluten allergy/gluten intolerance and/or dermatitis herpetiformis. In another embodiment, the subject is a mammal, preferably a human. Current diagnosis methods for Celiac sprue include but are not limited to one or more of serological tests, e.g. anti-gliadin antibodies, anti-transglutaminase antibodies, anti-endomysial antibodies; endoscopic evaluation, e.g. to identify celiac lesions;

histological assessment of small intestinal mucosa, e.g. to detect villous atrophy, crypt hyperplasia, infiltration of intraepithelial lymphocytes; and any GI symptoms dependent on inclusion of gluten in the diet.

Gluten-Degrading Enzymes

The gluten-degrading enzymes useful with the methods and compositions described herein are derived from *Rothia* species bacteria and retain gluten-degrading activity throughout a wide range of pH (e.g., pH 3.0-10). Accordingly, in some embodiments, the glutamine endopeptidase enzymes of a *Rothia* species described herein is capable of cleaving of any of the following peptides, including known T cell epitopes in gluten, under optimal conditions: QLQPFPQPQLPY (SEQ. ID. NO: 3) or PFPQPQLPY (SEQ. ID. NO: 4), PQPQLPYPQPQLPY (SEQ. ID. NO: 5) or PQPQLPYPQ (SEQ. ID. NO: 6), QPQQSFPQQQ (SEQ. ID. NO: 7) or PQQSFPQQQ (SEQ. ID. NO: 8), QLQPFPQPELPY (SEQ. ID. NO: 9), PQPELPYPQPELPY (SEQ. ID. NO: 10), QPQQSFPEQQ (SEQ. ID. NO: 11); IQPQQPAQL (SEQ. ID. NO: 12); QQPQQPYPQ (SEQ. ID. NO: 13); SQPQQQFPQ (SEQ. ID. NO: 14); QQPFPQQPQ (SEQ. ID. NO: 15); or PFSQQQQPV (SEQ. ID. NO: 16), including 33-mer from alpha-gliadin, LQLQPF(PQPQLPY)3PQPQPF (SEQ. ID. NO: 1), and the 26-mer from gamma-gliadin, FLQPQQPFPQQPQQPYPQQPQQPFPQ (SEQ. ID. NO: 2). In some embodiments, the glutamine endopeptidase of a *Rothia* species described herein have a kcat/Km of at least about 2.5 s$^{-1}$ M$^{-1}$, usually at least about 250 s$^{-1}$ M$^{-1}$ and preferably at least about 25000 s$^{-1}$ for cleaving of any of the peptides described herein. A glutamine endopeptidase of a *Rothia* species described herein have a specificity kcat/Km>2 mM$^{-1}$ s$^{-1}$ for the quenched fluorogenic substrate Abz-QPQQP-Tyr(NO2)-D (SEQ ID NO: 169). Methods of assaying such enzymatic activities are known to those skilled in the art, e. g. by HPLC or fluorescence spectroscopy and as described, for example, in U.S. Pat. No. 7,534,426. For fluorescence spectroscopy-based assays, suitable fluorophores can be attached to the amino- and carboxy-termini of the peptides.

The gluten-degrading enzymes described herein are isolated enzymes, extracts, or enriched extracts derived from *Rothia* species bacteria (e.g., *Rothia* spp. of 188, also known as *Rothia* sp. HOT-188 and *Rothia aeria*). Such gluten-degrading enzymes can be, in one embodiment, a glutamine endopeptidase enzyme (e.g., a metal-ion dependent serine protease). In one embodiment, the glutamine endopeptidase enzyme present in the extract, derived or isolated from a *Rothia* species bacteria is inhibited by 1 mM 1-10 Phenanthroline. Addition of the serine protease inhibitor, phenylmethanesulphonylfluoride or phenylmethylsulphonyl fluoride (PMSF) can also inhibit YPQ, QQP, PPF and/or PFP cleavage activity, indicating that the enzyme is a serine protease. In one embodiment, the glutamine endopeptidase enzyme present in the extract, derived or isolated from a *Rothia* species bacterium is inhibited by 0.1-1 mM PMSF. In one embodiment, the glutamine endopeptidase enzyme present in the extract, derived or isolated from a *Rothia* species bacterium is inhibited by 0.1-1 mM 4-(2-Aminoethyl) benzenesulfonyl fluoride hydrochloride (AEBSF).

In one embodiment, the glutamine endopeptidase enzyme is isolated from a *Rothia* species bacterium by conventional protein purification methods known to those skilled in the art, e. g. as described in the Current Protocols in Molecular Biology and the Current Protocols in Protein Sciences. The protein fraction of an extract from a *Rothia* species bacterium can be concentrated by ammonium sulphate precipitation, and then purified by ion exchange chromatography on DEAE SEPHAROSE® CL-6B and gel filtration on SEPHADEX® G-100. Sample fractions are taken at each step and assayed for -XPQ-, -QQP-, -PPF- and/or -PFP- cleavage activity in order to follow the location of the enzyme. For example, the enzyme can be at least 20% pure, at least 35% pure, at least 45% pure, at least 55% pure, at least 65% pure, at least 75% pure, at least 85% pure, at least 95% pure, at least 95% pure, at least 99% pure, wherein all the percentages between 20 and 99 are explicitly included.

The enzyme or enzymes can be further purified, for example, from the 70 kDa fraction using standard purification schemes known in the art, e. g. size exclusion chromatography to isolate the 70 kDa fraction from a clarified crude extract of a *Rothia* species bacteria cell lysate. The bacteria can be lysed by standard methods known in the art, e. g. with lysozymes and treatment in a par bomb. The lysate can then be clarified by ultracentrifugation at 100,000×G force for 1 hour at 4° C. The clarified lysate can then be concentrated and then fractioned with commercially available gel filtration matrix such as SEPHACRYL® (S-100/200/300/400/500) from GE Healthcare Life Sciences. Fractions with glutamine endopeptidase activity can be determined by methods known in the art and those described herein. One skilled in the art will be able to make minor modification for the enzyme being studied.

In one embodiment, the glutamine endopeptidase enzyme attenuates gluten toxicity by cleaving the peptide bond after glutamine at -XPQ- motifs in gluten-containing foodstuff, wherein X=any amino acids, P=proline, and Q=glutamine. In one embodiment, the cleavage is at peptide bonds of non-terminal amino acids (i.e. within a protein or peptide molecule) immediately after the proline residue for -QQP- or -PFP- sequence, and immediately after the phenylalanine residue for -PPF- sequence.

Acidic Gluten-Degrading Enzymes from *Rothia* Species Bacteria

The enzymes described herein have a significant advantage over other microbial enzymes that degrade gluten due to their acidic character and ability to retain protease activity at varying pH (e.g., pH 3 to 10) including acidic pHs, such as those found in the stomach. The enzymes described herein have an isoelectric focusing point pH fractions of pH2.5, 3 and 4. In the most acidic fraction (tested as described herein in the Examples section) a high molecular weight protease of approximately 140 kD can be isolated for use with the methods as described herein. Several 70 kD gluten-degrading enzymes for use with the methods described herein have an isoelectric focusing point within the range of pH 3 to 4. Thus, the gluten-degrading enzymes for use with the methods and compositions described herein are primarily acidic in nature.

Another advantage of the enzymes described herein is that they retain gluten-degrading activity throughout a wide range of pH (e.g., 3-10). As used herein, the term "retains gluten-degrading activity" or "retains activity" means that an enzyme as described herein retains at least 20% of the gluten-degrading activity (as measured by e.g., an in vitro gliadin or gliadin peptide cleavage assay as described in e.g., the Examples section) measured at a range of test pHs (e.g., in particular acidic pHs of 2.5-5.0) compared to the activity measured at the environmental pH for the enzyme (e.g., pH 7-8 or the native pH environment in which the enzyme is found); preferably the enzyme retains at least 30%, at least 40%, at least 50%, at least 60%, at least 70%, at least 80%, at least 90%, at least 95%, at least 99%, or even 100% of the activity compared to the activity measured when the assay is conducted at the enzyme's environmental pH (e.g., pH 7-8).

The ability of the enzymes described herein to retain gluten-degrading activity over a wide range of pH permits the enzyme to remain active throughout the varying pH environment of the gastrointestinal tract. This is particularly useful when the composition is administered within one hour of ingestion of a gluten-containing foodstuff by a subject. For example, it is contemplated herein that the isolated enzyme is taken prior to ingestion (e.g., 20 min to 1 h before), concomitant with ingestion (e.g., at the same time), or shortly after ingestion (e.g., 20 min to 1 h after) of a gluten-containing foodstuff. The enzymes described herein can transit the gastrointestinal tract with the gluten-containing foodstuff and can de-toxify gluten or fragments thereof that are formed during digestion. Since the enzymes are active at pHs observed in essentially every region of the gastrointestinal tract (e.g., oral cavity, stomach, small intestine etc), the enzymes described herein will have a higher efficiency for degrading gluten than a comparable enzyme that is inactivated by low pH (e.g., stomach pH). As used herein, the term "higher efficiency for degrading gluten" means that at least 20% more gluten will be degraded during passage through the gastrointestinal tract by the enzymes described herein (as measured by appearance of gluten degradation products or by a more favorable response of a subject to a gluten challenge) compared to an enzyme having similar activity but that does not operate at a wide range of pH (e.g., only works within a narrow pH range of 7-8); preferably at least 30% more, at least 40% more, at least 50% more, at least 60% more, at least 70% more, at least 80% more, at least 90% more, at least 95% more, at least 99% more, at least 1-fold more, at least 2-fold more, at least 5-fold more, at least 10-fold more, at least 20-fold more, at least 100-fold more, at least 200-fold more, at least 500-fold more, at least 1000-fold more gluten is degraded during passage through the gastrointestinal tract by the enzymes described herein that retain activity at a wide range of pH.

The enzymes described herein and compositions thereof are advantageous over previous gluten-degrading enzymes described in saliva, since they do not require enteric coating to permit transit through the GI tract while retaining gluten-degrading activity.

In one embodiment, the enzyme described herein retains protease activity at pH 2.5. In one embodiment, the enzyme described herein retains protease activity at pH 3.0. In another embodiment, the enzyme described herein retains protease activity up to pH 7.0. In one embodiment, the enzyme described herein retains protease activity between pH 2.5 to 7.0. In some embodiments, the enzyme described herein retains protease activity between pH 2.5 to 3.0, between pH 2.5 to 4.0, between pH 3.0 to 4.0, between pH 3.0 to 6.0, between pH 2.5 to 5.0, between pH 2.5 to 6.0, between pH 5.0 to 7.0, between pH 5.0 to 6.0, and between pH 6.0 to 7.0.

In one embodiment, the enzyme described herein exhibits protease activity at pH 3.0 after 3-4 hours of digestion, e.g., in an in vitro gliadin degradation assay using a synthetic substrate Z-YPQ-pNA described herein. In one embodiment, the enzyme described herein exhibited at least 5% protease activity at pH 3.0 after 3-4 hours of digestion in comparison the activity observed when assayed at pH 8.0 for 3-4 hours.

Figure 6:
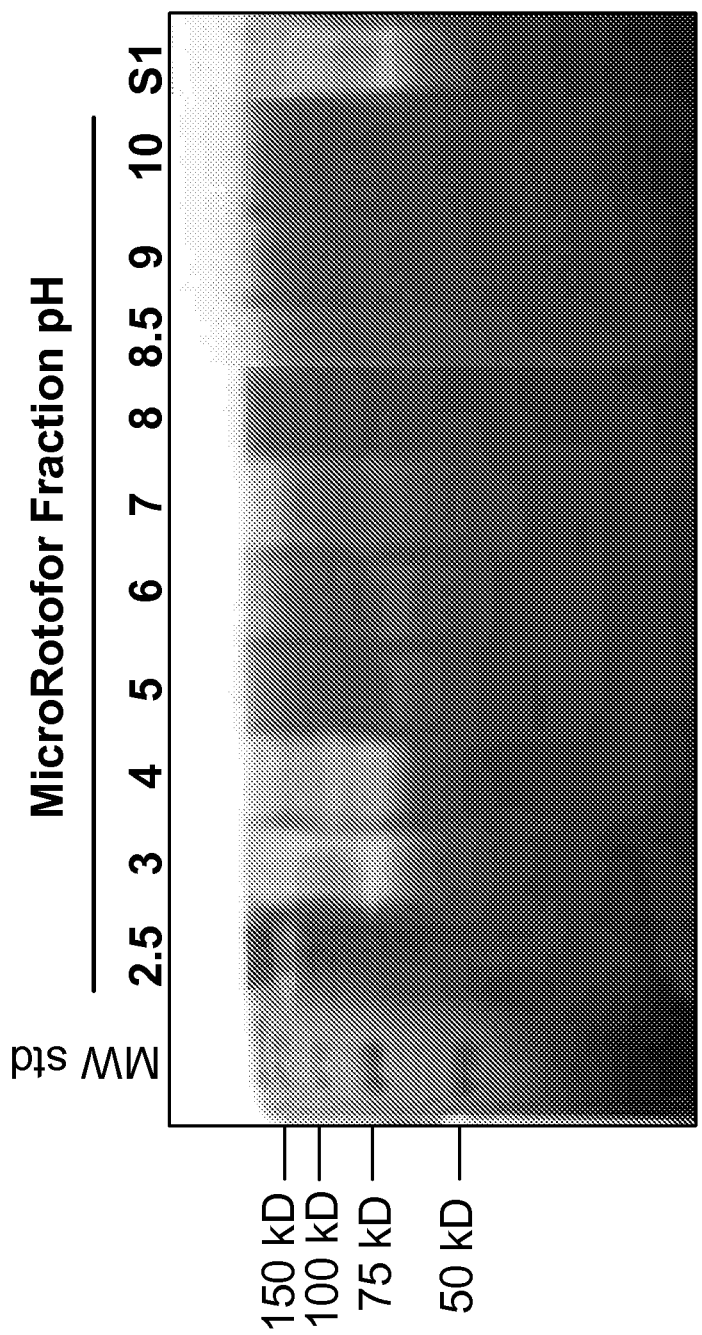
FIG. 6. Isoelectric focusing profile of the gliadin degrading enzymes. Proteins in sonicated plaque bacteria supernatant were separated based on isoelectric point by liquid iso-electric focusing (IEF). The enzymatic activity in each of the 10 IEF fractions was established by gliadin zymography. Far left lane, MW standard; S1: plaque supernatant sample before IEF.

In one embodiment, the enzyme described herein retains protease activity at pH 2.5 and has an approximate molecular size of 140 kDa as determined by a gliadin zymogram or characterized as in FIG. 6. In another embodiment, the enzyme described herein retains protease activity at pH 2.5 and has an approximate molecular size range of 120-150 kDa as determined by gliadin zymography. In another embodiment, the enzyme described herein retains protease activity at pH 2.5 and has an approximate molecular size range of 135-145 kDa as determined by gliadin zymography.

In one embodiment, the enzyme described herein retains protease activity in the range between pH 3.0-4.0 and has an approximate molecular size of 140 kDa as determined by a gliadin zymogram or characterized as in FIG. 6. In another embodiment, the enzyme described herein retains protease activity in the range between pH 3.0-4.0 and has an approximate molecular size range of 120-150 kDa as determined by gliadin zymography. In another embodiment, the enzyme described herein retains protease activity in the range between pH 3.0-4.0 and has an approximate molecular size range of 135-145 kDa as determined by gliadin zymography. In another embodiment, the enzyme described herein retains protease activity in the range between pH 3.0-4.0 and has an approximate molecular size range of 50-90 kDa as determined by gliadin zymography. In another embodiment, the enzyme described herein retains protease activity in the range between pH 3.0-4.0 and has an approximate molecular size range of 65-75 kDa as determined by gliadin zymography.

In one embodiment, the enzyme described herein retains protease activity in the range between pH 5.0-7.0 and has an approximate molecular size of 140 kDa as determined by a gliadin zymogram or characterized as in FIG. 6. In another embodiment, the enzyme described herein retains protease activity in the range between pH 5.0-7.0 and has an approximate molecular size range of 120-150 kDa as determined by gliadin zymography. In another embodiment, the enzyme described herein retains protease activity in the range between pH 5.0-7.0 and has an approximate molecular size range of 135-145 kDa as determined by gliadin zymography. In another embodiment, the enzyme described herein retains protease activity in the range between pH 5.0-7.0 and has an approximate molecular size range of 50-90 kDa as determined by gliadin zymography. In another embodiment, the enzyme described herein retains protease activity in the range between pH 5.0-7.0 and has an approximate molecular size range of 65-75 kDa as determined by gliadin zymography.

In one embodiment, the enzyme described herein retains protease activity in the range between pH 2.5-5.0 and has an approximate molecular size of 140 kDa as determined by a gliadin zymogram or characterized as in FIG. 6. In another embodiment, the enzyme described herein retains protease activity in the range between pH 2.5-5.0 and has an approximate molecular size range of 120-150 kDa as determined by gliadin zymography. In another embodiment, the enzyme described herein retains protease activity in the range between pH 2.5-5.0 and has an approximate molecular size range of 135-145 kDa as determined by gliadin zymography. In another embodiment, the enzyme described herein retains protease activity in the range between pH 2.5-5.0 and has an approximate molecular size range of 50-90 kDa as determined by gliadin zymography. In another embodiment, the enzyme described herein retains protease activity in the range between pH 2.5-5.0 and has an approximate molecular size range of 65-75 kDa as determined by gliadin zymography.

In one embodiment, the enzyme described herein retains protease activity in the range between pH 2.5-7.0 and has an approximate molecular size of 140 kDa as determined by a gliadin zymogram or characterized as in FIG. 6. In another embodiment, the enzyme described herein retains protease activity in the range between pH 2.5-7.0 and has an approximate molecular size range of 120-150 kDa as determined by gliadin zymography. In another embodiment, the enzyme described herein retains protease activity in the range between pH 2.5-7.0 and has an approximate molecular size range of 135-145 kDa as determined by gliadin zymography. In another embodiment, the enzyme described herein retains protease activity in the range between pH 2.5-7.0 and has an approximate molecular size range of 50-90 kDa as determined by gliadin zymography. In another embodiment, the enzyme described herein retains protease activity in the range between pH 2.5-7.0 and has an approximate molecular size range of 65-75 kDa as determined by gliadin zymography.

Pharmaceutical Formulations

A pharmaceutical formulation as described herein can be an isolated enzyme, a plurality of isolated enzymes in an admixture, a pro-biotic formulation of *Rothia* species bacteria (e.g., delivery of live or lyophilized bacteria), or an extract of *Rothia* species bacteria. The pharmaceutical formulation comprises an effective amount or effective does of the active enzyme or bacteria. In one embodiment, the effective dose of the extract from the *Rothia* species bacterium is administered orally. In other embodiments, the effective dose of the *Rothia* species bacteria or the glutamine endopeptidase enzyme derived or isolated from a *Rothia* species bacterium is administered orally.

In one embodiment, the isolated enzyme, a plurality of isolated enzymes in an admixture, a pro-biotic formulation of *Rothia* species bacteria, or an extract from the *Rothia* species bacteria is admixed to the gluten-containing foodstuff. In other embodiments, the *Rothia* species bacteria or the glutamine endopeptidase enzyme derived or isolated from a *Rothia* species bacterium is contacted with (e.g., admixed to) the gluten-containing foodstuff. For example, the extract, the bacteria or enzyme is mixed with the gluten-containing foodstuff prior to ingesting.

In one embodiment, the isolated enzyme, a plurality of isolated enzymes in an admixture, a pro-biotic formulation of *Rothia* species bacteria, or the extract from the *Rothia* species bacteria is formulated with a pharmaceutically acceptable excipient or carrier. In other embodiments, the *Rothia* species bacteria or the glutamine endopeptidase enzyme derived or isolated from a *Rothia* species bacterium is formulated with a pharmaceutically acceptable excipient or carrier.

In one embodiment, the isolated enzyme, a plurality of isolated enzymes in an admixture, a pro-biotic formulation of *Rothia* species bacteria, or the extract from the *Rothia* species bacteria is contained in a formulation that comprises an enteric coating. In other embodiments, the *Rothia* species bacteria or the glutamine endopeptidase enzyme derived or isolated from a *Rothia* species bacteria is contained in a formulation that comprises an enteric coating.

In one embodiment, the isolated enzyme, a plurality of isolated enzymes in an admixture, a pro-biotic formulation of *Rothia* species bacteria, or the extract from the *Rothia* species bacteria is a lyophilized preparation. In other embodiments, the *Rothia* species bacteria or the glutamine endopeptidase enzyme derived or isolated from a *Rothia* species bacterium is a lyophilized preparation. Lyophilization or freeze-drying is a means of drying achieved by freezing a wet substance and causing the ice to sublime directly to vapor by exposing it to a low partial pressure of water vapor. In practice, the substance may not be completely frozen, especially if non-aqueous solutions are present, and most lyophilization processes are completed by a period of desorption drying. The purpose of freeze-drying is to increase the shelf life, or preserve a specimen, be it food, microbial organisms, or, in some circumstances to decrease the size of the product. For various purposes, such as stable storage, the extract, bacteria or isolated enzyme can be lyophilized. Lyophilization is preferably performed on an initially concentrated preparation, e.g. of at least about 1 mg/ml for extract or isolated enzyme preparation and 1000 bacteria/ml. PEG can be added to improve enzyme stability, if so desired. In some embodiments, lyophilization of an extract, bacteria or isolated enzyme can be performed without loss of specific activity (e.g., gluten-degrading activity). Lyophilized extracts are useful in the production of enteric-coated capsules, enteric-coated tablets, capsules, or tablets.

In one embodiment of the methods described herein further comprises administering an effective dose of prolyl endopeptidase ranging from 0.01 mg to 500 mg/kg body weight. The prolyl endopeptidase can be provided in a separate formulation or can be formulated with the active species (e.g., extract, isolated enzyme etc) described herein. Prolyl endopeptidase (PREP or PEP) or prolyl oligopeptidase (EC 3.4.21.26), (sometimes also known as post-proline cleaving enzyme) is a large cytosolic enzyme that belongs to a distinct class of serine peptidases. The enzyme cleaves peptide bonds at the C-terminal side of proline residues. Its activity is confined to action on oligopeptides of less than 10 kDa and it has an absolute requirement for the trans-configuration of the peptide bond preceding proline. Some types of prolyl endopeptidase have been used in studies to decrease the propensity of gluten-containing wheat products to aggravate celiac disease (Stepniak D, et al., 2006, Am J Physiol Gastrointest Liver Physiol 291 (4): G621-9), e. g. PEP derived or isolated from *Flavobacterium meningosepticum, Sphingomonas capsulate, Penicillium citrinum, Lactobacillus helveticus* and *Myxococcus Xanthus* in US Patent Application 20060002917 and 20080193436, and in U.S. Pat. Nos. 7,563,864, 7,303,871, and 7,320,788.

In some embodiments of the pharmaceutical formulations described herein, the glutamine endopeptidase enzyme(s) in the 70 kDa region of a gliadin zymogram, is/are active in a saliva sample, is/are metal-ion dependent serine protease, is/are stable to acid conditions, and detoxifies gluten by cleaving the peptide bond after glutamine at -XPQ- motifs in gluten-containing foodstuff, wherein X=any amino acids, P=proline, and Q=glutamine. In one embodiment, glutamine endopeptidase enzyme is active in a buffer that mimics the ion composition of saliva, e. g. saliva ion buffer described herein.

In one embodiment of the pharmaceutical formulations described herein, the *Rothia* species bacteria is *Rothia* species ot 188 (strain WSA-8), also known as *Rothia* sp. HOT-188 and *Rothia aeria*.

In some embodiments of the pharmaceutical formulations described herein, the effective dose of the extract ranges from 0.01 mg to 500 mg/kg body weight when the formulation comprises the extract and/or isolated glutamine endopeptidase enzyme, and 1000 to 30 billion bacteria when the formulation comprises the *Rothia* species bacteria.

In some embodiments of the pharmaceutical formulations described herein, the formulation is suitable for oral administration, e. g. a tablet or a capsule.

In some embodiments of the pharmaceutical formulations described herein, the formulation comprises an enteric coating.

In one embodiment, the extract, *Rothia* species bacteria, or isolated enzyme described herein are formulated into pharmaceutical compositions by combination with appropriate, pharmaceutically acceptable carriers or diluents, and are formulated into preparations in solid, semi-solid, or liquid forms, such as tablets, capsules, powders, granules, solutions, gels, and microspheres. As such, administration of the extract, *Rothia* species bacteria, or the enzyme described herein can be achieved by oral administration.

In pharmaceutical dosage forms, the extract, *Rothia* species bacteria, or enzyme described herein can be administered alone or in appropriate association, as well as in combination, with other pharmaceutically active compounds. For example, the methods and compositions provided herein can be combined with pharmaceutically active compounds used in the treatment and alleviation of symptoms of Celiac Sprue including, but not limited to, the following: an inhibitor of tissue transglutaminase (see U.S. Pat. No. 7,579,313), an anti-inflammatory agent, an anti-ulcer agent, a mast cell-stabilizing agent, and/or and anti-allergy agent. Examples of such agents include HMG-CoA reductase inhibitors with anti-inflammatory properties such as compactin, lovastatin, simvastatin, pravastatin and atorvastatin; anti-allergic histamine H1 receptor antagonists such as acrivastine, cetirizine, desloratadine, ebastine, fexofenadine, levocetirizine, loratadine and mizolastine; leukotriene receptor antagonists such as montelukast and zafirlukast; COX2 inhibitors such as celecoxib and rofecoxib; p38 MAP kinase inhibitors such as BIRB-796; and mast cell stabilizing agents such as sodium chromoglycate (chromolyn), pemirolast, proxicromil, repirinast, doxantrazole, amlexanox nedocromil and probicromil.

In one embodiment, the formulation or administration protocol combines an extract, *Rothia* species bacteria, and/or glutamine endopeptidase enzyme described herein with an inhibitor of transglutaminase 2 (TG2) (see U.S. Pat. No. 7,579,313). Such formulations can provide additional protection from gluten mediated enteropathy, as TG2 has been shown to have a significant pro-inflammatory effect on gluten peptides in the celiac gut. In particular, TG2 inhibitors containing halo-dihydroisoxazole, diazomethylketone or dioxoindole moieties are useful for this purpose.

In one embodiment, the formulation or administration protocol combines an extract, *Rothia* species bacteria, and/or glutamine endopeptidase enzyme described herein with an anti-inflammatory agent, e.g. a statin; p38 MAP kinase inhibitor; anti-TNFalpha agent; etc.

In one embodiment, the formulation comprises an extract from a *Rothia* species bacteria, the glutamine endopeptidase enzyme described herein or a PEGylated form thereof. PEGylation is the process of covalent attachment of poly (ethylene glycol) polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance. PEGylation can also provide water solubility to hydrophobic drugs and proteins.

Methods of PEGylating proteins are known to one of ordinary skill in the art, e. g. U.S. Pat. No. 7,585,837 and also described herein. The first step of the PEGylation is the suitable functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates and carbonates. In the second generation PEGylation chemistry more efficient functional groups such as aldehyde, esters, amides etc made available for conjugation. Preferred end groups for heterobifunctional PEGs are maleimide, vinyl sulfones, pyridyl disulfide, amine, carboxylic acids and NHS esters.

Pharmaceutical formulations can be formulated for administration by any known route. By way of example, the composition can be administered by a mucosal, pulmonary, topical, or other localized or systemic route (e.g., enteral and parenteral). The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection, infusion and other injection or infusion techniques, without limitation. It is preferred herein that the formulations described herein are administered orally (or mixed with gluten-containing foodstuff) to a subject afflicted with celiac disease or a related disorder.

For oral preparations, the extract, *Rothia* species bacteria, or enzyme described herein can be used alone or in combination with appropriate additives to make tablets, powders, granules or capsules, for example, with conventional additives, such as lactose, mannitol, corn starch or potato starch; with binders, such as microcrystalline cellulose, cellulose derivatives, acacia, corn starch or gelatins; with disintegrants, such as corn starch, potato starch or croscarmellose sodium; with lubricants, such as talc or magnesium stearate; and if desired, with diluents, buffering agents, moistening agents, preservatives, colorants, and flavoring agents.

For enteral administration, a composition can be incorporated into an inert carrier in discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught. Suitable carriers may be starches or sugars and include lubricants, flavorings, binders, and other materials of the same nature.

A tablet can be made by compression or molding, optionally with one or more accessory ingredients. Compressed tablets can be prepared by compressing in a suitable machine the active compound in a free-flowing form, e.g., a powder or granules, optionally mixed with accessory ingredients, e.g., binders, lubricants, inert diluents, surface active or dispersing agents. Molded tablets can be made by molding in a suitable machine, a mixture of the powdered active compound with any suitable carrier.

A syrup or suspension can be made by adding the extract, *Rothia* species bacteria, or isolated enzyme described herein to a concentrated, aqueous solution of a sugar, e.g., sucrose, to which can also be added any accessory ingredients. Such accessory ingredients may include flavoring, an agent to retard crystallization of the sugar or an agent to increase the solubility of any other ingredient, e.g., as a polyhydric alcohol, for example, glycerol or sorbitol.

Formulations for oral administration can be presented with an enhancer. Orally-acceptable absorption enhancers include surfactants such as sodium lauryl sulfate, palmitoyl carnitine, Laureth-9, phosphatidylcholine, cyclodextrin and derivatives thereof; bile salts such as sodium deoxycholate, sodium taurocholate, sodium glycochlate, and sodium fusidate; chelating agents including citric acid and salicylates; and fatty acids (e.g., oleic acid, lauric acid, acylcarnitines, mono- and diglycerides). Other oral absorption enhancers include benzalkonium chloride, benzethonium chloride, CHAPS (3-(3-cholamidopropyl)-dimethylammonio-1-propanesulfonate), Big-CHAPS (N,N-bis(3-D-gluconamidopropyl)-cholamide), chlorobutanol, octoxynol-9, benzyl alcohol, phenols, cresols, and alkyl alcohols. An especially preferred oral absorption enhancer for the present invention is sodium lauryl sulfate.

While not required, in one embodiment, the formulations comprising an extract, a *Rothia* species bacteria, or an enzyme described herein and the oral formulations comprise enteric coatings, so that the extract, *Rothia* species bacteria, or enzyme described herein is delivered to the intestinal tract. Enteric formulations are often used to protect an active ingredient from the strongly acid contents of the stomach. Such formulations are created by coating a solid dosage form with a film of a polymer that is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate, methacrylate copolymers, and cellulose acetate phthalate.

An extract, a *Rothia* species bacteria, or an isolated enzyme described herein, can be prepared as a tablet formulation comprising the extract, the *Rothia* species bacteria, or the enzyme described herein with an enteric polymer casing. An example of such a preparation can be found in WO2005/021002. The active material in the core can be present in a micronized or solubilized form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof; binders such as microcrystalline cellulose, hydroxypropyl-methylcellulose, hydroxypropyl-cellulose, polyvinylpyrrolidone, pre-gelatinised starch or gum acacia or mixtures thereof; disintegrants such as microcrystalline cellulose (fulfilling both binder and disintegrant functions) cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilisers such as desiccating amorphous silica, coloring agents, flavors etc. Preferably the tablet comprises lactose as diluent. When a binder is present, it is preferably hydroxypropylmethyl cellulose. Preferably, the tablet comprises magnesium stearate as lubricant. Preferably the tablet comprises croscarmellose sodium as disintegrant. Preferably, the tablet comprises microcrystalline cellulose.

The diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

The extract, the *Rothia* species bacteria, or the enzyme described herein preferably comprises between 10 and 50% of the weight of the core, more preferably between 15 and 35% of the weight of the core (calculated as free base equivalent). The core can contain any therapeutically suitable dosage level of the active ingredient, but preferably contains up to 150 mg as free base of the active ingredient. The core can contain 20, 30, 40, 50, 60, 80 or 100 mg as free base of the active ingredient. The active ingredient can be present as the free base, or as any pharmaceutically acceptable salt. If the active ingredient is present as a salt, the weight is adjusted such that the tablet contains the desired amount of active ingredient, calculated as free base of the salt. Preferably, the active ingredient is present as a hydrochloride salt.

The core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

The core is surrounded by a casing which comprises an enteric polymer. Examples of enteric polymers are cellulose acetate phthalate, cellulose acetate succinate, methylcellulose phthalate, ethylhydroxycellulose phthalate, polyvinylacetate pthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional cross-linking agents such as epichlorohydrin, dichlorohydrin or 1,2-, 3,4-diepoxybutane. The casing can also include starch and/or dextrin.

Exemplary enteric coating materials are the commercially available EUDRAGIT® enteric polymers such as EUDRAGIT® L, EUDRAGIT® S and EUDRAGIT® NE used alone or with a plasticiser. Such coatings are normally applied using a liquid medium, and the nature of the plasticiser depends upon whether the medium is aqueous or non-aqueous. Plasticizers for use with aqueous medium include propylene glycol, triethyl citrate, acetyl triethyl citrate or CITROFLEX® or CITROFLEX® A2. Non-aqueous plasticizers include these, and also diethyl and dibutyl phthalate and dibutyl sebacate. A preferred plasticiser is triethyl citrate. The quantity of plasticiser included will be apparent to those skilled in the art.

The casing can also include an anti-tack agent such as talc, silica or glyceryl monostearate. Preferably the anti-tack agent is glyceryl monostearate. Typically, the casing can include around 5-25 wt % Plasticiser and up to around 50 wt % of anti tack agent, preferably 1-10 wt % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%

In one embodiment, there is a seal coat included between the core and the enteric coating. A seal coat is a coating material which can be used to protect the enteric casing from possible chemical attack by any alkaline ingredients in the core. The seal coat can also provide a smoother surface, thereby allowing easier attachment of the enteric casing. A person skilled in the art would be aware of suitable coatings. Preferably the seal coat is made of an Opadry coating, and particularly preferably it is Opadry White OY-S-28876.

In an example, lactose monohydrate, microcrystalline cellulose, the active ingredient—e.g. the extract form *Rothia* species, the hydroxypropyl methyl cellulose and half of the croscarmellose sodium are screened into a 10 Liter Fielder high-shear blender (any suitable high shear blender could be used) and blended for 5 minutes at 300 rpm with the chopper off. The mixture is then granulated by the addition of about 750 ml water whilst continuing to blend. The granules are dried in a Glatt 3/5 fluid bed drier, screened by Comil into a Pharmatec 5 Liter bin blender and then blended with any lactose anhydrous given in the formula plus the remainder of the croscarmellose sodium over 5 minutes at 20 rpm. Magnesium stearate is screened into the blender and the mixing process continued for a further 1 minute at 10 rpm. The lubricated mix is compressed using a Riva Piccolla rotary tablet press fitted with 9.5 mm round normal convex punches (any suitable tablet press could be used). The sealcoat, and subsequently the enteric coat, are applied by spraying of an aqueous suspension of the coat ingredients in a Manesty 10 coater using parameters for the coating process as recommended by the manufacturers of the coating polymers (again, any suitable coater could be used).

Other enteric formulations comprise engineered polymer microspheres made of biologically erodable polymers, which display strong adhesive interactions with gastrointestinal mucus and cellular linings and can traverse both the mucosal absorptive epithelium and the follicle-associated epithelium covering the lymphoid tissue of Peyer's patches. The polymers maintain contact with intestinal epithelium for extended periods of time and actually penetrate it, through and between cells. See, for example, Mathiowitz et al. (1997) Nature 386 (6623): 410-414. Drug delivery systems can also utilize a core of superporous hydrogels (SPH) and SPH composite (SPHC), as described by Dorkoosh et al. (2001) J Control Release 71 (3):307-18. Other enteric-coated preparations of this sort can be prepared by one skilled in the art, using these materials or their equivalents.

The compositions can be formulated as a sustained release composition. For example, sustained-release means or delivery devices are known in the art and include, but are not limited to, sustained-release matrices such as biodegradable matrices or semi-permeable polymer matrices in the form of shaped articles, e.g., films, or microcapsules that comprise the extract, *Rothia* species bacteria, or enzyme described herein A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of polylactide, polyglycolide, or polylactide co-glycolide (co-polymers of lactic acid and glycolic acid).

Sustained-release matrices include polylactides (U.S. Pat. No. 3,773,919, EP 58,481), copolymers of L-glutamic acid and gamma-ethyl-L-glutamate (U. Sidman et al., Biopolymers 22:547-556 (1983)), poly(2-hydroxyethyl methacrylate) (R. Langer et al., J. Biomed Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained-release compositions also include liposomally entrapped extract, *Rothia* species bacteria, or enzyme described herein. Such liposomes can be prepared by methods known per se: DE 3,218,121; Epstein, et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy. Other biodegradable polymers and their use are described, for example, in detail in Brem et al. (1991, J. Neurosurg. 74:441-446). For examples of sustained release compositions, see U.S. Pat. No. 3,773,919, EP 58,481A, U.S. Pat. No. 3,887,699, EP 158,277A, Canadian Patent No. 1176565, U. Sidman et al., Biopolymers 22:547 (1983) and R. Langer et al., Chem. Tech. 12:98 (1982).

Methods for preparing liposomes and microspheres for administration to a patient are known to those of skill in the art. U.S. Pat. No. 4,789,734, the contents of which are hereby incorporated by reference, describes methods for encapsulating biological materials in liposomes. A review of known methods is provided by G. Gregoriadis, Chapter 14, "Liposomes," Drug Carriers in Biology and Medicine, pp. 287-341 (Academic Press, 1979).

Microspheres formed of polymers or proteins are well known to those skilled in the art, and can be tailored for passage through the gastrointestinal tract directly into the blood stream. Alternatively, the compound can be incorporated and the microspheres or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

Preferred micro particles are those prepared from biodegradable polymers, such as polyglycolide, polylactide and copolymers thereof. Those of skill in the art can readily determine an appropriate carrier system depending on various factors, including the desired rate of drug release and the desired dosage.

The pharmaceutically acceptable excipients, such as vehicles, adjuvants, carriers or diluents that are inherently nontoxic and nontherapeutic, are commercially available. Moreover, pharmaceutically acceptable auxiliary substances, such as pH adjusting and buffering agents, tonicity adjusting agents, stabilizers, wetting agents and the like, are commercially available. Any compound useful in the methods and compositions of the invention can be provided as a pharmaceutically acceptable base addition salt. "Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2 dimethylaminoethanol, 2 diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N ethylpiperidine, polyamine resins and the like. Particularly preferred organic bases are isopropylamine, diethylamine, ethanolamine, trimethylamine, dicyclohexylamine, choline and caffeine.

Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol.

In one embodiment, other ingredients may be added to pharmaceutical formulations, including antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA, and sugar alcohols such as mannitol or sorbitol.

In one embodiment, the pharmaceutical formulation to be used for therapeutic administration must be sterile. Sterility is readily accomplished by filtration through sterile filtration membranes (e.g., 0.2 micron membranes).

Dosage and Administration

Depending on the subject, severity of disease and condition being treated and on the administration route, an extract, Rothia species bacteria, or isolated enzyme described herein can be administered in dosages of 0.01 mg to 500 mg/kg body weight per day, e.g. about 20, 100, 250, 500 or more mg/day or about 0.5, 1, 1.5, or more g/day for an average person for the extract or the enzyme and 1000 to 30 billion bacteria per dose per day for the Rothia species bacteria. A typical dose of the extract or enzyme described herein in subjects will be at least about 1 mg/adult subject, at least about 10 mg/adult subject; or at least about 50, 150, 250, 500 or more mg/adult subject. In some embodiments, the dosage is no more than about 5 g, no more than about 1 g, or no more than about 500 mg/adult subject. Efficient proteolysis of gluten in vivo for an adult can, depending on diet and other factors, require at least about 500 units of a therapeutically efficacious glutamine endopeptidase from Rothia species bacteria described herein. In some embodiments, low dose of glutamine endopeptidase, such as 1000 units, can be used. In other embodiments, such as for the rapid detoxification of 5-10 g ingested gluten, as much as 20,000-50,000 units can be provided in unit dose form. One unit is defined as the amount of enzyme required to hydrolyze 1 µmol of Z-KPQ-pNA or Z-YPQ-pNA per min under specified conditions. Most PEPs have specific activities in the range of 5-50 units/mg protein. For barley EP-B2 (whose specific activity is in the 1000 Units/mg range, as measured with Cbz-Phe-Arg-pNA), low dose glutenase may consist of 10,000-100,000 Units, whereas high-dose PEPs contains as much as 1,000,000 Units. It will be understood by those of skill in the art that the dose can be raised, but that additional benefits may not be obtained by exceeding the useful dosage. Dosages will be appropriately adjusted for pediatric formulation. In children the effective dose may be lower, for example at least about 0.1, 0.5, 1, 10, 20, 100, 150, 250 or more mg.

In one embodiment, the compositions or formulations are admixed with gluten-containing foodstuff in vitro for the purpose of detoxifying the gluten-containing foodstuff, i.e., reducing the production of toxic gluten oligopeptides when ingested and further digested by a subject. The effective dosage for in vitro detoxification will depend on many factors, e.g., the degree of detoxification desired (partial or complete), the state of the gluten-containing foodstuff, the time and pH of digestion and the ratio of composition or formulation to the amount of gluten-containing foodstuff to be digested. A typical dose for the enzyme can be 10 units per 1 g for a 24 hour complete digestion. One skilled in the art will be able to vary the units in proportion to the amount of gluten-containing foodstuff and the time allowed for digestion to attained the desired level of digestion.

The skilled artisan will appreciate that certain factors may influence the dosage and timing required to effectively treat a subject, including but not limited to the severity of the disease or disorder, previous treatments, the general health and/or age of the subject, and other diseases present. The dose levels can also depend on whether the extract, Rothia species bacteria, or enzyme is used, the severity of the symptoms and the susceptibility of the subject to side effects. The isolated enzyme can be more potent than the extract or the bacteria. Moreover, treatment of a subject with a therapeutically effective dose can include a single treatment or a series of treatments. Estimates of effective dosages and in vivo half-lives for the extract, Rothia species bacteria, or enzyme encompassed by the invention can be made using conventional methodologies or on the basis of in vivo testing using an appropriate animal model, as known in the art, or as described herein. Preferred dosages for a given enzyme are readily determinable by those of skill in the art by a variety of means.

The therapeutic effect can be measured in terms of clinical outcome or can be determined by immunological or biochemical tests. For example, in the treatment of Celiac sprue, suppression of the deleterious T-cell activity can be measured by enumeration of reactive Th1 cells, by quantitating the release of cytokines at the sites of lesions, or using other assays for the presence of autoimmune T cells known in the art. Alternatively, one can look for a reduction in symptoms of celiac disease as described herein or, e.g. as set forth in Pyle et al, Clin. Gastroenterol. Hepatol. 3:679-686, 2005.

Various methods for administration may be employed, it being appreciated that the formulations of the extract, Rothia species bacteria, or enzyme described herein provided by the present invention provide improved formulations for oral administration. For example, in the treatment of Celiac Sprue with an extract, *Rothia* species bacteria, or enzyme described herein, the present invention provides unit dose forms of the extract, *Rothia* species bacteria, or enzyme described herein suitable for administration with meals. The dosage of the therapeutic formulation will vary widely, depending upon the nature of the disease, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, with meals, semi-weekly, or otherwise as needed to maintain an effective dosage level.

Lyophilized formulations of an extract, bacteria or isolated enzyme and excipients is useful in the production of enteric-coated capsules or tablets, e.g. a single capsule or tablet can contain at least about 1 mg usually at least about 10 mg of *Rothia* species bacterial extract or isolated glutamine endopeptidase enzyme, and may contain at least 100 mg glutamine endopeptidase, at least about 200 mg, at least about 300 mg, at least about 400 mg, at least about 500 mg, up to about 1000 mg protein, including all the numbers between 1-1000 mg. Wherein lyophilized bacteria comprises the enteric-coated capsules or tablets, a single capsule or tablet can contain at least about 1000, at least about 10,000, at least about 100,000, at least about 1 billion *Rothia* species bacteria, up to 30 billion including all the numbers between 1-30 billion. As described in detail here, enteric coatings can be applied, where a substantial fraction of the activity is retained, and is stable for at least about 1 month at 4° C. The method of lyophilizing bacteria is known to one skilled in the art, e. g. U.S. Pat. Nos. 4,205,132, 4,444,760, RE40023, 5,192,743, 5,529,915, 6,750,330, and 7,572,893, all of which are incorporated by reference inn their entirety.

In one embodiment, the effective dose of the extract from the *Rothia* species bacteria from ranges 0.01 mg to 500 mg/kg body weight. In another embodiment, wherein the *Rothia* species bacteria are used, the effective dose of the *Rothia* species bacteria ranges from 1000 to 30 billion *Rothia* species bacteria. In another embodiment, wherein the glutamine endopeptidase enzyme derived or isolated from a *Rothia* species bacterium is used, the effective dose of the enzyme is from 0.01 mg to 500 mg/kg body weight. In one embodiment, the *Rothia* species bacteria is delivered as a pro-biotic formulation (e.g., live microorganisms or admixed with gluten-containing food-stuff).

In one embodiment, the method is practiced when the subject is consuming any gluten-containing foodstuff. In another embodiment, the method is practiced prior to the consumption of gluten-containing foodstuff, wherein the subject is preparing to ingest gluten-containing food or the subject suspects that there might be gluten or wheat-derived ingredients in the food that the subject is about to consume. In another embodiment, the method is practiced whenever food is consumed or e.g., three times a day with the three major meals of a day: breakfast, lunch and dinner.

Accordingly, in some embodiments, the extract from *Rothia* species bacteria is administered just before, during, or just after consumption of gluten-containing foodstuff.

In one embodiment, the extract from *Rothia* species bacteria is administered prior to consumption of gluten-containing foodstuff. In one embodiment, the extract from *Rothia* species bacteria is administered in a gluten-containing foodstuff. In one embodiment, the extract from *Rothia* species bacteria is administered from 1 hour prior to 1 hour after the subject has consumed a gluten-containing foodstuff.

In one embodiment, the extract from *Rothia* species bacteria is administered just before, during, or just after consumption of gluten-containing foodstuff.

In one embodiment, the pharmaceutical formulation as described herein is administered in an amount sufficient to attenuate gluten toxicity, as that term is used herein.

Formulations are typically provided in a unit dosage form, where the term "unit dosage form," refers to physically discrete units suitable as unitary dosages for the subjects, each unit containing a predetermined quantity of the extract, *Rothia* species bacteria, or enzyme described herein in an amount sufficient to produce the desired effect in association with a pharmaceutically acceptable diluent, carrier or vehicle. The specifications for the unit dosage forms of the present invention depend on the particular complex employed and the effect to be achieved, and the pharmacodynamics associated with each complex in the host.

Attenuates Gluten Toxicity

In the context of an enzyme or enzyme preparation, "attenuates gluten toxicity" refers to the action of an endopeptidase enzyme to reduce the amount, level or density of toxic gluten oligopeptides produced from gluten-containing foodstuff in the gut. Some toxic gluten oligopeptides are produced during digestion of gluten-containing foodstuff by endogenous trypsin, chymotrypsin, elastase and carboxypeptidase in the gastrointestinal tract. Attenuation of gluten toxicity is achieved by digesting toxic gluten oligopeptides to smaller peptide fragments that lack T cell epitopes in glutens recognized by the subject's immune system. The activity of a glutamine endopeptidase from *Rothia* species described herein, before and/or after the digestion of gluten oligopeptides produced by endogenous trypsin, chymotrypsin, elastase and carboxypeptidase would result in less than 10% of the post-digestion products being longer than PQPQLPYPQ (SEQ. ID. NO: 6) which has nine amino acid residues. This can be assessed by the longer retention times on a C18 reverse phase HPLC column monitored at A215 and such methods are well known to one skilled in the art.

In one embodiment, the attenuation of gluten toxicity occurs in vitro prior to the ingestion of the gluten-containing foodstuff. For example, the compositions or the formulation described herein is admixed to the gluten-containing foodstuff during the manufacture of the foodstuff.

The assessment of attenuation of gluten toxicity can be determined using a cell-based or in vitro assay by measuring the ability of the extract of *Rothia* species or isolated glutamine endopeptidase from *Rothia* species described herein to increase the concentration of free $NH_2$-termini in a reaction mixture containing e.g., 1 mg/ml of undigested or trypsin/chymotrypsin/elastase/carboxypeptidase pre-digested gluten substrate, and 10 μg/ml of the extract or isolated glutamine endopeptidase from a *Rothia* species, which can be incubated at 37° C. for 1 hour. Thus, attenuation of gluten toxicity in this context refers to an increase the concentration of free amino termini under such conditions by at least 25%, at least 30%, at least 40%, at least 50%, at least 60%, at least 70%, at least 80%, at least 90%, at least 95%, at least 99% or even 100% (no gluten toxicity). Additionally, a reduction in the residual molar concentration of oligopeptides greater than about e.g., 1000 Da can be measured using e.g., 1 mg/ml trypsin/chymotrypsin/elastase/carboxypeptidase pre-digested gluten substrate after a 1 hour incubation with 10 μg/ml of the extract or enzyme, which detects an increase in degradation of gluten toxic intermediates. This reduction in molar concentration is at least 50%, at least 1-fold, at least 2-fold, at least 5-fold, at least 10-fold, at least 100-fold, at least 1000-fold or more. The concentration of such oligopeptides can be estimated by methods known in the art, for example size exclusion chromatography and the like.

Alternatively, an in vitro based assay measuring the degradation of highly immunogenic peptides can be used; such highly immunogenic peptides can include those derived from α-gliadin (LQLQP-FPQPQLPYPQPQLPYPQPQLPYPQPQPF, (SEQ. ID. NO: 1; 33-mer) or γ-gliadin (FLQPQQP-FPQQPQQPYPQQPQQPFPQ, (SEQ. ID. NO: 2); 26-mer). For example, gliadin peptides (10 mg/mL) are contacted with an enzyme sample (e.g., extract, isolated enzyme, whole saliva) to be tested and incubated at various time points (e.g., 10 min, 30 min, 1 h, 2 h, 6 h, 12 h, 24 h, etc). The assay is stopped by heat inactivation (e.g., boiling) and the peptide sample is subjected to RP-HPLC to determine the presence, absence or degree of degradation.

In one embodiment, "attenuates gluten toxicity" also refers to reducing the ability of a gluten oligopeptide to bind to HLA-DQ (e.g., a decreased number of epitopes for recognition by a subject's immune system). The ability of a substrate to bind to HLA-DQ is indicative of its toxicity; fragments smaller than about 8 amino acids are generally not stably bound to Class II MHC. The detoxification of whole gluten can be monitored by polyclonal T cell lines derived from intestinal biopsies of celiac or gluten allergic patients, by LC-MS-MS and by ELISA assays using monoclonal antibodies capable of recognizing sequences specific to gliadin. For example, an extract of a *Rothia* species or an isolated glutamine endopeptidase from *Rothia* species described herein can reduce the potency by which a trypsin/chymotrypsin/elastase/carboxypeptidase pre-digested gluten substrate can antagonize binding of PQPELPYPQPQLP (SEQ. ID. NO: 165) to HLA-DQ2. Treatment with an isolated enzyme or extract of *Rothia* species bacteria or *Rothia* bacteria described herein permits digestion of toxic oligopeptides, thereby preventing the toxic oligopeptides from competing with a test peptide for MHC binding. Such a competition assay can be performed by incubating 1 mg/ml trypsin/chymotrypsin/elastase/carboxypeptidase pre-digested gluten substrate with 10 μg/ml of the extract or enzyme, and the ability of the resulting solution to displace radioactive PQPELPYPQPQLP (SEQ. ID. NO: 165) pre-bound to HLA-DQ2 molecules can then be quantified, with a reduction of displacement, relative to a non-treated control, indicative of utility in the methods of the present invention.

In one embodiment, "attenuates gluten toxicity" also refers to reducing the anti-tTG antibody and/or anti-gliadin antibodies response to a "gluten challenge diet" in a Celiac sprue or gluten allergic/gluten intolerance patient by at least 50%, at least 1-fold, at least 2-fold, at least 5-fold, at least 10-fold, at least 100-fold or more. A "gluten challenge diet" is defined as the intake of 100 g bread per day for 3 days by an adult Celiac sprue or gluten allergic patient previously on a gluten-free diet. The anti-tTG antibody (ATA) and anti-gliadin antibodies (AGA) response can be measured in peripheral blood using standard clinical diagnostic procedures, as known in the art.

The present invention can be defined in any of the following alphabetized paragraphs:

[A] An isolated enzyme composition comprising at least one gluten-degrading enzyme isolated from a *Rothia* species bacteria, wherein the at least one enzyme retains protease activity at an acidic pH of 3.0 as measured in an in vitro gliadin degradation assay for 3 hours using a synthetic substrate Z-YPQ-pNA, and wherein the at least one enzyme comprises an isoelectric point in a pH range of 2.0-7.0, inclusive.

[B] A probiotic composition comprising an effective amount of *Rothia* species bacteria comprising a gluten-degrading enzyme retains protease activity at acidic pH of 3.0 as measured in an in vitro gliadin degradation assay for 3 hours using a synthetic substrate Z-YPQ-pNA, and wherein the at least one enzyme and comprises an iso-electric point in a pH range of 2.0-7.0, inclusive, and a pharmaceutically acceptable carrier.

[C] A method for treating celiac disease or a related disorder, the method comprising administering to a subject an effective amount of at least one gluten-degrading enzyme isolated from a *Rothia* species bacteria, wherein the at least one enzyme retains protease activity at acidic pH of 3.0 as measured in an in vitro gliadin degradation assay for 3 hours using a synthetic substrate Z-YPQ-pNA, and wherein the at least one enzyme comprises an iso-electric point in a pH range of 2.0-7.0, inclusive, and attenuates gluten toxicity in the subject.

[D] A method for degrading gluten in a gluten-containing foodstuff prior to ingestion, the method comprises contacting the gluten-containing foodstuff with an effective amount of at least one gluten-degrading enzyme isolated from a *Rothia* species bacteria, wherein the at least one enzyme retains protease activity at acidic pH of 3.0 as measured in an in vitro gliadin degradation assay for 3 hours using a synthetic substrate Z-YPQ-pNA, and wherein the at least one enzyme comprises an iso-electric point in a pH range of 2.0-7.0, inclusive.

[E] The composition of paragraph [A] or [B], or the method of claim [C] or [D], wherein the *Rothia* species is *Rothia* species ot 188, also known as *Rothia* sp. HOT-188 and *Rothia aeria* (strain WSA-8).

[F] The composition or the method of paragraph [E], wherein the iso-electric point of the enzyme is in a pH range of 2.0-4.0, inclusive.

[G] The composition or the method of paragraph [F], wherein the at least one enzyme comprises a molecular weight between 120-150 kDa, inclusive.

[H] The composition or the method of paragraph G, wherein the at least one enzyme comprises a molecular weight of 135-145 kDa, inclusive.

[I] The composition or the method of paragraph H, wherein the at least one enzyme comprises a molecular weight between 50 and 90 kDa, inclusive.

[J] The composition or the method of paragraph I, wherein the at least one enzyme comprises a molecular weight between 65 and 75 kDa, inclusive.

[K] The composition or the method of any one of paragraphs A-I, wherein the pH in which the enzyme retains activity can vary between 2.5 and 5.0, inclusive.

[L] The composition or the method of paragraph K, wherein the pH is a pH of 2.5-3.0, inclusive.

[M] The composition or the method of any one of paragraphs A-L, wherein the at least one enzyme degrades a gliadin protein, a fragment thereof, or a gluten-containing foodstuff or ingredient thereof.

[N] The composition or method of paragraph M, wherein the degradation is partial.

[O] The composition or method of paragraph M, wherein the degradation is complete.

[P] The composition or method of paragraph M, wherein the fragment thereof is a 33-mer peptide of α2-gliadin or a 26-mer domain derived from γ-gliadin.

[Q] The composition or method of paragraph P, wherein the 33-mer peptide is (SEQ. ID. NO: 1)
LQLQPFPQPQLPYPQPQLPYPQPQLPYPQPQPF.

[R] The composition or method of paragraph P, wherein the 26-mer domain is (SEQ. ID. NO: 2)
FLQPQQPFPQQPQQPYPQQPQQPFPQ.

[S] The composition or method of paragraph M, wherein degradation occurs by cleaving the peptide bond after an amino acid sequence selected from the group consisting of -XPQ- -QQP-, -PPF-, -LYP- and/or -PFP-.

[T] The composition or method of paragraph S, wherein the amino acid sequence is -XPQ-.

[U] The composition of any one of paragraphs A, B, E-T, wherein the at least one gluten-degrading enzyme in admixed with a gluten-containing foodstuff.

[V] The composition of paragraph U, wherein the at least one gluten-degrading enzyme retains activity in the admixture.

[W] A method for treating celiac disease or a related disorder, the method comprising administering the composition of any one of paragraphs A, B, E-U.

[X] The method of any one of paragraphs C, D, E-T, and W, wherein the related disorder is selected from the group consisting of refractory celiac disease, gluten allergy, gluten intolerance and dermatitis herpetiformis.

This invention is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

EXAMPLES

Proteolytic degradation of protease-resistant domains in gluten appears to require enzymatic cleavage specificities that are not readily available in the repertoire of mammalian digestive enzymes. Recent studies have revealed that the oral cavity contains microorganisms producing endoprotease(s) with cleavage specificity after a glutamine residue (Helmerhorst E J, et al. *J Biol Chem* 2008; 283: 19957-66). The activity was found by analyzing the sequences of salivary peptides that are naturally present in human whole saliva. The salivary peptidome contains multiple peptides derived from human salivary basic proline-rich proteins that were cleaved after the Xaa-Pro-Gln tripeptide sequence (Helmerhorst E J, et al., *J Biol Chem* 2008; 283:19957-66; Vitorino R, et al. *Prot Clin Appl* 2009; 3: 528-540; Messana I, et al. *Mol Cell Proteomics* 2008; 7:911-26). The structural similarity between gliadins and basic proline-rich proteins was studied to investigate if gliadins are substrates for oral microbial proteases and can be degraded into non-immunogenic peptides. As described herein in the Examples section, natural gluten degrading microorganisms are associated with the oral cavity, i.e. the very proximal GI tract, and open new avenues to neutralize the deleterious effects of gluten in patients with celiac disease.

Example 1

Exemplary Materials and Methods

Dental Plaque and Whole Saliva Collection

Protocols for the collection of human dental plaque and whole saliva (WS) were approved by the Institutional Review Board at Boston University. Plaque was obtained from a healthy subject 48 h after cessation of oral hygiene. The sample was collected from interproximal spaces using a sterile dental scaler and suspended in saliva ion buffer containing 50 mM KCl, 1.5 mM potassium phosphate, 1 mM CaCl2 and 0.1 mM MgCl2, pH 7.0 14. The plaque material was dispersed by pipetting and vortexing and the density of the resulting suspension was determined spectrophotometrically at 620 nm. Stimulated WS (5 ml) was collected from eight healthy subjects between 10.00 and 11.00 a.m. at least 1 hour after the last meal. Whole saliva flow was stimulated by mastication using 1 g of paraffin wax (Parafilm, American National Can™, Chicago, Ill.). All samples were kept on ice.

Enzyme Activity Analysis

Four synthetic analogs, Z-YPQ-pNA, Z-QQP-pNA, Z-PPF-pNA, Z-LPY-pNA and Z-PFP-pNA, were chosen as representative gliadin-derived substrates and chemically synthesized (Anaspec, Fremont, Calif.). All substrates were dissolved in 50-75% dimethyl sulfoxide (DMSO) to 20 mM. From this solution, 2 µl was mixed with 200 µl plaque suspension (OD620 1.2) in saliva ion buffer or with 200 µl trypsin (final concentration 0.2 µg/ml) in 50 mM ammonium bicarbonate buffer, pH 8.0. All incubations were carried out in 96-well microtiter plates. Enzyme activity was determined from the proteolytic removal of the paranitroanilide group which was monitored spectrophotometrically at 405 nm. Z-YPQ-pNA, Z-PPF-pNA and Z-PFP-pNA showed mild precipitation upon mixing with the plaque suspension in saliva ion buffer which did not interfere with efficient substrate hydrolysis. All values were corrected for the lowest absorbance values measured after addition of the enzyme source to the substrate.

Degradation of Gliadin and Gliadin Peptides

A mixture of gliadins was purchased from Sigma (St. Louis, Mo.) and dissolved to 5 mg/ml in 60% (v/v) ethanol. Synthetic highly immunogenic peptides derived from α2-gliadin (LQLQPFPQPQLPYPQPQL-PYPQPQLPYPQPQPF (SEQ. ID. NO: 1); 33-mer) 17 or γ-gliadin (FLQPQQPFPQQPQQPYPQQPQQPFPQ (SEQ. ID. NO: 2); 26-mer) (Shan L, et al., *J Proteome Res* 2005; 4:1732-41) were synthesized at a purity of 95% (21 st Century Biochemicals, Marlboro, Mass.). Both peptides were dissolved in milliQ water at 10 mg/ml, and their concentration was verified by measurement of the OD215 applying a specific absorption coefficient $\epsilon$=20. Gliadin or gliadin peptides were added to a suspension of dental plaque bacteria in saliva ion buffer ($OD_{620}$ 1.2) or to whole saliva (WS) to final concentrations of 250 µg/ml. After various incubation time intervals, 100 µl aliquots were removed and boiled to inactivate enzyme activity. The 100 µl gliadin-containing sample aliquots were analyzed by SDS-PAGE whereas the 33-mer/26-mer-containing sample aliquots were subjected to RP-HPLC.

SDS PAGE Analysis

To the gliadin degradation sample aliquots, EDTA was added to a final concentration of 2.5 mM. Samples were dried using a speed-vac (Savant, Thermo Electron, Waltham, Mass.) and suspended in SDS sample buffer containing 0.4 mM EDTA, 2% (w/v) sodium dodecyl sulfate (SDS), 278 mM Tris/HCl (pH=8.5), 292 mM sucrose, 0.075% Serva Blue G250 (w/v) and 0.025% Phenol Red (w/v). Samples were loaded onto pre-cast 12% gels (NOVEX®, INVITROGEN™, Carlsbad, Calif.) in electrophoresis buffer containing 50 mM 2-(N-morpholino) ethane sulfonic acid (MES), 50 mM Tris base (pH=7.3), 0.1% (w/v) SDS. Electrophoresis was carried out at a constant voltage of 120 V. Gels were stained for 24 h with 0.1% Coomassie brilliant blue in 40% (v/v) methanol and 10% (v/v) acetic and destained in the same solution without dye.

Reversed-Phase High Performance Liquid Chromatography (RP-HPLC)

900 µl 0.1% (v/v) trifluoroacetic acid (TFA) was added to the incubation sample aliquots containing the 33-mer or the 26-mer, followed by filtration of the sample over a 0.22 um tyffrun filter. RP-HPLC of the samples was carried out using a HPLC Model 715 (Gilson, Middleton, Wis.) and a C-18 column (TSK-GEL 5 µm, ODS-120 T, 4.6×250 mm, TOSO-Haas, Montgomeryville, Pa.). The 33-mer, 26-mer and fragments thereof were eluted using a linear gradient from 0 to 55% buffer B (80% (v/v) acetonitrile and 0.1% (v/v) TFA) over a 75 min time interval at a flow rate of 1.0 ml/min (Sun X, et al., *Faseb J* 2009; 23:2691-701). The eluate was monitored at 219 and 230 nm and eluting fractions were collected using peak width and peaks sensitivity settings of 1.2 and 5, respectively (Unipoint version 3.3, Gilson).

Liquid Chromatography Electrospray Ionization Tandem Mass Spectrometry (LC-ESI-MS/MS)

Mass spectrometry was conducted using a capillary nano-flow liquid chromatography and electrospray ionization tandem mass spectrometer (LC-ESI-MS/MS). HPLC fractions containing individual gliadin degradation peptides were concentrated under vacuum, suspended in 5% acetonitrile in 0.1% formic acid, and 1-3 µl samples were injected using an autosampler (Micro AS, Thermo Finnigan, San Jose, Calif.). Separation/elution of peptides was achieved using an in-line capillary C-18 column (Magic C-18, Micron Bioresource) applying a gradient from 5 to 95% acetonitrile in 0.1% formic acid over a 35 min time interval at a flow rate of 250 nl/min. Micro-LC separation generated the total ion (base peak) chromatogram in a survey scan with an m/z range from 400-2000. This was followed by the sequential selection of five peptide ions for collision induced dissociation in descending order of signal intensity. The process incorporated a "dynamic exclusion" step of abundant peptide ions allowing also the detection of lower abundance peptide ions within the total ion chromatogram.

The raw MS data of the mixture of gliadins were searched against a total gluten/gliadin database (available on the world wide web at appliedbioinformatics.wur.nl) containing 618 gliadin and glutenin-derived protein entries from *Triticum aestivium* (wheat). The raw MS data of the fragments from the 33-mer and the 26-mer were searched against an in-house generated database containing just these two peptides. The MS/MS spectra obtained were searched using SEQUEST software (Bioworks Browser 3.3.1, Thermo-Finnigan). The SEQUEST X-corr values applied for non-tryptic peptides were as reported previously 20 and the ΔCn value was set at >0.1. Each search result was validated by manual inspection of the acquired MS/MS spectra to ensure that the fragment ions (e.g. b and y ions) were above background level and that each peptide was identified by at least three consecutive b- and y-ions. Due to the highly repetitive nature of the sequences within the gliadin structure and the limited diversity of amino acids, data could not be searched against reversed gluten/gliadin databases as a decoy. Rather, a stringent peptide probability setting of 0.05 was applied. To establish the suitability of the selected setting to avoid false positive identifications, MS/MS data of a digest of the 33-mer were searched against an all gluten database. This yielded only the identification of bona fide peptides contained within the 33-mer (data not shown).

pH Activity Profile of Gliadin-Degrading Enzymes in Mixed Dental Plague

Dental plaque bacteria suspended in 2 ml milliQ were sonicated using a Branson Sonifier 450 at an output setting of 5 (30 Watts). The sample was sonicated for 30 cycles of 10 seconds each and was chilled on ice to prevent temperature increase and protease inactivation. The supernatant was harvested by centrifugation for 2 min at 10,000×g, aliquoted into 8 equal portions and concentrated to ~20 ul using a speedvac (Savant). Each of the fractions was subjected to gliadin zymography (see details below). After electrophoresis and renaturing of the gel, the 8 gel lanes were separated with a razor blade and developed in 20 mM TrisBase/TrisHCl buffers adjusted to pH 3, 4, 5, 6, 7, 8, 9 or 10, respectively.

Liquid Iso-Electric Focusing (IEF) of Plaque Microbial Enzymes

A concentrated suspension of plaque bacteria in 2 ml milliQ water was sonicated as described above. The sample was centrifuged for 2 min at 10,000×g and the supernatant was diluted with water to a final volume of 3 ml (S1). The protein concentration in S1 was determined at 215 nm ($\epsilon$=20). A 300 µl aliquot of S1 was set aside. To the remainder of the solution, ampholytes 3/10 (Bio-Rad, Hercules, Calif.) were added to a final concentration of 5% (v/v) (S2). The electrode assemblies of a MicroRotofor focusing chamber (Bio-Rad) were filled with 0.1 M phosphoric acid (anode electrolyte) and 0.1 M sodium hydroxide (cathode electrolyte). S2 was applied to the separating chamber using a syringe and native liquid IEF was performed at 4° C. at 1 W and a gradual increase in voltage from 50 V to 320 V for 2 h. Ten fractions (F1-F10) containing plaque supernatant proteins separated based on iso-electric point over a pH range of 3-10 were harvested in a tray under vacuum according to the manufacturer's instructions. The pH value of F1-F10 (200 µl each) was determined using pH strips. S1 and F1-F10 were subsequently concentrated to ~20 ul using a speed-vac (Savant), and analyzed for protease activity by gliadin zymography.

Gliadin Zymography

Samples to be analyzed were suspended in sample buffer containing 0.25 M Tris/HCl, 10% glycerol, 2% SDS and 0.0025% bromophenol blue. The separating gel contained 375 mM Tris/HCl (pH 8.8), 6% or 8% acryl/bisacrylamide (19:1 ratio), 0.1% (w/v) SDS, 2 mg/ml gliadin, 0.05% (w/v) ammonium persulfate and 0.04% (v/v) TEMED. The stacking gel contained 126 mM TrisHCl (pH 6.8), 4% acryl/bisacrylamide (19:1), 0.1% (w/v) SDS, 0.05% (w/v) APS and 0.1% (v/v) TEMED. The running buffer contained 24 mM TrisBase, 192 mM glycine and 0.1% (w/v) SDS (pH 8.3). Electrophoresis was carried out at a constant voltage of 100 V at 4° C. Gels were renatured by washing for 2×30 min at 22° C. in zymogram renaturing buffer followed by washing for 2×20 min in zymogram developing buffer (both INVITROGEN™) and incubation in the same buffer for 48 h. Gels were stained in 40% methanol/10% acetic acid/0.1% Coomassie brilliant blue R-250 and destained in the same solution without dye.

Alignment of Gliadin Epitopes with Basic PRPs

Sequences of 10 T-cell stimulatory peptides 21 were aligned with basic PRP1, 2, 3, and 4 using the Sim alignment tool at the ExPASy proteomics server and ClustalX software (Version 2.0.12) applying the following parameters: comparison matrix: BLOSUM62; gap open penalty: 12; gap extension penalty: 4.

Example 2

Structural Similarities Between Gliadins and Basic PRPs

Figure 1B:
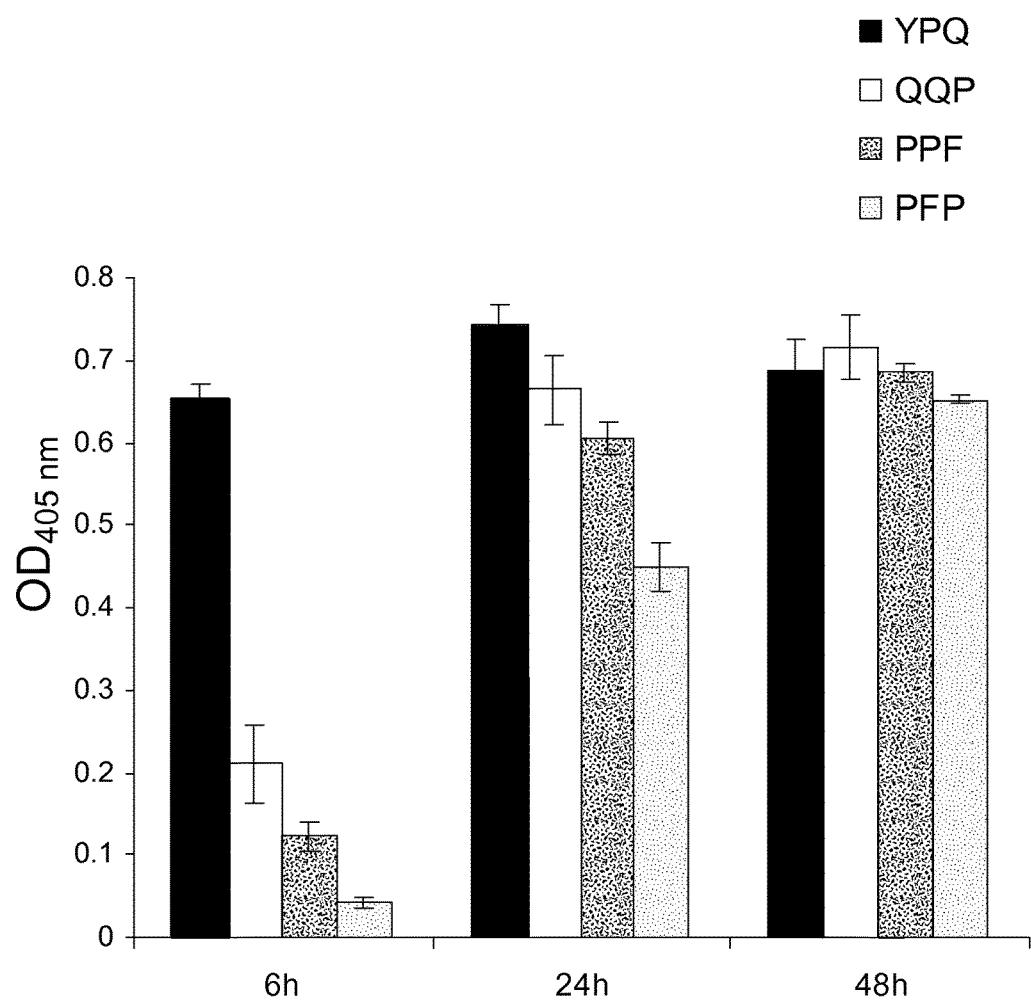

The recent discovery of an oral glutamine endoprotease cleaving basic PRPs prompted the inventors to study their capability to cleave immunogenic epitopes of gliadins which drive intestinal inflammation in celiac disease. When the primary amino acid sequences of gliadins and basic PRPs were compared, both protein families were found to share structural features. First, both gliadins and basic PRPs are very similar in size, averaging 307 and 357 amino acids (including signal peptides), respectively. Second, in gliadins as well as basic PRPs the amino acids glutamine (Q) and proline (P) combined make up about 50% of the total amino acid composition (Table 1). A noticeable difference though is that the relative proportions of glutamine and prolines in gliadins and basic PRPs is reversed (Table 1). Third, the XPQ sequence, prevalent in basic PRPs is also frequently occurring in gliadins. An example of a comparison between the amino acid sequences of a basic PRP2 and ω-5 gliadin is shown in FIG. 1. In some gliadins such as ω-5 gliadin, the XPQ tripeptide is present at an exceptionally high frequency, even exceeding that observed in basic PRBs (Table 1).

TABLE 1

Characteristics of gliadins from *Triticum aestivum* and human salivary basic proline-rich proteins

| Protein | # of amino acids[a] | % Q | % P | % (Q + P) | #XPQ |
|---|---|---|---|---|---|
| α/β gliadins | 288[b] | 34 | 15 | 49 | 7-22 |
| γ-gliadins | 276[c] | 31 | 16 | 47 | 2-38 |
| ω-gliadins | 356[d] | 24 | 19 | 43 | 8-72 |
| PRB1 | 392 | 16 | 37 | 53 | 47 |
| PRB2 | 416 | 15 | 37 | 52 | 50 |
| PRB3 | 309 | 14 | 35 | 49 | 20 |
| PRB4 | 310 | 14 | 34 | 48 | 21 |

[a] including signal peptides
[b,c,d] Average number of amino acids in α/β gliadins (58 entries), γ-gliadins (100 entries) and ω-gliadins (8 entries)

TABLE 2

Comparison of amino acid sequences of salivary basic proline-rich protein 2 (PRB2) (SEQ. ID. NO: 166) from human saliva and wheat omega-5 gliadin protein from *Triticum aestivum* * (SEQ. ID. NO: 167) showing the XPQ sequences therein.

sp|P02812|PRB_2HUMAN Basica salivary proline-rich protein 2 OS = Homo sapiens GN = PRB2 PE = 1 SV = 3

MLLILLSVALLALSSAQNLNEDVSQEESPSLIAGN<u>PQGAP</u><u>PQGGNK</u>
<u>PQGPPSPPGK</u><u>PQGPPPQGGNQ</u><u>PQGPPPPPGK</u><u>PQGPPP</u><u>QGGNK</u><u>PQGP</u>
PPPGK<u>PQGPPPQGDKSRSPRSPPGK</u><u>PQGPPPQGGNQ</u><u>PQGPPPPPGK</u>
<u>PQGPPPQGGNK</u><u>PQGPPPPGK</u><u>PQGPPPQGDNKSRSRSPPGK</u><u>PQGPP</u>
<u>PQGGNQ</u><u>PQGPPPPPGK</u><u>PQGPPPQGGNK</u><u>PQGPPPPGK</u><u>PQGPPQGDNK</u>

TABLE 2-continued

Comparison of amino acid sequences of salivary basic proline-rich protein 2 (PRB2) (SEQ. ID. NO: 166) from human saliva and wheat omega-5 gliadin protein from *Triticum aestivum* * (SEQ. ID. NO: 167) showing the XPQ sequences therein.

SQSARS<u>PPGK</u><u>PQGPPPQGGNQ</u><u>PQGPPPPPGK</u><u>PQGPPPQGGNKSQGP</u>
PPPGK<u>PQGPPPQGGSKSRSSRSPPGK</u><u>PQGPPPQGGNQ</u><u>PQGPPPPPG</u>
K<u>PQGPPPQGGNK</u><u>PQGPPPPGK</u><u>PQGPPPQGGSKSRSARSPPGK</u><u>PQGP</u>
<u>PQQEGNN</u><u>PQGPPPPAGGN</u><u>PQQPQA</u>PPAGQ<u>PQGPPRP</u><u>PQGGRPSRPP</u>
<u>Q</u> tr|Q402I5_WHEAT Omega-5 gliadin OS = *Triticum aestivum* PE = 4 SV = 1

MKTFIIFVLLAMAMNIASASRLLSPRGKELHT<u>PQEQF</u><u>PQQQQF</u>
<u>PQPQQ</u>
F<u>PQQQ</u>I<u>PQQHQ</u>I<u>PQQPQQF</u><u>PQQQQ</u>FL<u>QQQQI</u><u>PQQQ</u>I<u>PQQHQ</u>I<u>PQQPQQ</u>
F<u>PQQQQF</u><u>PQQHQS</u><u>PQQQF</u><u>PQQQF</u><u>PQQKL</u><u>PQQEF</u><u>PQQQ</u>ISQ<u>QPQQL</u>
<u>PQQQQI</u><u>PQQPQQ</u>FL<u>QQQQF</u><u>PQQQP</u><u>PQQHQF</u><u>PQQQL</u><u>PQQQQI</u><u>PQQQQ</u>
I<u>PQQPQQI</u><u>PQQQQI</u><u>PQQPQQF</u><u>PQQQF</u><u>PQQQF</u><u>PQQEF</u><u>PQQQQF</u>P
<u>QQQIA</u><u>RQPQQL</u><u>PQQQQI</u><u>PQQPQQF</u><u>PQQQQF</u><u>PQQQS</u><u>PQQQQF</u><u>PQQQF</u>P
<u>QQQQL</u><u>PQKQF</u><u>PQPQQI</u><u>PQQQQI</u><u>PQQF</u><u>QQF</u><u>PQQQF</u><u>PQQQQF</u><u>PQQQEF</u>P
<u>QQQF</u><u>PQQQF</u><u>HQQQL</u><u>PQQQF</u><u>PQQQF</u><u>PQQQF</u><u>PQQQQF</u><u>PQQQQL</u>TQ<u>QQF</u>
PR<u>PQQS</u>PE<u>QQQF</u><u>PQQQF</u><u>PQQP</u><u>PQQF</u><u>PQQQF</u>PIPYP<u>PQQ</u>SEEPSPYQQY
<u>PQQQ</u>PSGSDVISISGL

* XPQ sequences are underlined.

Hydrolysis of Gliadin-Derived Synthetic Enzyme Substrates

The KPQ tripeptide is abundant in salivary basic proline-rich proteins and cleaved effectively (Helmerhorst E J, et al., *J Biol Chem* 2008; 283: 19957-66). While KPQ is not present in gliadins, YPQ is a relatively abundant tripeptide. To study oral microbial enzyme specificities directed at gliadins, a Z-YPQ-pNA peptide was synthesized, as well as three other gliadin-derived tripeptide analogs, Z-QQP-pNA, Z-PPF-pNA and Z-PFP-pNA with Z representing benzyloxycarbonyl (protective group) and pNA representing paranitroanilide (reporter group). The substrates were incubated with a suspension of plaque bacteria and hydrolysis was monitored spectrophotometrically. Among the four substrates, Z-YPQ-pNA was most efficiently cleaved by enzymes contained in dental plaque (FIG. 1A). However, all four substrates ultimately were degraded (FIG. 1 B). No cleavage was observed when substrates were incubated in saliva ion buffer only, or with trypsin (data not shown). The diverse cleavage specificities associated with plaque bacteria indicate the presence of multiple proteolytic enzymes capable of targeting dietary gliadins.

Degradation of Gliadins

Figure 2:
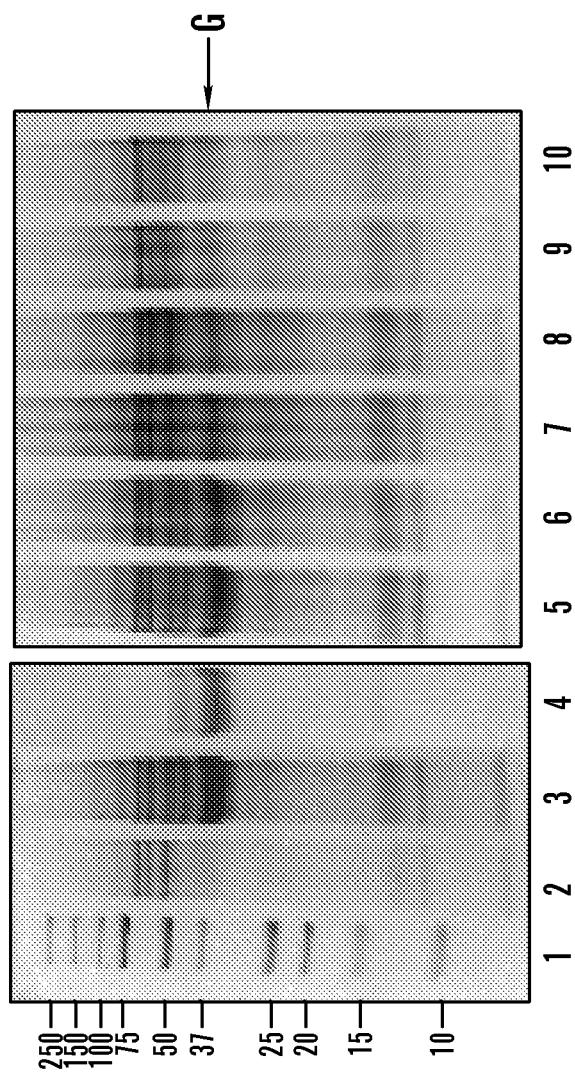
FIG. 2. Degradation of a mixture of gliadins (G) by oral plaque microorganisms. Dental plaque was suspended in saliva ion buffer to an $OD_{620}$ of 1.2. Gliadin (Sigma) was added to a final concentration of 250 μg/ml. After various incubation times at 37° C. 100 μl aliquots were removed, boiled and analyzed by SDS PAGE. Lane 1, MW std; lane 2: plaque bacterial suspension only (t=0); lane 3: plaque suspension+gliadin (t=0); lane 4: 25 μg gliadin (t=0); Lanes 5 to 10: plaque suspension+gliadin, sampled after t=0, t=2 h, t=4 h, t=6 h, t=24 h and t=48 h, respectively.

To investigate if gliadins were cleaved by oral microbial proteases, a commercial preparation of a mixture of all gliadins was used, containing a variety of α/β, ω- and γ-gliadins. When analyzed by SDS PAGE, the mixture appeared as major bands in the ~35-47 kD region (FIG. 2, lane 4). Other minor components, including traces of albumins, globulins and glutenins, may also be present but were likely low in content compared to the gliadins, due to the overall poor staining of proline-rich proteins with Coomassie brilliant blue. Studies were therefore focused on the protease sensitivity of the ~35-47 kDa protein bands. FIG. 2 shows that after ~6 h incubation with plaque bacteria the 35-47 kD bands were virtually completely degraded.

Proteolysis of Synthetic Gliadin Peptides (33-mer and 26-mer)

Within the gliadin sequences, certain peptide regions are particularly immunogenic and resistant to degradation by human-derived digestive enzymes. These are a 33-mer peptide present in α2-gliadin, also denoted as "superantigen" (Schuppan D, et al, *Gastroenterology* 2009; 137:1912-33; Shan L, et al. *Science* 2002; 297:2275-9; Hausch F, et al. *Am*

Figure 3A:
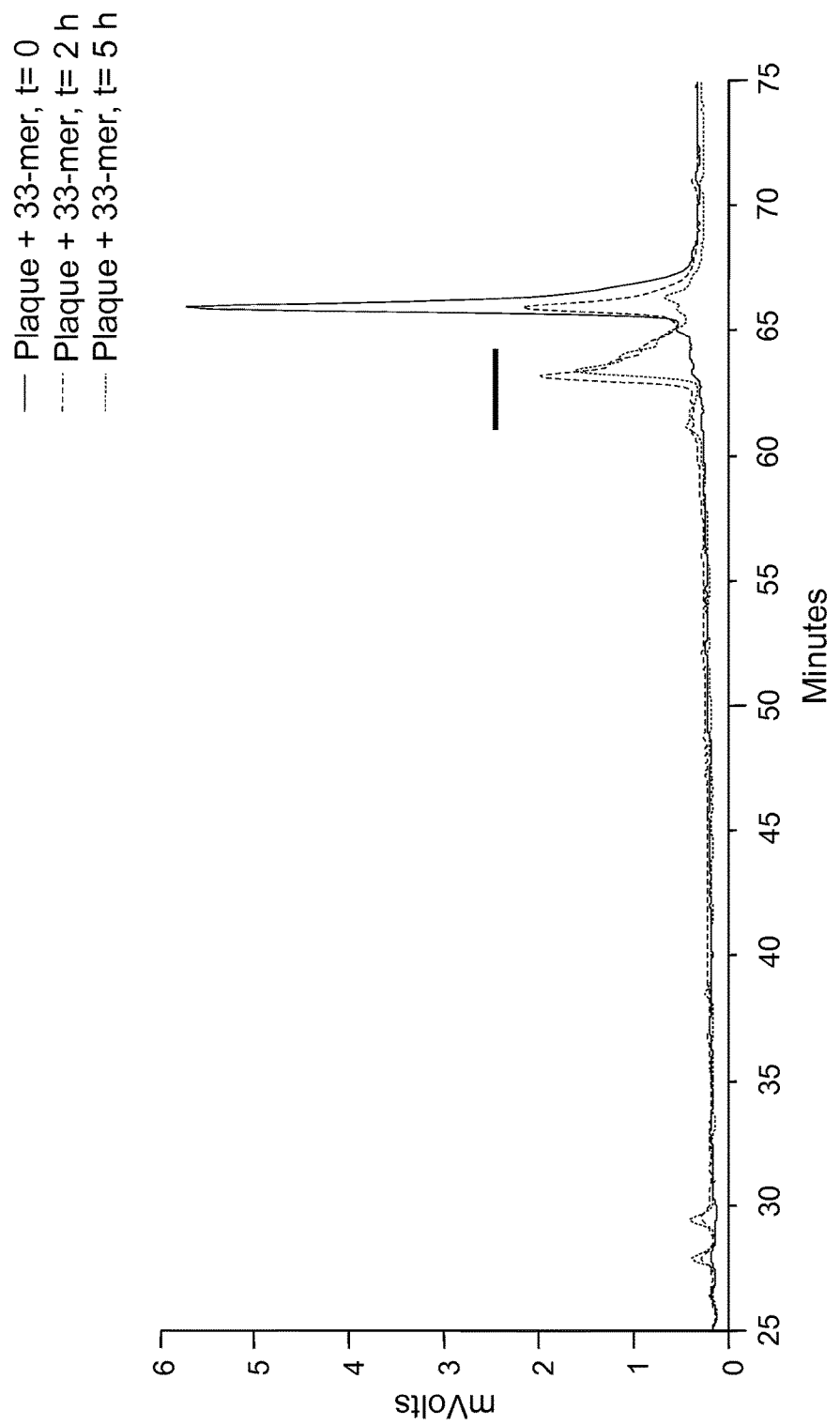
FIGS. 3A-3B. Degradation of gliadin-derived peptides by plaque bacteria. The 33-mer or the 26-mer was added to a final concentration of 250 μg/ml to a suspension of plaque bacteria suspended in saliva ion buffer ($OD_{620}$ 1.2). After 0, 2 h and 5 h of incubation at 37° C., 100 μl aliquots were removed, boiled and subjected to RP-HPLC.
Figure 3B:
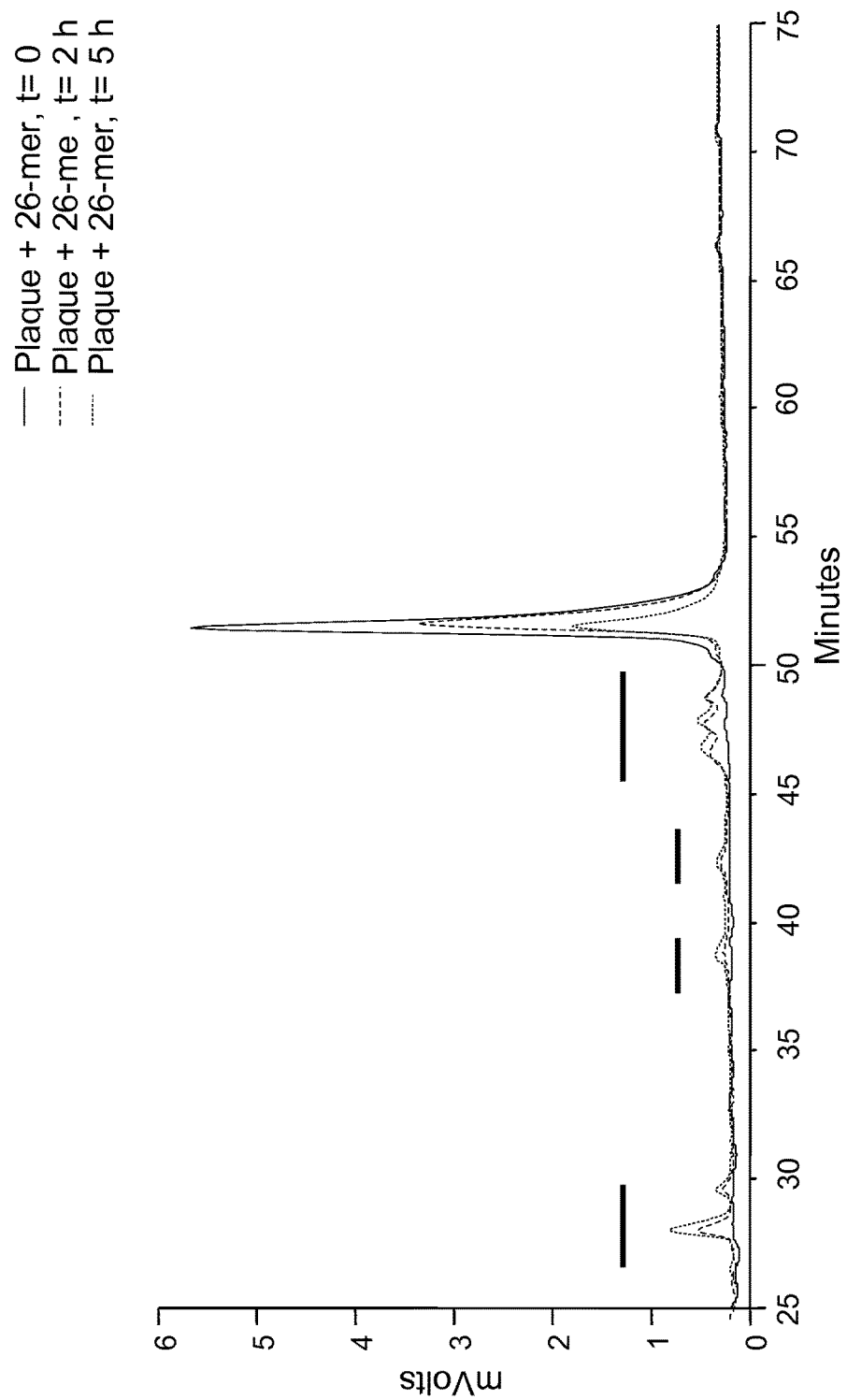
Figure 4:
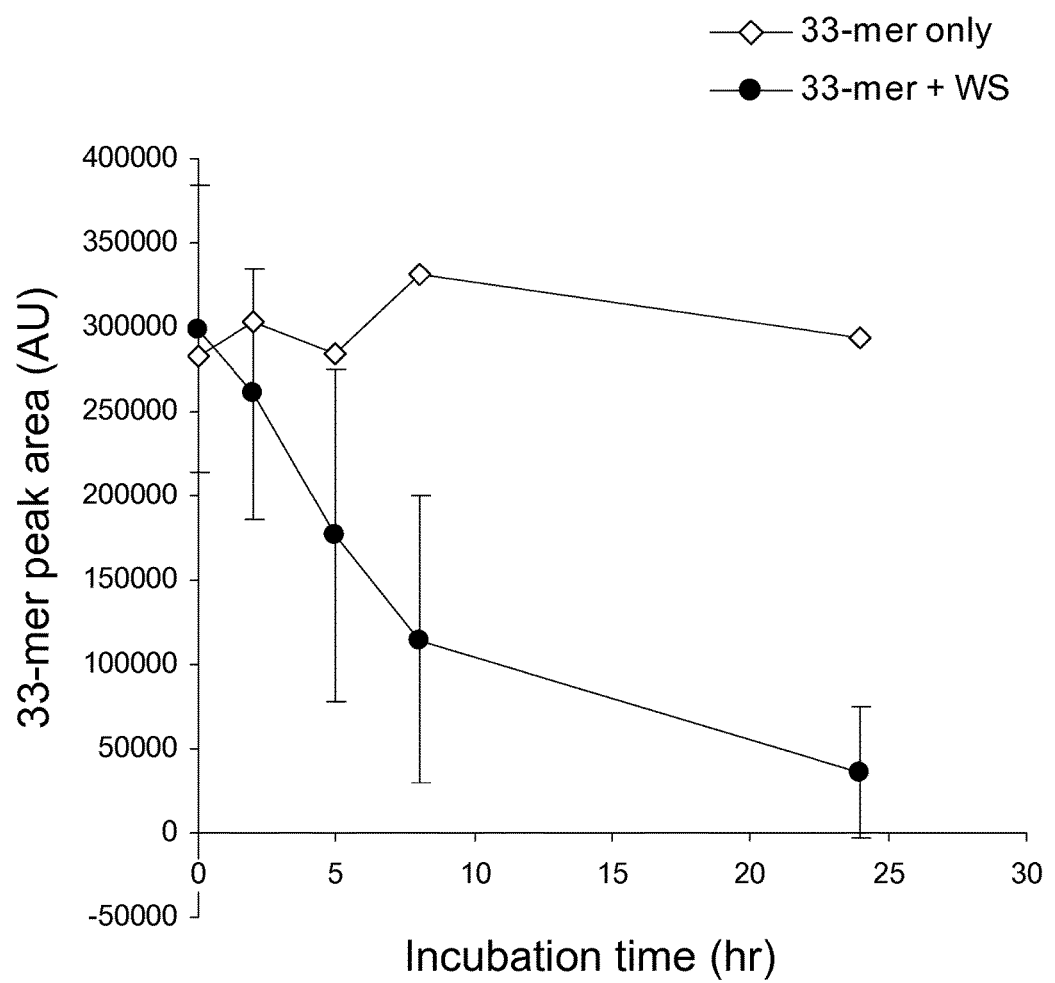
FIG. 4. Degradation of the 33-mer gliadin peptide in human whole saliva (WS). WS was collected from eight healthy subjects and 250 μg/ml of the 33-mer was added to each sample. After t=0 h, 2 h, 5 h, 8 h and 24 h, 100 μl sample aliquots were removed, boiled and analyzed by RP-HPLC. Plotted are the average peak areas of the 33-mer in the eight WS samples and the 33-mer incubated in saliva ion buffer (control).

*J Physiol Gastrointest Liver Physiol* 2002; 283: G996-G 1003), and a 26-mer domain derived from γ-gliadin (Shan L, et al., *J Proteome Res* 2005; 4:1732-41). The susceptibility of these peptides to proteolytic breakdown by oral microbial enzymes was investigated by RP-HPLC. The intact 33-mer peptide at the applied gradient eluted after 66 min (FIG. 3A). It was confirmed that both peptides are resistant to digestion by the major human digestive enzymes trypsin, chymotrypsin and pepsin after 24 h of incubation (data not shown). In a suspension of plaque bacteria, however, the 33-mer completely degraded after 5 h of incubation, as evidenced by disappearance of the peak at 66 min and appearance of degradation fragments eluting between 60-66 minutes and between 25 and 30 minutes. The 26-mer was also cleaved by dental plaque bacteria (FIG. 3B), yielding fragments eluting between 25 and 30 minutes and between 35 minutes and 52 minutes. In addition it was investigated if protease activities are detectable in human whole saliva (WS). WS contains about 108 oral microorganisms per ml and is continuously swallowed reaching more downstream regions of the gastro-intestinal tract. Data showed that the 33-mer was degraded in WS from all eight healthy human subjects examined, but that substantial variation in activities is noticeable between subjects (FIG. 4).

LC-ESI-MS/MS of Fragments from the 33-mer and 26-mer

Figure 7B:
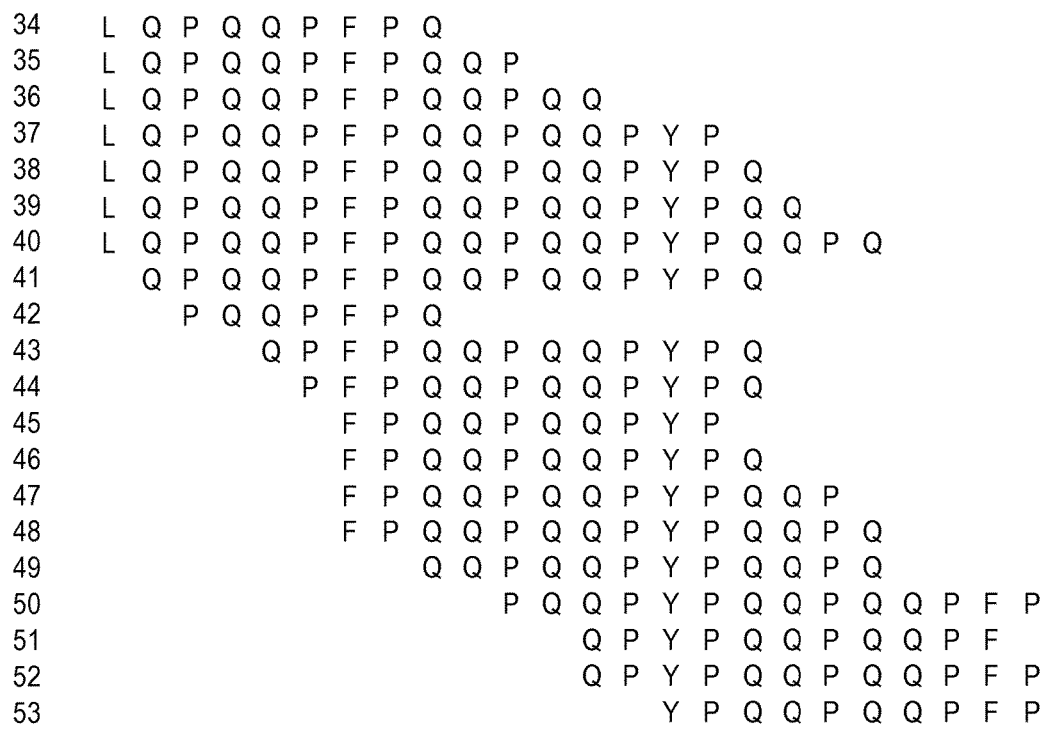

In order to anticipate if oral microbial enzymes could cleave and theoretically neutralize the immunogenic epitopes contained within the 33-mer and 26-mer sequences, the cleavage products of both peptides were structurally characterized by LC-ESI-MS/MS. The RP-HPLC fractions collected for this purpose are indicated with a horizontal bar in FIG. 3. The fragments generated from the 33-mer and the 26-mer are presented in FIGS. 7A and 7B. Short N- and C-terminal peptides (<9 amino acids) were not detected, since these eluded detection by LC-ESI-MS/MS for technical reasons. The peptides identified with high confidence show that virtually all sites are targeted in both the 33-mer and the 26-mer. While proteolysis did not abolish all immunogenic epitopes in the time span examined, the results together with hydrolysis of -pNA derivatized substrates indicate that the gliadins are excellent substrates for oral microbial enzymes.

pH Activity Profile of Oral Gliadin-Degrading Enzymes

Figure 5A:
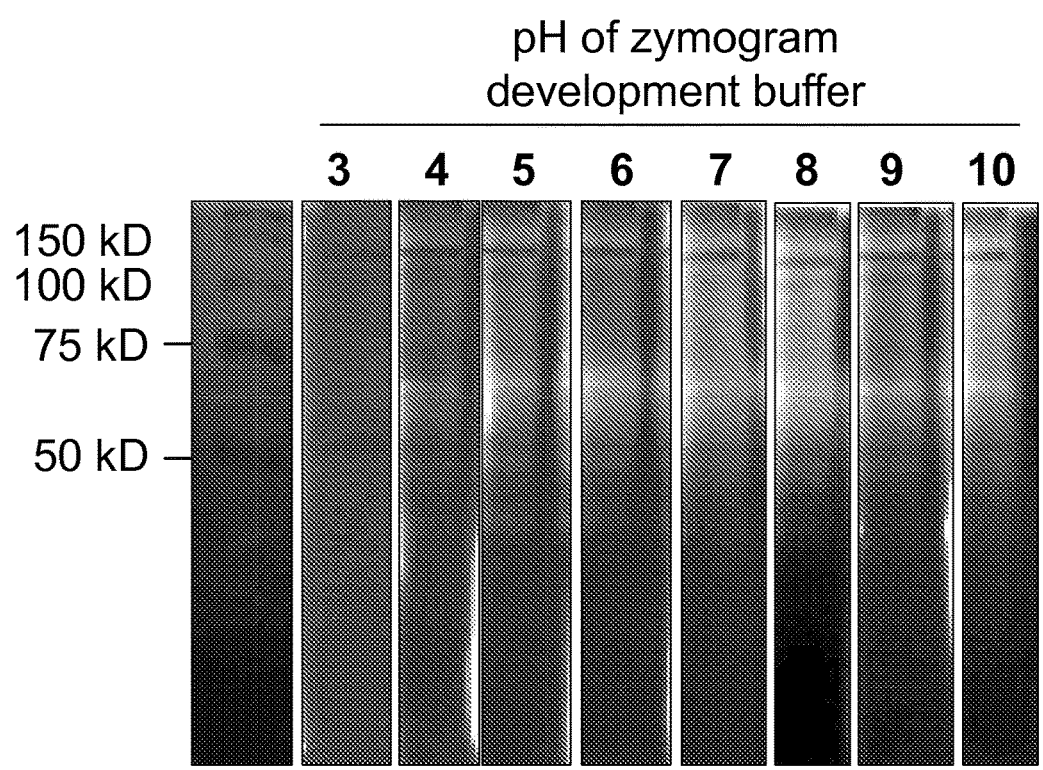
FIGS. 5A-5B. Determination of the pH activity profile of plaque bacterial enzymes by gliadin zymography and Z-YPQ-hydrolysis. 5A, sonicated plaque bacterial supernatant was aliquoted into eight fractions. Each fraction containing 90 μg protein was subjected to gliadin zymography and developed in buffers varying in pH from 3 to 10. Far left lane: MW standard. 5B, plaque bacteria were suspended to an $OD_{620}$ of 1.2 and mixed with Z-YPQ-pNA (200 μM). Hydrolysis was monitored spectrophotometrically. A representative graph of 3 independent experiments is shown.
Figure 5B:
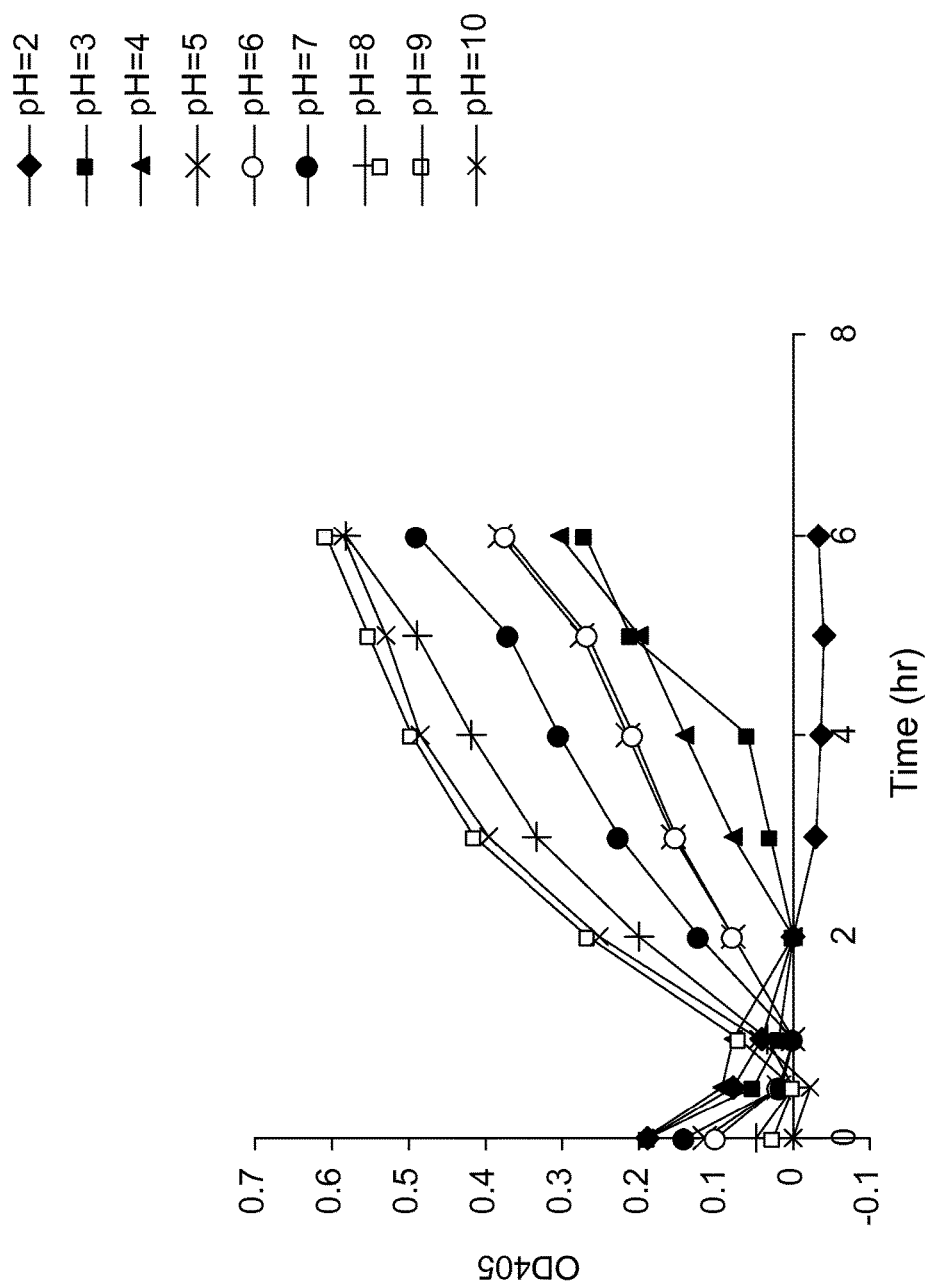

In view of the varying pH conditions along the gastro-intestinal tract, the pH activity profile of the oral gliadin-degrading enzymes was investigated. For this purpose plaque was sonicated, which released the enzymes into the supernatant. The supernatant fraction was subjected to gliadin zymography and developed in buffers with pH values ranging from 3 to 10 (FIG. 5A). The major activity was associated with bands of Mr~70 and Mr~140 kD Gliadin degradation was observed over a wide pH range, with clear activities from pH=4 extending to pH=10. Weak activity was observed at pH=3. Activity at this pH was confirmed with the synthetic substrate Z-YPQ-pNA (FIG. 5B). However, at pH=2 no activity could be demonstrated.

Overall Iso-Electric Points of Oral Gliadin-Degrading Enzymes

The pH activity experiment provided a first assessment of the overall molecular weights, and pH dependence of the major proteolytic components in dental plaque. To investigate additional physicochemical properties of the enzymes of interest, plaque supernatant protein mixture was subjected to iso-electric focusing (IEF). The pH of the ten fractions collected ranged from 2.5 to 10. Protease activities in each of the fractions were then determined by gliadin zymography (FIG. 6). Virtually all proteases had migrated to the anode and appeared in fractions with pH values of 3 and 4. In the most acidic fraction (pH 2.5) a high molecular weight protease of Mr~140 kD was observed, whereas at pH 3 and 4 the 70 kD and higher Mr bands were found. Weak protease activities were noted in fractions with pH values of 5, 6, and 7, but no protease activity was observed in fractions exhibiting more alkaline pH values. This indicates that the gliadin-degrading enzymes in the oral cavity are primarily acidic in nature.

Between 0.5 and 2% of a major part of the human population has more or less severe forms of celiac disease (Schuppan D, et al., *Gastroenterology* 2009; 137:1912-33). Most of those diagnosed profit from a strict life-long gluten free diet which is extremely difficult to maintain, especially since even minor gluten contamination in foods which are omnipresent needs to be ruled out (Troncone R, et al., *Curr Opin Clin Nutr Metab Care* 2008; 11:329-33). One of the therapeutic strategies to counteract or prevent the deleterious effect of these minor amounts of dietary gluten focuses on proteolytic enzymes to aid in their degradation, thus preventing their antigenic presentation to and activation of intestinal T cells (Shan L, et al., *Biochem J* 2004; 383:31 1-8; Stenman S M, et al. *Ann Med* 2009; 41:390-400). The results presented in the present investigation indicate that unexpectedly such potent digestive enzymes are naturally associated with the upper GI tract, i.e., the oral cavity. The studies on oral microbial proteases described herein indicate that: 1) the tripeptide YPQ which frequently occurs in gluten is preferentially targeted; 2) gliadin as well as two otherwise highly immunogenic and protease-resistant gliadin peptides are proteolytically degraded; 3) gliadin-degrading enzymes are active over a wide pH range (pH 3-10); and 4) most of the oral gliadin-degrading enzymes are acidic in nature, exhibiting IEP values of 2.5 to 4. These data indicate a role for the oral microbiome in gluten digestion. Furthermore, given the extended pH activity range and partial species overlap between oral, esophageal and duodenal GI microbiomes, it is likely that gliadin-degrading activities are present well beyond the oral region.

While novel with respect to source, gliadin degrading enzymes have been discovered in nature and are being exploited for their potential therapeutic application as dietary supplements in celiac disease. One of the enzymes that is being eyed for this purpose is EP-B2 which is a glutamine endoprotease produced from germinating wheat (Siegel M, et al., *Chem Biol* 2006; 13:649-58). Another group of enzymes capable of cleaving gluten are the prolyl endoproteases (PEP), specifically, PEP from *Aspergillus niger* (AN-PEP)26 and PEP from *Sphingomonas capsulata* (SC-PEP) (Gass J, *Cell Mol Life Sci* 2007; 64:345-55). EP-B2, AN-PEP and SC-PEP have been studied as food additives, either alone or in combination (Gass J, et al., *Gastroenterology* 2007; 133:472-80) and are in clinical phase I and IIa trials (e.g., Clinicaltrails.gov identifiers NCT00810654 and NCT00959114). An important difference between these enzymes and those found in the GI tract is the fact that the former enzymes originate from non-human associated sources, i.e. non-resident bacteria or plants. Resident gluten-degrading microorganisms as described herein are a viable source of novel enzyme(s) and offer the additional advantage of the potential to be exploited as probiotic agents to generate more long lasting changes in GI gluten digestive capacity.

Figure 8:
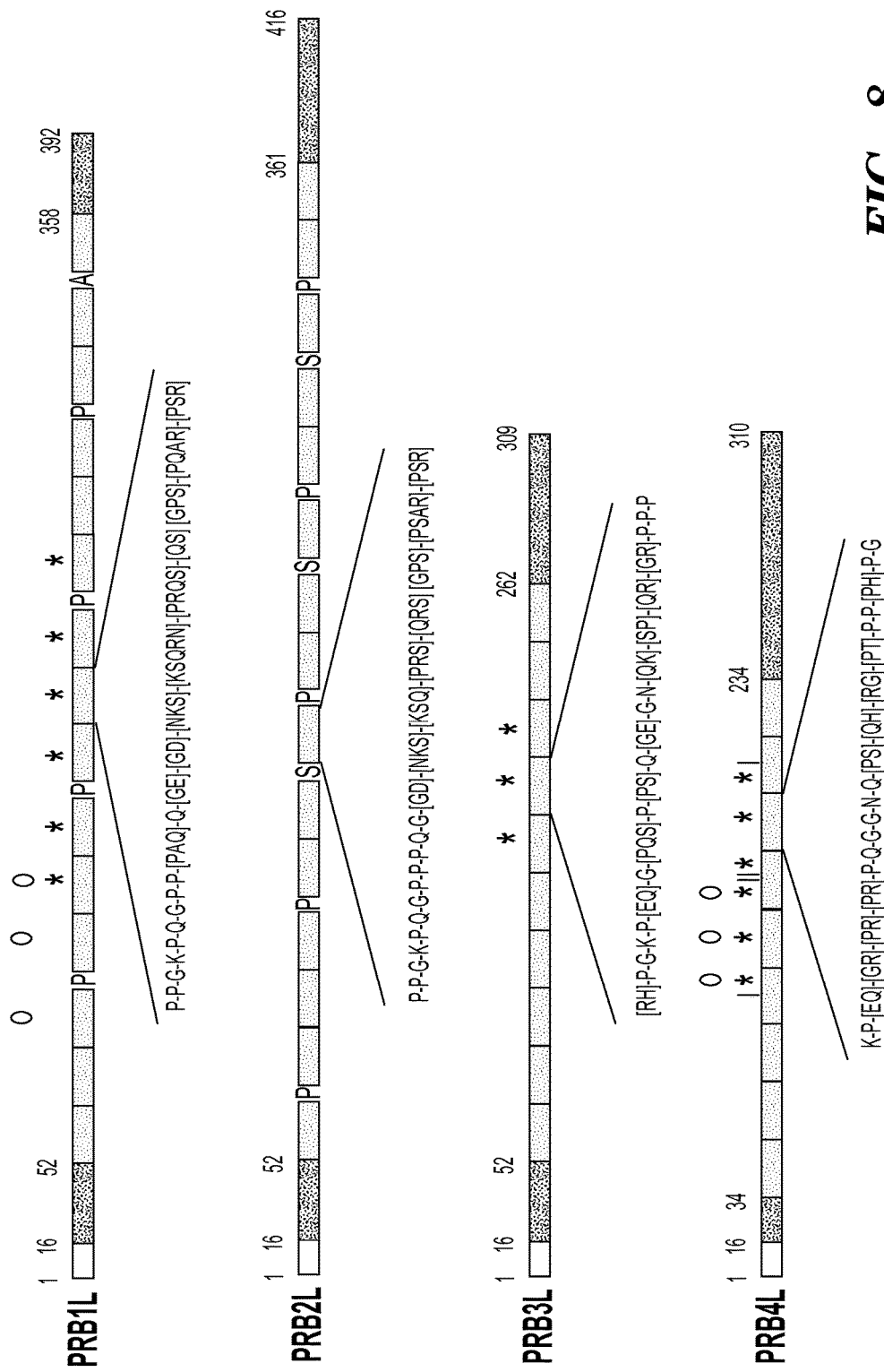
FIG. 8. Schematic presentation of the structures of human salivary basic proline-rich proteins (SEQ ID NOS 116-119, respectively, in order of appearance) (basic PRP). White boxed areas: signal peptides; dark grey boxed areas: non-repeat domains; light grey boxed areas: repeat domains. The consensus amino acid sequences of the repeat domains are indicated. In PRB1L and PRB2L some of the repeat domains are interspaced with single proline (P) or serine (S) residues. Open circles: repeat regions missing in the truncated M-allelic isoforms; diamonds: repeat regions missing in the truncated S-allelic isoforms. Note in PRB4 that the missing segments in the M and S isoforms overlap only in part with the repeat domains.

Human saliva-derived basic PRPs and wheat-derived gliadins show noticeable similarities in their amino acid composition with proline and glutamine being the chief constituent amino acids. Since gliadins contain now well defined T-cell stimulatory domains for patients carrying HLA-DQ2 or -DQ8 (Koning F. *J Mol Recognit* 2003; 16:333-6; Fleckenstein B, et al. *J Biol Chem* 2004; 279: 17607-16; Tollefsen S, et al. *J Clin Invest* 2006; 116:2226-36) it was studied to what extent these domains how structural overlap with basic PRPs. While it would be highly unlikely that the exact immunogenic domains stimulating T cell in patients with celiac disease are present in basic PRPs, given the successful reversal of celiac symptoms by gluten elimination from the diet in most patients, it is of interest that some celiac patients are refractory to a gluten-free diet (Biagi F, and Corazza G R. *Eur J Gastroenterol Hepatol* 2001; 13:561-5). The major basic salivary proline-rich proteins are encoded by PRB1, PRB2, PRB3 and PRB4 and contain multiple repeat domains of 20 or 21 amino acids (Maeda N, et al., *J Biol Chem* 1985; 260:11123-30) (FIG. 8). The alignment of gliadin epitopes (Koning F, and Vader W. *Science* 2003; 299:513-5) with selected regions in the basic PRP sequences is depicted in FIG. 9. The comparison revealed that gliadin epitopes are up to 50% homologous with basic PRP sequences. Due to the repeat domain structures in basic PRPs the gliadin-like domains are in some cases present in multiple copies. While the percentage overlap is substantial, it is evident from this analysis that no single point mutation in a basic PRP gene would generate a classical toxic gliadin epitope. Nevertheless, given the noted structural resemblances between these two protein families, and the fact that T-cell epitopes in gliadins typically cluster in regions with a high proline content (Arentz-Hansen H, et al., *Gastroenterology* 2002; 123:803-9), it will be of interest to characterize the salivary PRP geno- and phenotype of celiac patients. There is likely a biological reason, perhaps a nutritional reason that human saliva contains proteins that are so similar in composition to dietary proteins. Both protein families enter the GI tract and come into contact with resident GI microorganisms. Per day about 0.8 L of saliva is produced, primarily by the major salivary glands, and swallowed. Of note, salivary PRPs constitute approximately 70% of all secreted salivary proteins (Lamkin M S, et al., *Crit Rev Oral Biol Med* 1993; 4:251-9). With an average WS protein concentration of 2 mg/ml of protein, it can be estimated that about 1 g of PRPs and derived peptides enter the GI system each day. In addition, the Western daily diet contains about 10-20 g of gluten proteins, which are cleaved in part and incompletely by human digestive enzymes and, can be further fragmented by GI microbial proteases. In addition, glutamine endoprotease-producing microorganisms are also constantly being swallowed with saliva. It is possible that the proline/glutamine peptide profiles and/or GI microbial glutamine endoprotease activities show differences between healthy and celiac patients, which could be further exploited clinically.

Finally, these results provide a further characterization of the oral bacteria that secrete gliadin (gluten) degrading enzymes as well as identification and purification of their most active gliadin-cleaving enzymes. Apart from interesting biological findings, these bacteria and enzymes can lead to novel and effective strategies to detoxify immunogenic gluten peptides prior to reaching the proximal small intestine.

Example 3

Protease Identification in *Rothia mucilaginosa* ATCC 25296

Diethylaminoethyl Cellulose (DEAE) Ion-Exchange Chromatography

Figure 11:
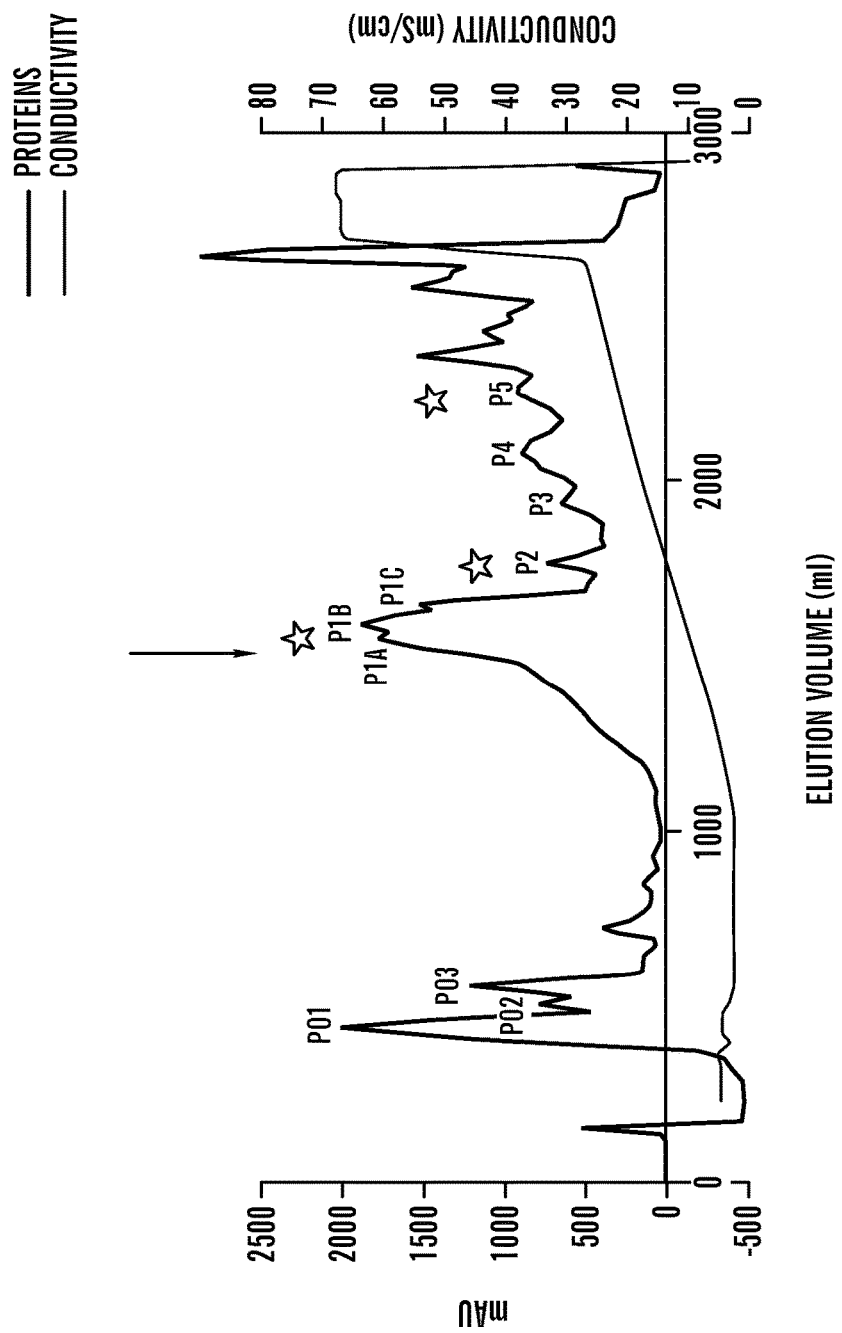
FIG. 11. DEAE chromatography of a sonicate of *Rothia mucilaginosa* ATCC 25296 cells (~90 mg). Dark trace: protein absorption spectrum at 214 nm; lighter trace: conductivity resulting from the applied salt gradient. Asterisks indicate protein fractions with enzymatic activity towards Z-YPQ-pNA. Arrow points to peak P1A that was subjected to hydrophobic interaction chromatography (HIC).

A DEAE column was prepared in house by using DEAE Sepharose Fast Flow resin, a weak anion exchange resin (GE Healthcare, Bjorkgatan, Sweden). The column the size was 2.6 cm×82.5 cm containing a volume of 438 ml. The chromatographic separation of proteins was achieved using the FPLC system AKTApurifier (GE Healthcare, Bjorkgatan, Sweden) at a flow rate of 1 ml/min with buffer A composed of 50 mM Tris-HCl, pH 8.0 and buffer B composed of 50 mM Tris-HCl, 1 M NaCl, pH8.0. The gradient applied was 0% buffer B over 657 min; 0-35%, 1533 min; 35-100%, 44 min; and 100%, 219 min. Fractions of 10 ml were collected. Enzyme activities in fractions of interest were assessed by adding Z-YPQ-pNA to a final concentration of 150 µM and following substrate hydrolysis spectrophotometrically at 405 nm (See FIG. 11). The peaks containing proteins with enzymatic activities were subjected to hydrophobic interaction chromatography.

Hydrophobic Interaction Chromatography (HIC)

Figure 12:
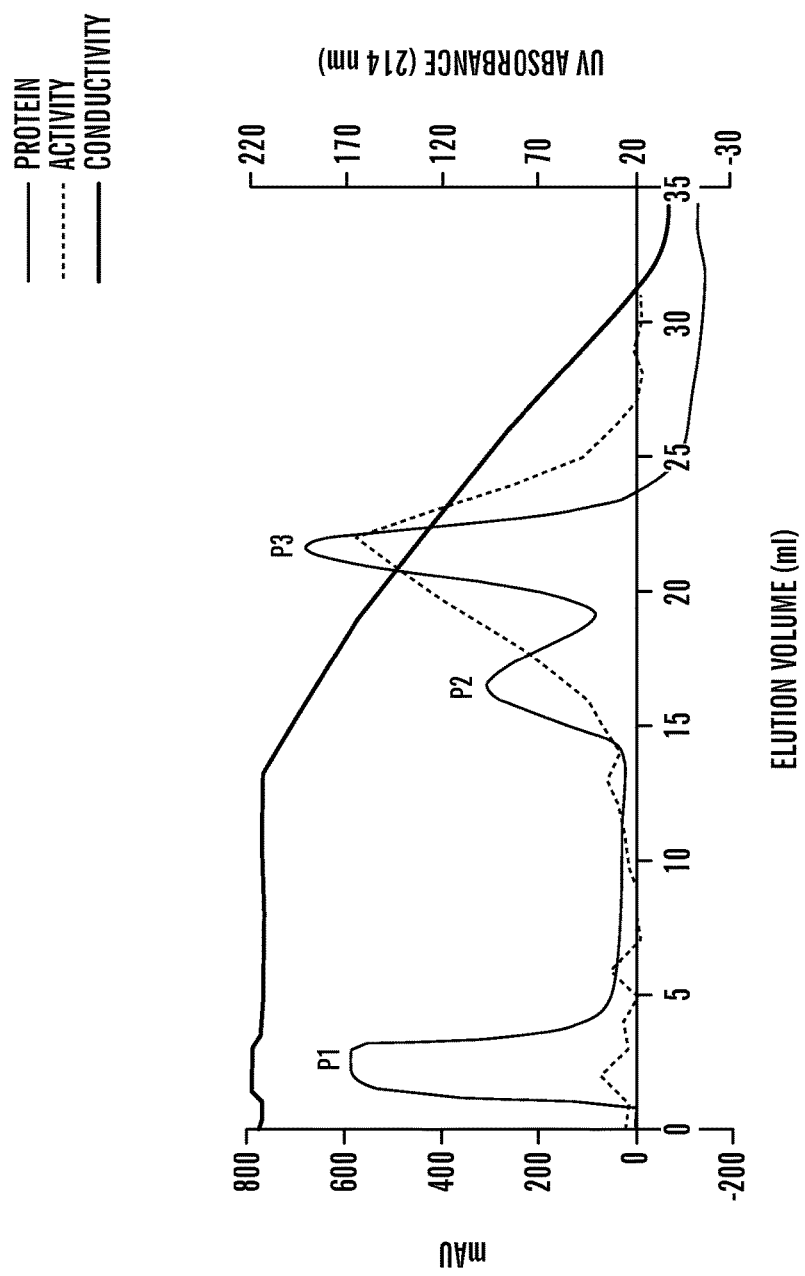
FIG. 12. Hydrophobic interaction chromatography (HIC) of DEAE Peak P1A. Dark trace: protein absorption at 214 nm. Lighter trace: conductivity reflecting the applied salt gradient. Dashed trace: activity evaluations of fractions towards Z-YPQ-pNA. Results show that activity was associated with HIC peak 3. The protein composition in this fraction was analyzed by LC-ESI-MS/MS.

Proteins in DEAE peak P1A were further separated by hydrophobic interaction chromatography using a pre-packed RESOURCE PHE column with a bed volume of 1 ml (GE Healthcare, Bjorkgatan, Sweden) (FIG. 12). After pre-equilibration in HIC-buffer A containing 50 mM Tris-HCl, 1.5 M $(NH_4)_2 SO_4$, pH8.0, the sample was loaded and protein separation was achieved with a gradient of 0% of HIC-buffer B (50 mM Tris-HCl, pH 8.0) over 12 min; 0-100%, 20 min; and 100% buffer B, 5 min. The flow rate was 0.5 ml/min and the fraction collection size was 0.5 ml. Enzymatic activities in the fractions towards Z-YPQ-pNA was assessed as described above.

LC-ESI-MS/MS Analysis

Proteins in HIC P3 were diluted in 50 mM ammonium bicarbonate buffer (pH 8.0) and digested with 2% trypsin (a ratio of 2 g trypsin per 100 g protein). After digestion, an aliquot of the peptide mixture was diluted in HPLC solvent A (2.5% acetonitrile, 0.1% formic acid) and analyzed by LC-ESI-MS/MS at the Taplin Mass Spectrometry facility, Harvard Medical School, Boston, Mass. A nano-scale reverse-phase HPLC capillary column was created by packing 5 µm C18 spherical silica beads into a fused silica capillary (100 µm inner diameter×~12 cm length) with a flame-drawn tip (2). After equilibrating the column each sample was loaded via a Famos auto sampler (LC Packings, San Francisco Calif.) onto the column. A gradient was formed and peptides were eluted with increasing concentrations of solvent B (97.5% acetonitrile, 0.1% formic acid).

As each peptide was eluted they were subjected to electrospray ionization and then they entered into an LTQ Orbitrap mass spectrometer (ThermoFinnigan, San Jose, Calif.). Eluting peptides were detected, isolated, and fragmented to produce a tandem mass spectrum of specific fragment ions for each peptide. Peptide sequences (and hence protein identity) were determined by matching protein or translated nucleotide databases with the acquired fragmentation pattern by the software program, Sequest (ThermoFinnigan, San Jose, Calif.). In this case, the data were searched against the *Rothia mucilaginosa* ATCC 25296 database which was downloaded from NCBI using Bioworks software version 3.1. Peptide filter criteria applied were delta CN>0.1, peptide probability <0.5 and Xcorr values 2.2. and 3.5 for Z=2+ and Z=3+ for fully tryptic peptides and 2.4 and 3.75 for Z=2+ and Z=3+ for partially tryptic peptides. These results of this analysis are shown in FIG. 13 and the sequences of the three proteins identified in the DEAE-P1a-HIC-P3 are shown in FIGS. 15-17.

The invention claimed is:

1. A lyophilized probiotic composition comprising an effective amount of *Rothia* species bacteria and a pharmaceutically acceptable carrier, wherein the bacteria comprises a gluten-degrading enzyme that retains protease activity at acidic pH of 3.0 as measured in an in vitro gliadin degradation assay for 3 hours using a synthetic substrate Z-YPQ-pNA, wherein the enzyme, when purified, comprises an iso-electric point within a pH range of 2.0-7.0 inclusive, and wherein the composition is formulated into granules.

2. The lyophilized composition of claim 1, wherein the *Rothia* species is *Rothia* species of 188, also known as *Rothia* sp. HOT-188 and *Rothia aeria* (strain WSA-8).

3. The lyophilized composition of claim 2, wherein the iso-electric point of the purified enzyme of the *Rothia* species bacteria is within a pH range of 2.0-4.0 inclusive.

4. The lyophilized composition of claim 3, wherein the enzyme comprises a molecular weight between 120-150 kDa inclusive.

5. The lyophilized composition of claim 1, wherein the pH in which the enzyme retains activity can vary between 2.5 and 5.0, inclusive.

6. The lyophilized composition of claim 1, wherein the enzyme degrades a gliadin protein, a fragment thereof, or a gluten-containing foodstuff or ingredient thereof.

7. The lyophilized composition of claim 6, wherein the degradation is partial.

8. The lyophilized composition of claim 6, wherein the fragment thereof is a 33-mer peptide of α2-gliadin or a 26-mer domain derived from γ-gliadin.

9. The lyophilized composition of claim 8, wherein the 33-mer peptide is SEQ. ID. NO: 1.

10. The lyophilized composition of claim 8, wherein the 26-mer domain is SEQ. ID. NO: 2.

11. The lyophilized composition of claim 6, wherein degradation occurs by cleaving the peptide bond after an amino acid sequence selected from the group consisting of -XPQ- -QQP-, -PPF-, -LYP- and/or -PFP-.

12. The lyophilized composition of claim 1, wherein the lyophilized composition is admixed with a gluten-containing foodstuff.

13. The lyophilized composition of claim 1, wherein the granules are packaged into a capsule.

14. The lyophilized composition of claim 1, wherein the composition is formulated to comprise an enteric coating.

* * * * *